(12) United States Patent
Wong et al.

(10) Patent No.: US 7,963,906 B2
(45) Date of Patent: *Jun. 21, 2011

(54) IMAGING AND EVALUATING EMBRYOS, OOCYTES, AND STEM CELLS

(75) Inventors: Connie C. Wong, Palo Alto, CA (US); Kevin E. Loewke, Menlo Park, CA (US); Barry Behr, Palo Alto, CA (US); Renee A. Reijo-Pera, Palo Alto, CA (US); Thomas M. Baer, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/982,341

(22) Filed: Dec. 30, 2010

(65) Prior Publication Data

US 2011/0105834 A1  May 5, 2011

Related U.S. Application Data

(63) Continuation of application No. 12/861,571, filed on Aug. 23, 2010.

(60) Provisional application No. 61/332,651, filed on May 7, 2010, provisional application No. 61/236,085, filed on Aug. 22, 2009.

(51) Int. Cl.
*A61B 17/43* (2006.01)
*A61D 7/00* (2006.01)
*C12N 5/00* (2006.01)
*C12N 5/02* (2006.01)

(52) U.S. Cl. .............. 600/33; 600/34; 600/35; 435/375; 435/83

(58) Field of Classification Search .............. 600/33
See application file for complete search history.

(56) References Cited

U.S. PATENT DOCUMENTS

2008/0247628 A1   10/2008   Ramsing

FOREIGN PATENT DOCUMENTS

WO    WO 2007/144001    12/2007

OTHER PUBLICATIONS

International Search Report issued Nov. 15, 2010 in connection with PCT Appl. No. PCT/US2010/046343.
Fenwick, et al., (2002) "Time from insemination to first cleavage predicts developmental competence of human preimplantation embryos in vitro," Human Reproduction, 17(2):407-412.
Lundin, et al., (2001) "Early embryo cleavage is a strong indicator of embryo quality in human IVF," Human Reproduction, 16(12):2652-2657.
Lequarre, et al., (2003) "Cell cycle duration at the time of maternal zygotic transition for in vitro produced bovine embryos: effect of oxygen tension and transcription inhibition," Biology of Reproduction, 69:1707-1713.
Brezinova, et al. (2009) "Evaluation of day one embryo quality and IVF outcome-a comparison of two scoring systems, "Reproductive Biology and Endocrinology, 7:9-14.
Lewin, et al. (1994) "Embryo growth rate in vitro as an indicator of embryo quality in IVF cycles," Journal of Assisted Reproduction and Genetics, 11(10):500-503.
Cummins, et al. (1986) "A formula for scoring human embryo growth rates in in vitro fertilization: Its value in predicting pregnancy and in comparison with visual estimates of embryo quality," Journal of In Vitro Fertilization and Embryo Transfer, 3(5):284-295.
Ramsing and Callesen, (2006) "Automated image analysis quantifies blastomere activity in time-lapse images to detect onset and duration of cell division during embryo development," Abstracts of the 22$^{nd}$ Annual Meeting of the ESHRE, Prague, Czech Republic, Jun. 18-21, 2006.
Francsovits, et al., (2006) "Examination of early cleavage and its importance in IVF treatment," Journal Reproduktionsmed Endokrinol, 3(6):367-372.

*Primary Examiner* — Valarie Bertoglio
(74) *Attorney, Agent, or Firm* — Cooley LLP

(57) ABSTRACT

Methods, compositions and kits for determining the developmental potential of one or more embryos or pluripotent cells and/or the presence of chromosomal abnormalities in one or more embryos or pluripotent cells are provided. These methods, compositions and kits find use in identifying embryos and oocytes in vitro that are most useful in treating infertility in humans.

14 Claims, 36 Drawing Sheets

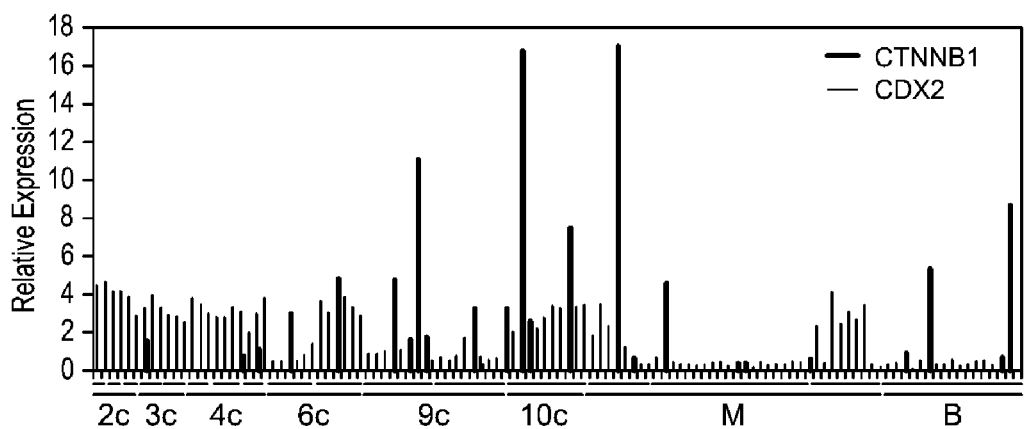
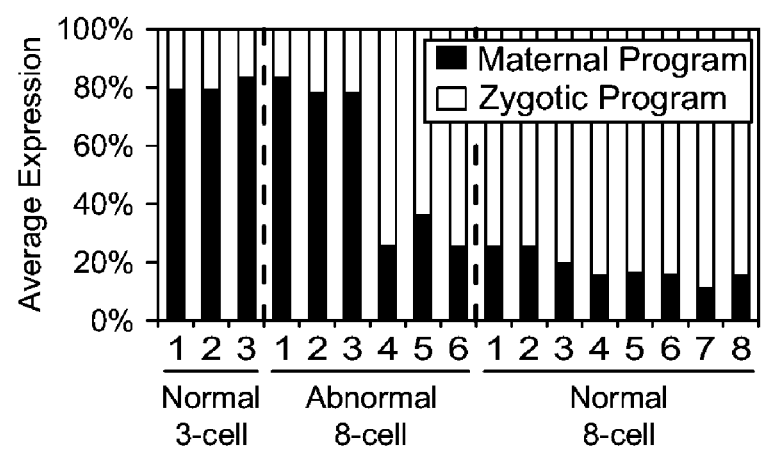
Fig. 12

Table 1

| Category | # of genes |
|---|---|
| Apoptosis | 5 |
| Cytokinesis | 10 |
| Differentiation | 9 |
| Embryonic gene activation | 10 |
| Epigenetics | 5 |
| Germ cell | 9 |
| Housekeeping | 10 |
| Ligand / receptor | 11 |
| Maternal effect | 8 |
| miRNA | 5 |
| Pluripotency | 7 |
| RNA processing | 7 |
| Sex specific | 2 |
| TE / ICM | 14 |
| Transcription factor | 11 |

Fig. 19

Table 2

| Pattern 1 | Pattern 2 | Pattern 4 |
|---|---|---|
| Anillin | CCNA1 | CTK7 |
| ATG5 | CCR4 | FABP5 |
| ATP2C1 | DNM2 | FGFR2 |
| Aurora A | EIF1AX | GAPDH |
| Bclaf1 | EIF4A3 | HMOX2 |
| Cofillin | EOMES | Hsp70 |
| CPEB1 | GDF3 | IGF2R |
| DAZL | GTF2A1 | LSM3 |
| Dgcr8 | H2AFZ | PABPC1 |
| DIAPH1 | JARID1B | PRMT5 |
| DIAPH2 | Nanog | RPLP0 |
| Dicer | NES | YY1 |
| DNAJA4 | Prdm14 | |
| DNMT3B | PTMA | Undefined |
| Drosha | RUNX2 | ATF4 |
| ECT2 | SERPINA1 | ATF7IP |
| EHMT2 | SERTAD1 | ATF7IP2 |
| FGFR1 | SOX2 | B2M |
| FYN | STELLAR | BNC2 |
| GABPB2 | YY1 | BTF3 |
| GDF9 | | CDX2 |
| HMOX2 | Pattern 3 | CTNNB1 |
| HPRT1 | B-actin | Dby |
| HSF1 | Bcl2 | Hsp70.1 |
| IGF1R | GCM1 | PRDM1 |
| IGF2R | HDAC7A | Symplekin |
| LAMB1 | IFITM1 | TARBP2 |
| MKLP2 | POU5F1 | Xist |
| MYLC2 | SALF | |
| NLRP5 | TGFBR2 | |
| PARN | | |
| PDCD5 | | |
| PVR | | |
| RhoA | | |
| Sycp3 | | |
| TACC3 | | |
| TAF4 | | |
| TBP | | |
| TERT | | |
| VASA | | |
| XPO5 | | |
| YBX2 | | |
| Zar1 | | |
| ZP1 | | |

Fig. 20

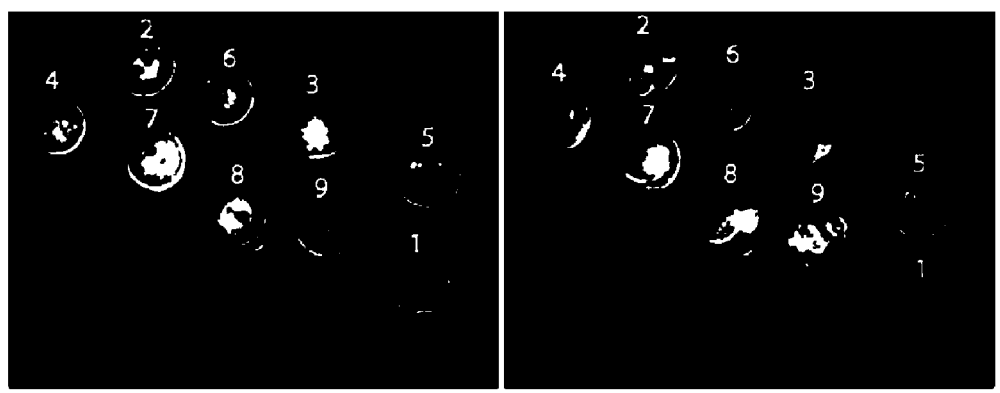
(a) Experiment 2, Station 2, Day 1      (b) Experiment 2, Station 2, Day 2.5
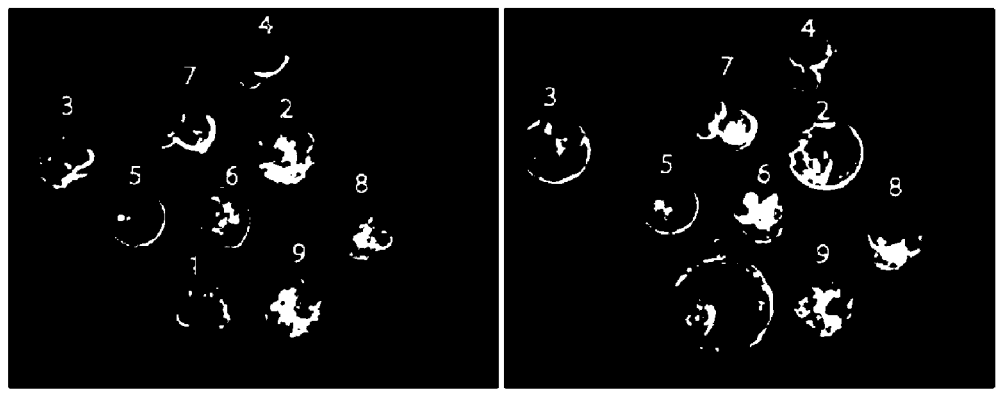
(c) Experiment 2, Station 2, Day 4      (d) Experiment 2, Station 2, Day 5.5
Fig. 25

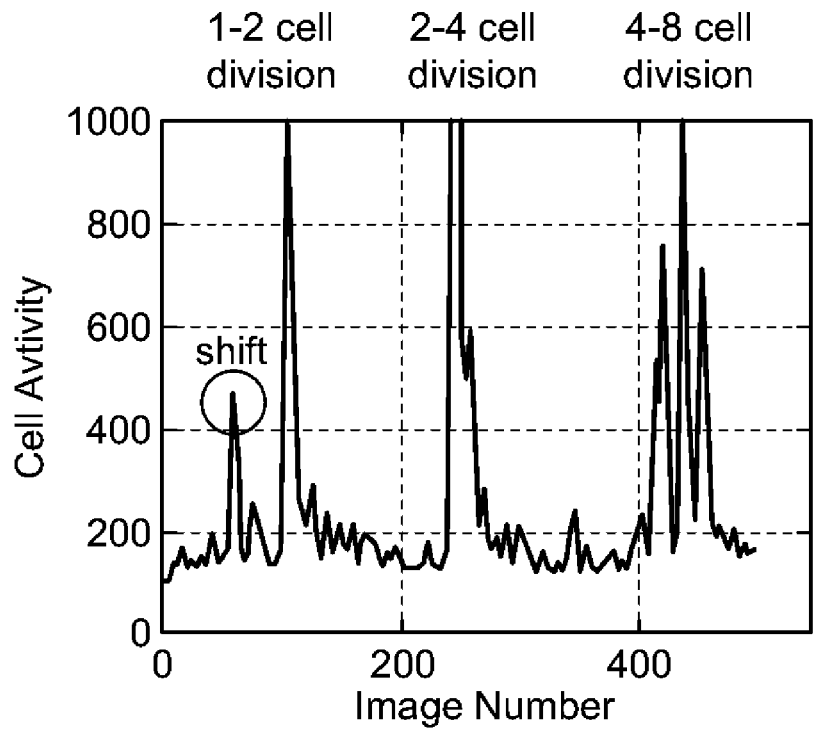
(a) Without prior image registration.
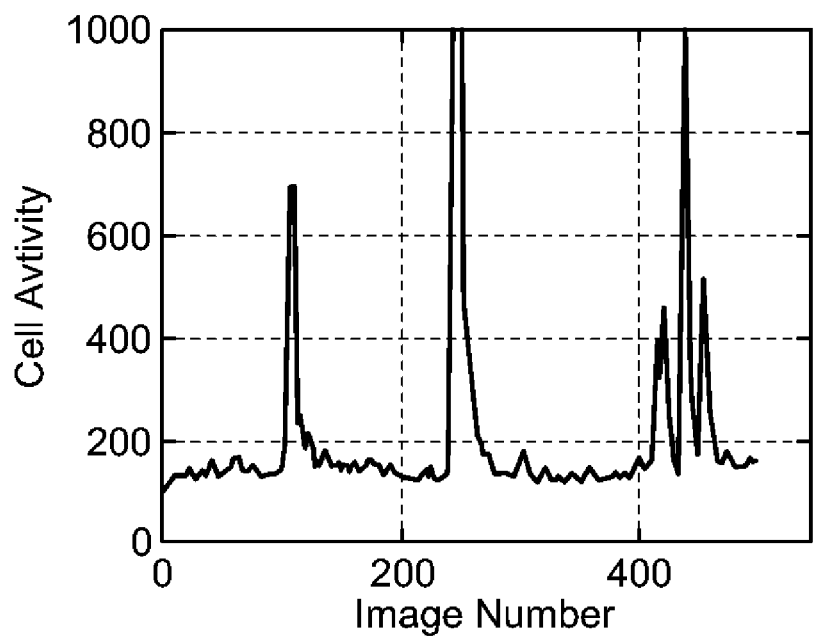
(b) With prior image registration.
Fig. 28

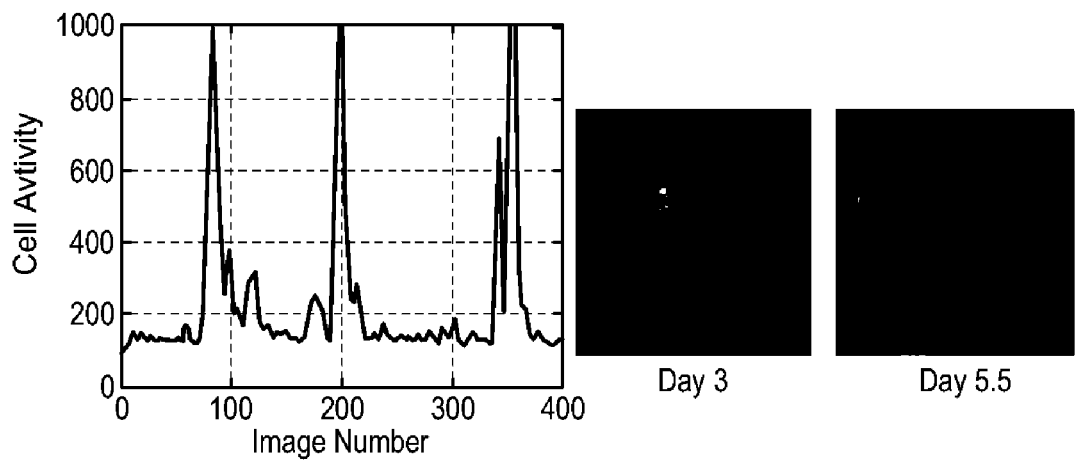
(a) Cell activity for normal embryo that reaches blastocyst.
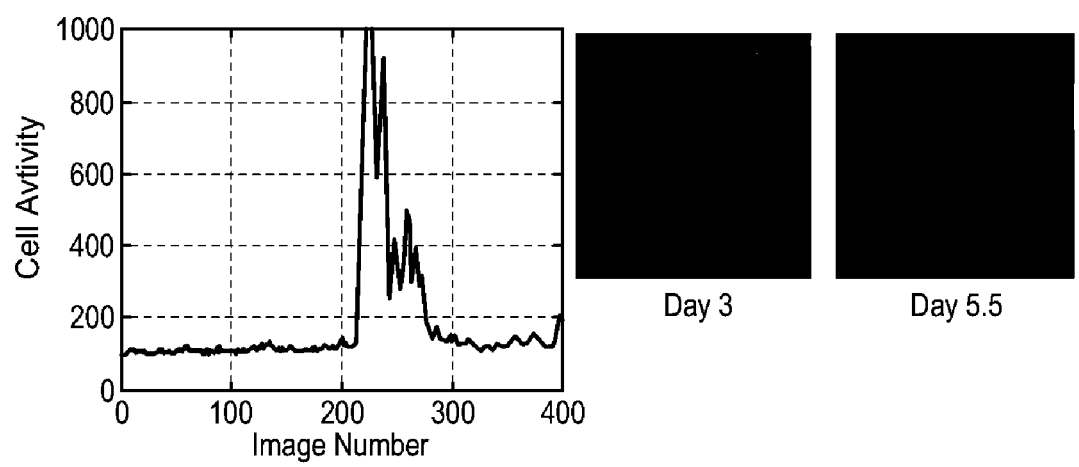
(b) Cell activity for abnormal embryo that arrests.
Fig. 29

Fig.32
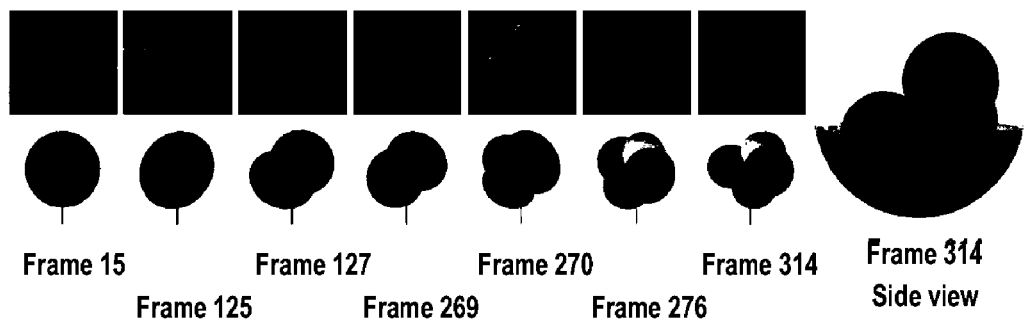
32A
32B

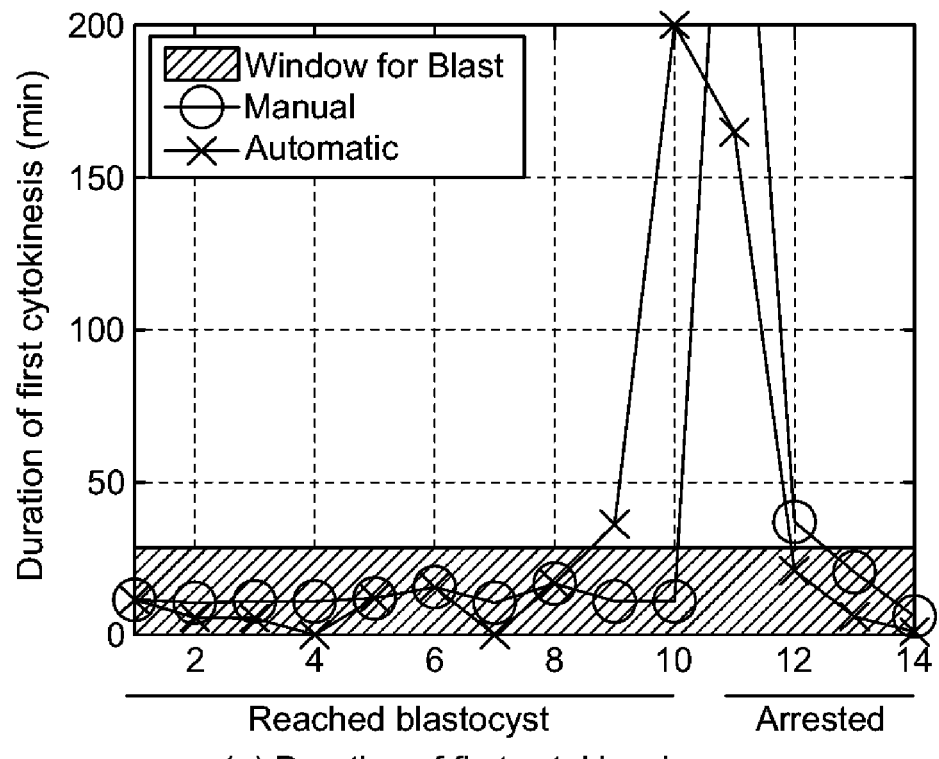
(a) Duration of first cytokinesis.
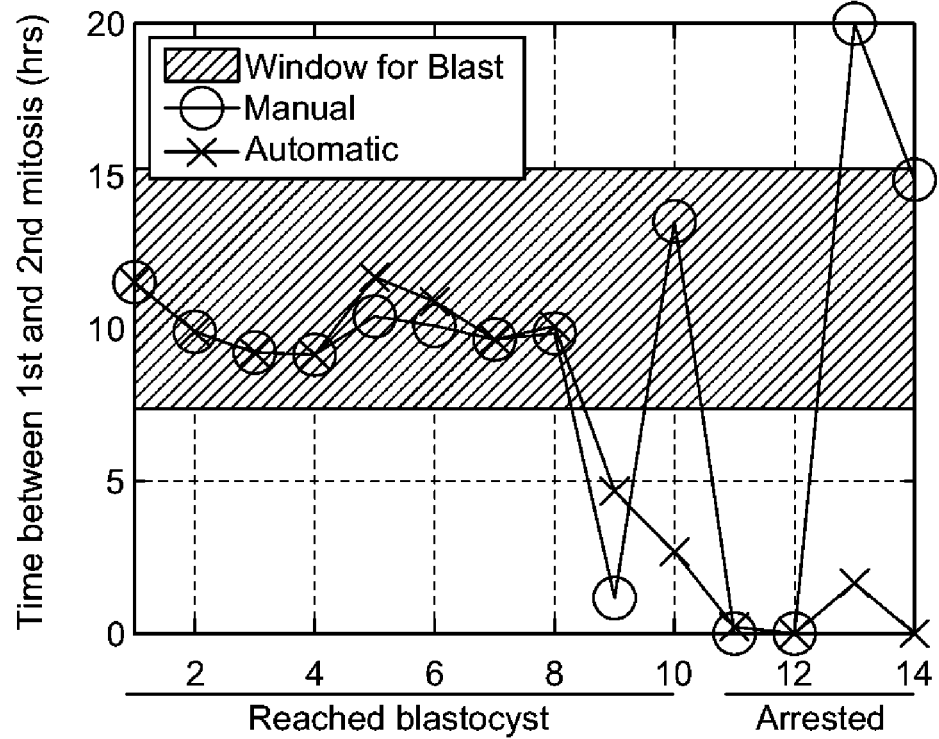
(b) Time between 1st and 2nd mitosis.
Fig. 34

IMAGING AND EVALUATING EMBRYOS, OOCYTES, AND STEM CELLS

CROSS REFERENCE TO RELATED APPLICATIONS

This application is a continuation of U.S. application Ser. No. 12/861,571, filed Aug. 23, 2010 and claims priority to U.S. Provisional Patent Application No. 61/332,651, filed May 7, 2010 and U.S. Provisional Patent Application No. 61/236,085, filed Aug. 22, 2009, all of which are herein incorporated by reference in their entireties.

FIELD OF THE INVENTION

This invention relates to the field of biological and clinical testing, and particularly the imaging and evaluation of zygotes/embryos, oocytes, and stem cells from both humans and animals.

BACKGROUND OF THE INVENTION

Infertility is a common health problem that affects 10-15% of couples of reproductive-age. In the United States alone in the year 2006, approximately 140,000 cycles of in vitro fertilization (IVF) were performed (cdc.gov/art). This resulted in the culture of more than a million embryos annually with variable, and often ill-defined, potential for implantation and development to term. The live birth rate, per cycle, following IVF was just 29%, while on average 30% of live births resulted in multiple gestations (cdc.gov/art). Multiple gestations have well-documented adverse outcomes for both the mother and fetuses, such as miscarriage, pre-term birth, and low birth rate. Potential causes for failure of IVF are diverse; however, since the introduction of IVF in 1978, one of the major challenges has been to identify the embryos that are most suitable for transfer and most likely to result in term pregnancy.

The understanding in the art of basic embryo development is limited as studies on human embryo biology remain challenging and often exempt from research funding. Consequently, most of the current knowledge of embryo development derives from studies of model organisms. However, while embryos from different species go through similar developmental stages, the timing varies by species. These differences, and many others make it inappropriate to directly extrapolate from one species to another. (Taft, R. E. (2008) Theriogenology 69(1):10-16). The general pathways of human development, as well as the fundamental underlying molecular determinants, are unique to human embryo development. For example, in mice, embryonic transcription is activated approximately 12 hours post-fertilization, concurrent with the first cleavage division, whereas in humans embryonic gene activation (EGA) occurs on day 3, around the 8-cell stage (Bell, C. E., et al. (2008) Mol. Hum. Reprod. 14:691-701; Braude, P., et al. (1988) Nature 332:459-461; Hamatani, T. et al. (2004) Proc. Natl. Acad. Sci. 101:10326-10331; Dobson, T. et al. (2004) Human Molecular Genetics 13(14):1461-1470). In addition, the genes that are modulated in early human development are unique (Dobson, T. et al. (2004) Human Molecular Genetics 13(14):1461-1470). Moreover, in other species such as the mouse, more than 85% of embryos cultured in vitro reach the blastocyst stage, one of the first major landmarks in mammalian development, whereas cultured human embryos have an average blastocyst formation rate of approximately 30-50%, with a high incidence of mosaicism and aberrant phenotypes, such as fragmentation and developmental arrest (Rienzi, L. et al. (2005) Reprod. Biomed. Online 10:669-681; Alikani, M., et al. (2005) Mol. Hum. Reprod. 11:335-344; Keltz, M. D., et al. (2006) Fertil. Steril. 86:321-324; French, D. B., et al. (2009) Fertil. Steril.). In spite of such differences, the majority of studies of preimplantation embryo development derive from model organisms and are difficult to relate to human embryo development (Zernicka-Goetz, M. (2002) Development 129:815-829; Wang, Q., et al. (2004) Dev Cell. 6:133-144; Bell, C. E., et al. (2008) Mol. Hum. Reprod. 14:691-701; Zernicka-Goetz, M. (2006) Curr. Opin. Genet. Dev. 16:406-412; Mtango, N. R., et al. (2008) Int. Rev. Cell. Mol. Biol. 268:223-290).

Traditionally in IVF clinics, human embryo viability has been assessed by simple morphologic observations such as the presence of uniformly-sized, mononucleate blastomeres and the degree of cellular fragmentation (Rijinders P M, Jansen C A M. (1998) Hum Reprod 13:2869-73; Milki A A, et al. (2002) Fertil Steril 77:1191-5). More recently, additional methods such as extended culture of embryos (to the blastocyst stage at day 5) and analysis of chromosomal status via preimplantation genetic diagnosis (PGD) have also been used to assess embryo quality (Milki A, et al. (2000) Fertil Steril 73:126-9; Fragouli E, (2009) Fertil Steril June 21 [EPub ahead of print]; El-Toukhy T, et al. (2009) Hum Reprod 6:20; Vanneste E, et al. (2009) Nat Med 15:577-83). However, potential risks of these methods also exist in that they prolong the culture period and disrupt embryo integrity (Manipalviratn S, et al. (2009) Fertil Steril 91:305-15; Mastenbroek S, et al. (2007) N Engl J. Med. 357:9-17).

Recently it has been shown that time-lapse imaging can be a useful tool to observe early embryo development. Some methods have used time-lapse imaging to monitor human embryo development following intracytoplasmic sperm injection (ICSI) (Nagy et al. (1994) Human Reproduction. 9(9):1743-1748; Payne et al. (1997) Human Reproduction. 12:532-541). Polar body extrusion and pro-nuclear formation were analyzed and correlated with good morphology on day 3. However, no parameters were correlated with blastocyst formation or pregnancy outcomes. Other methods have looked at the onset of first cleavage as an indicator to predict the viability of human embryos (Fenwick, et al. (2002) Human Reproduction, 17:407-412; Lundin, et al. (2001) Human Reproduction 16:2652-2657). However, these methods do not recognize the importance of the duration of cytokinesis or time intervals between early divisions.

Other methods have used time-lapse imaging to measure the timing and extent of cell divisions during early embryo development (WO/2007/144001). However, these methods disclose only a basic and general method for time-lapse imaging of bovine embryos, which are substantially different from human embryos in terms of developmental potential, morphological behavior, molecular and epigenetic programs, and timing and parameters surrounding transfer. For example, bovine embryos take substantially longer to implant compared to human embryos (30 days and 9 days, respectively). (Taft, (2008) Theriogenology 69(1):10-16. Moreover, no specific imaging parameters or time intervals are disclosed that might be predictive of human embryo viability.

More recently, time-lapse imaging has been used to observe human embryo development during the first 24 hours following fertilization (Lemmen et al. (2008) Reproductive BioMedicine Online 17(3):385-391). The synchrony of nuclei after the first division was found to correlate with pregnancy outcomes. However, this work concluded that early first cleavage was not an important predictive parameter, which contradicts previous studies (Fenwick, et al.

(2002) Human Reproduction 17:407-412; Lundin, et al. (2001) Human Reproduction 16:2652-2657).

Finally, no studies have validated the imaging parameters through correlation with the molecular programs or chromosomal composition of the embryos. Methods of human embryo evaluation are thus lacking in several respects and can be improved by the present methods, which involve novel applications of time-lapse microscopy, image analysis, and correlation of the imaging parameters with molecular profiles and chromosomal composition. The present invention addresses these issues.

SUMMARY OF THE INVENTION

Methods, compositions and kits for determining the developmental potential of one or more embryos or pluripotent cells in one or more embryos or pluripotent cells are provided. These methods, compositions and kits find, use in identifying embryos and oocytes in vitro that have a good developmental potential, i.e. the ability or capacity to develop into a blastocyst, which are thus useful in methods of treating infertility in humans, and the like.

In some aspects of the invention, methods are provided for determining the developmental potential of an embryo or a pluripotent cell. In such aspects, one or more cellular parameters of an embryo or pluripotent cell is measured to arrive at a cell parameter measurement. The cell parameter is then employed to provide a determination of the developmental potential of the embryo or pluripotent cell, which determination may be used to guide a clinical course of action. In some embodiments, the cell parameter is a morphological event that is measurable by time-lapse microscopy. In some embodiments, e.g. when an embryo is assayed, the one or more cell parameters is: the duration of a cytokinesis event, e.g. cytokinesis 1; the time interval between cytokinesis 1 and cytokinesis 2; and the time interval between cytokinesis 2 and cytokinesis 3. In certain embodiments, the duration of cell cycle 1 is also utilized as a cell parameter. In some embodiments, the cell parameter measurement is employed by comparing it to a comparable cell parameter measurement from a reference embryo, and using the result of this comparison to provide a determination of the developmental potential of the embryo, in some embodiments, the embryo is a human embryo. In some embodiments, the cell parameter is a gene expression level that is measured to arrive at a gene expression measurement. In some embodiments, the gene expression measurement is employed by comparing it to a gene expression measurement from a reference pluripotent cell or embryo or one or more cells therefrom, where result of this comparison is employed to provide a determination of the developmental potential of the pluripotent cell or embryo. In some embodiments, the embryo is a human embryo.

In some aspects of the invention, methods are provided for ranking embryos or pluripotent cells for their developmental potential relative to the other embryos or pluripotent cells in the group. In such embodiments, one or more cellular parameters of the embryos or pluripotent cells in the group is measured to arrive at a cell parameter measurement for each of the embryos or pluripotent cells. The cell parameter measurements are then employed to determine the developmental potential of each of the embryos or pluripotent cells in the group relative to one another, which determination may be used to guide a clinical course of action. In some embodiments, the cell parameter is a morphological event that is measurable by time-lapse microscopy. In some embodiments, e.g. when embryos are ranked, the one or more cell parameters are the duration of a cytokinesis event, e.g. cytokinesis 1; the time interval between cytokinesis 1 and cytokinesis 2; and the time interval between cytokinesis 2 and cytokinesis 3. In certain embodiments, the duration of cell cycle 1 is also measured. In some embodiments, the cell parameter is the expression level of one or more genes. In some embodiments, the one or more cell parameter measurements are employed by comparing the cell parameter measurements from each of the embryos or pluripotent cells in the group to one another to determine the developmental potential of the embryos or pluripotent cells relative to one another. In some embodiments, the one or more cell parameter measurements are employed by comparing each cell parameter measurement to a cell parameter measurement from a reference embryo or pluripotent cell to determine the developmental potential for each embryo or pluripotent cell, and comparing those developmental potentials to determine the developmental potential of the embryos or pluripotent cells relative to one another.

In some aspects of the invention, methods are provided for providing embryos with good developmental potential for transfer to a female for assisted reproduction (IVF). In such aspects, one or more embryos is cultured under conditions sufficient for embryo development. One or more cellular parameters is then measured in the one or more embryos to arrive at a cell parameter measurement. The cell parameter measurement is then employed to provide a determination of the developmental potential of the one or more embryos. The one or more embryos that demonstrate good developmental potential is then transferred into a female.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity, included in the drawings are the following figures.

FIG. 12 shows gene expression of genes from single blastomeres at different stages. (A) Gene expression of two genes, CTNNB1 and CDX2 from single blastomeres plotted at different cell stages and showing changes in these gene expression levels at different stages, e.g. 2 cells, 3 cells, morula and blastocyst. (B) Gene expression signatures in bars representing genes expressed in the maternal program as compared to genes expressed from the zygotic program.

FIG. 19 is a table of the categories into which the genes assayed for expression level may be categorized, including the number of genes per category.

FIG. 20 is a table of the four Embryonic Stage Specific Patterns (ESSPs) that were identified during gene expression analysis of 141 normally developed single embryos and single blastomeres, and the categorization of the genes into each one of the these categories.

FIG. 23A shows the microscopes, and FIG. 23B shows the microscopes inside and incubator.

FIG. 25 A through D is a series of four photographs showing selected time-lapse image from experiment 2, station 2. FIGS. 25A and 25B are images captured before media change, and FIGS. 25C and 25D are images captured after media change.

FIGS. 26A and 26B are images captured before media change, and FIGS. 26C and 26D are images captured after media change.

FIGS. 27 A and B are drawings of a custom petri dish with micro-wells.

FIGS. 28 A and B are graphs showing cell activity with and without prior image registration. FIGS. 28A and 28B together show that registration cleans up the results and removes spikes due to embryo shifting or rotating.

FIGS. 29 A and B are graphs (left) and cell photographs (right) showing cell activity for normal and abnormal embryos. Together, FIG. 29A and FIG. 29B show that, at day 3, the embryos have similar morphology, but their cell activity plots are drastically different and only one of them develops into a blastocyst.

FIGS. 32 A and B is a series of photographs and drawings showing two successful cases of 3D cell tracking. The illustrations under each photo of an embryo show the top-down view of the 3D model, except for frame 314 and frame 228, which show side-views of the models in frame 314 and frame 228, respectively. The image frames were captured every 5 minutes.

FIGS. 34 A and B are graphs showing a comparison of automated vs. manual image analysis for a set of 14 embryos.

FIG. 34A shows the comparison for the duration of first cytokinesis, and FIG. 34B shows the comparison for the time between $1^{st}$ and $2^{nd}$ mitosis.

DETAILED DESCRIPTION OF THE INVENTION

Figure 1:
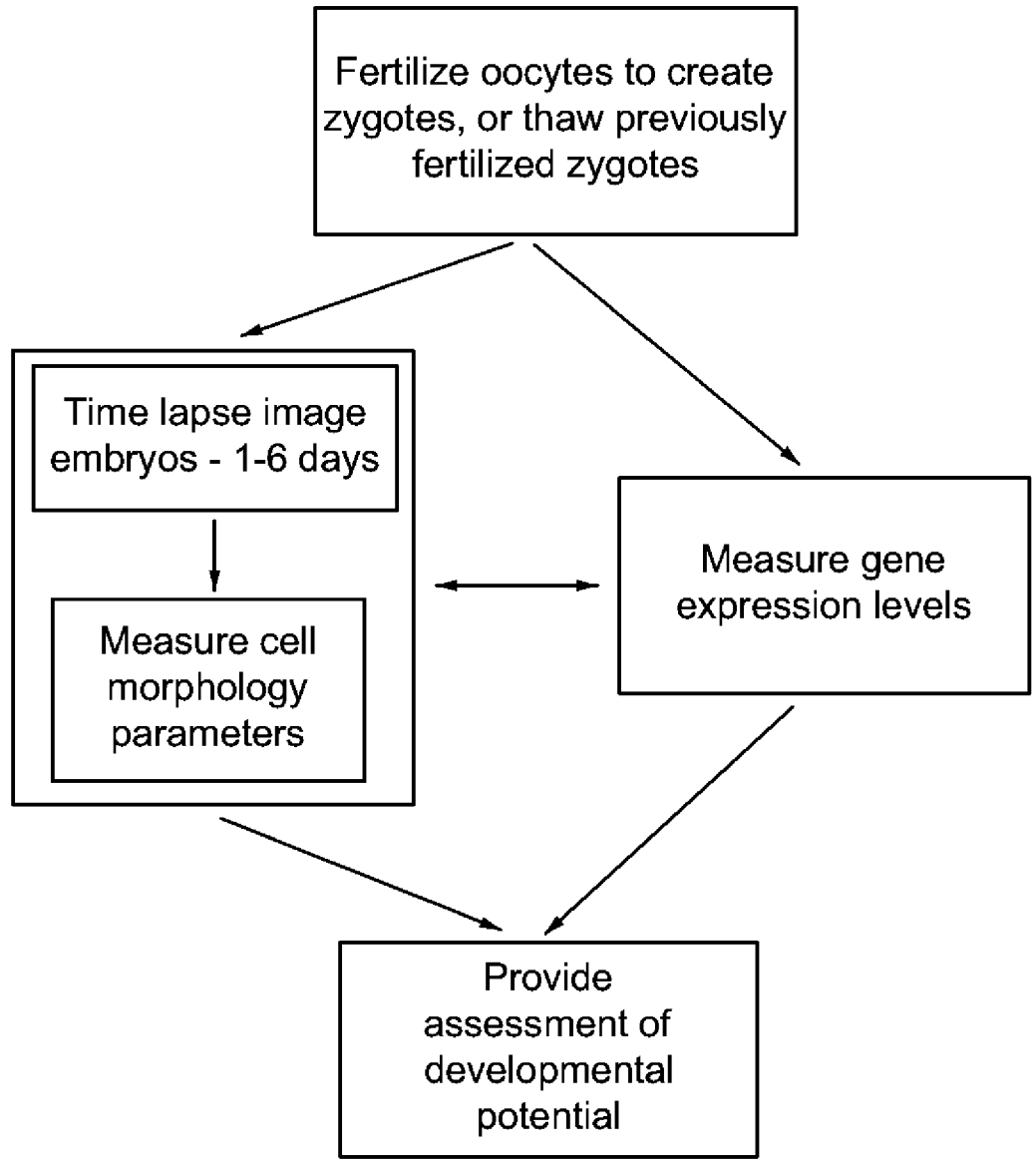
FIG. 1 is a flow chart showing processes used to evaluate embryos.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Methods, compositions and kits for determining the developmental potential of one or more embryos or pluripotent cells and/or the presence of chromosomal abnormalities in one or more embryos or pluripotent cells are provided. These methods, compositions and kits find use in identifying embryos and oocytes in vitro that are most useful in treating infertility in humans. These and other objects, advantages, and features of the invention will become apparent to those persons skilled in the art upon reading the details of the subject methods and compositions as more fully described below.

The terms "developmental potential" and "developmental competence" are used herein to refer to the ability or capacity of a healthy embryo or pluripotent cell to grow or develop.

The term "embryo' is used herein to refer both to the zygote that is formed when two haploid gametic cells, e.g. an unfertilized secondary oocyte and a sperm cell, unite to form a diploid totipotent cell, e.g. a fertilized ovum, and to the embryo that results from the immediately subsequent cell divisions, i.e. embryonic cleavage, up through the morula, i.e. 16-cell stage and the blastocyst stage (with differentiated trophoectoderm and inner cell mass).

The term "pluripotent cell' is used herein to mean any cell that has the ability to differentiate into multiple types of cells in an organism. Examples of pluripotent cells include stem cells oocytes, and 1-cell embryos (i.e. zygotes).

The term "stem cell' is used herein to refer to a cell or a population of cells which: (a) has the ability to self-renew, and (b) has the potential to give rise to diverse differentiated cell types. Frequently, a stem cell has the potential to give rise to multiple lineages of cells. As used herein, a stem cell may be a totipotent stem cell, e.g. a fertilized oocyte, which gives rise to all of the embryonic and extraembryonic tissues of an organism; a pluripotent stem cell, e.g. an embryonic stem (ES) cell, embryonic germ (EG) cell, or an induced pluripotent stem (iPS) cell, which gives rise to all of embryonic tissues of an organism, i.e. endoderm, mesoderm, and ectoderm lineages; a multipotent stem cell, e.g. a mesenchymal stem cell, which gives rise to at least two of the embryonic tissues of an organism, i.e. at least two of endoderm, mesoderm and ectoderm lineages, or it may be a tissue-specific stem cell, which gives rise to multiple types of differentiated cells of a particular tissue. Tissue-specific stem cells include tissue-specific embryonic cells, which give rise to the cells of a particular tissue, and somatic stem cells, which reside in adult tissues and can give rise to the cells of that tissue, e.g. neural stem cells, which give rise to all of the cells of the central nervous system, satellite cells, which give rise to skeletal muscle, and hematopoietic stem cells, which give rise to all of the cells of the hematopoietic system.

The term "oocyte" is used herein to refer to an unfertilized female germ cell, or gamete. Oocytes of the subject application may be primary oocytes, in which case they are positioned to go through or are going through meiosis I, or secondary oocytes, in which case they are positioned to go through or are going through meiosis II.

By "meiosis" it is meant the cell cycle events that result in the production of gametes. In the first meiotic cell cycle, or meiosis I, a cell's chromosomes are duplicated and partitioned into two daughter cells. These daughter cells then divide in a second meiotic cell cycle, or meiosis II, that is not accompanied by DNA synthesis, resulting in gametes with a haploid number of chromosomes.

By the "germinal vesicle" stage it is meant the stage of a primary oocyte's maturation that correlates with prophase I of the meiosis I cell cycle, i.e. prior to the first division of the nuclear material. Oocytes in this stage are also called "germinal vesicle oocytes", for the characteristically large nucleus, called a germinal vesicle. In a normal human oocyte cultured in vitro, germinal vesicle occurs about 6-24 hours after the start of maturation.

By the "metaphase I" stage it is meant the stage of a primary oocyte's maturation that correlates with metaphase I of the meiosis I cell cycle. In comparison to germinal vesicle oocytes, metaphase I oocytes do not have a large, clearly defined nucleus. In a normal human oocyte cultured in vitro, metaphase I occurs about 12-36 hours after the start of maturation.

By the "metaphase II" stage it is meant the stage of a secondary oocyte's maturation that correlates with metaphase II of the meiosis II cell cycle. Metaphase II is distinguishable by the extrusion of the first polar body. In a normal human oocyte cultured in vitro, metaphase II occurs about 24-48 hours after the start of maturation By a "mitotic cell cycle", it is meant the events in a cell that result in the duplication of a cell's chromosomes and the division of those chromosomes and a cell's cytoplasmic matter into two daughter cells. The mitotic cell cycle is divided into two phases: interphase and mitosis. In interphase, the cell grows and replicates its DNA. In mitosis, the cell initiates and completes cell division, first partitioning its nuclear material, and then dividing its cytoplasmic material and its partitioned nuclear material (cytokinesis) into two separate cells.

By a "first mitotic cell cycle" or "cell cycle 1" it is meant the time interval from fertilization to the completion of the first cytokinesis event, i.e. the division of the fertilized oocyte into two daughter cells. In instances in which oocytes are fertilized in vitro, the time interval between the injection of human chorionic gonadotropin (HCG) (usually administered prior to oocyte retrieval) to the completion of the first cytokinesis event may be used as a surrogate time interval.

By a "second mitotic cell cycle" or "cell cycle 2" it is meant the second cell cycle event observed in an embryo, the time interval between the production of daughter cells from a fertilized oocyte by mitosis and the production of a first set of granddaughter cells from one of those daughter cells (the "leading daughter cell", or daughter cell A) by mitosis. Upon completion of cell cycle 2, the embryo consists of 3 cells. In other words, cell cycle 2 can be visually identified as the time between the embryo containing 2-cells and the embryo containing 3-cells.

By a "third mitotic cell cycle" or "cell cycle 3" it is meant the third cell cycle event observed in an embryo, typically the time interval from the production of daughter cells from a fertilized oocyte by mitosis and the production of a second set of granddaughter cells from the second daughter cell (the "lagging daughter cell" or daughter cell B) by mitosis. Upon completion of cell cycle 3, the embryo consists of 4 cells. In other words, cell cycle 3 can be visually identified as the time between the embryo containing 3-cells and the embryo containing 4-cells.

By "first cleavage event", it is meant the first division, i.e. the division of the oocyte into two daughter cells, i.e. cell cycle 1. Upon completion of the first cleavage event, the embryo consists of 2 cells.

By "second cleavage event", it is meant the second set of divisions, i.e. the division of leading daughter cell into two granddaughter cells and the division of the lagging daughter cell into two granddaughter cells. In other words, the second cleavage event consists of both cell cycle 2 and cell cycle 3. Upon completion of second cleavage, the embryo consists of 4 cells.

By "third cleavage event", it is meant the third set of divisions, i.e. the divisions of all of the granddaughter cells. Upon completion of the third cleavage event, the embryo typically consists of 8 cells.

Figure 4:
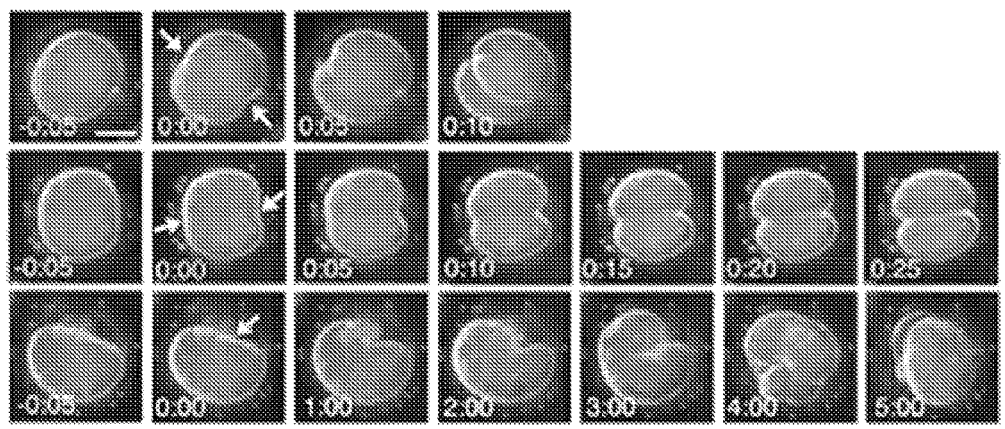
FIG. 4 is a series of three different embryos being followed for the times indicated.

By "cytokinesis" or "cell division" it is meant that phase of mitosis in which a cell undergoes cell division. In other words, it is the stage of mitosis in which a cell's partitioned nuclear material and its cytoplasmic material are divided to produce two daughter cells. The period of cytokinesis is identifiable as the period, or window, of time between when a constriction of the cell membrane (a "cleavage furrow") is first observed and the resolution of that constriction event, i.e. the generation of two daughter cells. The initiation of the cleavage furrow may be visually identified as the point in which the curvature of the cell membrane changes from convex (rounded outward) to concave (curved inward with a dent or indentation). This is illustrated in FIG. 4 top panel by white arrows pointing at 2 cleavage furrows. The onset of cell elongation may also be used to mark the onset of cytokinesis, in which case the period of cytokinesis is defined as the period of time between the onset of cell elongation and the resolution of the cell division.

By "first cytokinesis" or "cytokinesis 1" it is meant the first cell division event after fertilization, i.e. the division of a fertilized oocyte to produce two daughter cells. First cytokinesis usually occurs about one day after fertilization.

By "second cytokinesis" or "cytokinesis 2", it is meant the second cell division event observed in an embryo, i.e. the division of a daughter cell of the fertilized oocyte (the "leading daughter cell", or daughter A) into a first set of two granddaughters.

By "third cytokinesis" or "cytokinesis 3", it is meant the third cell division event observed in an embryo, i.e. the division of the other daughter of the fertilized oocyte (the "lagging daughter cell", or daughter B) into a second set of two granddaughters.

The term "fiduciary marker" or "fiducial marker," is an object used in the field of view of an imaging system which appears in the image produced, for use as a point of reference or a measure. It may be either something placed into or on the imaging subject, or a mark or set of marks in the reticle of an optical instrument.

The term "micro-well" refers to a container that is sized on a cellular scale, preferably to provide for accommodating a single eukaryotic cell.

Pluripotent Cells and Embryos of Interest

In methods of the invention, one or more embryos or pluripotent cells is assessed for its developmental potential by measuring one or more cellular parameters of the embryo(s) or pluripotent cell(s) and employing these measurements to determine the developmental potential of the embryo(s) or pluripotent cell(s). The information thus derived may be used to guide clinical decisions, e.g. whether or not to transfer an in vitro fertilized embryo, whether or not to transplant a cultured cell or cells.

Examples of embryos that may be assessed by the methods of the invention include 1-cell embryos (also referred to as zygotes), 2-cell embryos, 3-cell embryos, 4-cell embryos, 5-cell embryos, 6-cell embryos, 8-cell embryos, etc. typically up to and including 16-cell embryos, any of which may be derived by any convenient manner, e.g. from an oocyte that has matured in vivo or from an oocyte that has matured in vitro.

Examples of pluripotent cells that may be assessed by the methods of the invention include totipotent stem cells, e.g. oocytes, such as primary oocytes and secondary oocytes; pluripotent stem cells, e.g. ES cells, EG cells, iPS cells, and the like; multipotent cells, e.g. mesenchymal stem cells; and tissue-specific stem cells. They may be from any stage of life, e.g. embryonic, neonatal, a juvenile or adult, and of either sex, i.e. XX or XY.

Embryos and pluripotent cells may be derived from any organism, e.g. any mammalian species, e.g. human, primate, equine, bovine, porcine, canine, feline, etc. Preferable, they are derived from a human. They may be previously frozen, e.g. embryos cryopreserved at the 1-cell stage and then thawed, or frozen and thawed oocytes and stem cells. Alternatively, they may be freshly prepared, e.g., embryos that are freshly prepared from oocytes by in vitro fertilization techniques; oocytes that are freshly harvested and/or freshly matured through in vitro maturation techniques or that are derived from pluripotent stem cells differentiated in vitro into germ cells and matured into oocytes; stem cells freshly prepared from the dissociation and culturing of tissues by methods known in the art; and the like. They may be cultured under any convenient conditions known in the art to promote survival, growth, and/or development of the sample to be assessed, e.g. for embryos, under conditions such as those used in the art of in vitro fertilization; see, e.g., U.S. Pat. No. 6,610,543, U.S. Pat. No. 6,130,086, U.S. Pat. No. 5,837,543, the disclosures of which are incorporated herein by reference; for oocytes, under conditions such as those used in the art to promote oocyte maturation; see, e.g., U.S. Pat. No. 5,882,928 and U.S. Pat. No. 6,281,013, the disclosures of which are incorporated herein by reference; for stem cells under conditions such as those used in the art to promote proliferation, see, e.g. U.S. Pat. No. 6,777,233, U.S. Pat. No. 7,037,892, U.S. Pat. No. 7,029,913, U.S. Pat. No. 5,843,780, and U.S. Pat. No. 6,200,806, US Application No. 2009/0047263; US Application No. 2009/0068742, the disclosures of which are incorporated herein by reference. Often, the embryos/pluripotent cells are cultured in a commercially available medium such as KnockOut DMEM, DMEM-F12, or Iscoves Modified Dulbecco's Medium that has been supplemented with serum or serum substitute, amino acids, and growth factors tailored to the needs of the particular embryo/pluripotent cell being assessed.

Time-Lapse Imaging Analysis

In some embodiments, the embryos/pluripotent cells are assessed by measuring cell parameters by time-lapse imaging. The embryos/pluripotent cells may be cultured in standard culture dishes. Alternatively, the embryos/pluripotent cells may be cultured in custom culture dishes, e.g. custom culture dishes with optical quality micro-wells as described herein. In such custom culture dishes, each micro-well holds a single embryo/pluripotent cell, and the bottom surface of each micro-well has an optical quality finish such that the entire group of embryos within a single dish can be imaged simultaneously by a single miniature microscope with sufficient resolution to follow the cell mitosis processes. The entire group of micro-wells shares the same media drop in the culture dish, and can also include an outer wall positioned around the micro-wells for stabilizing the media drop, as well as fiducial markers placed near the micro-wells. The hydrophobicity of the surface can be adjusted with plasma etching or another treatment to prevent bubbles from forming in the micro-wells when filled with media. Regardless of whether a standard culture dish or a custom culture dish is utilized, during culture, one or more developing embryos may be cultured in the same culture medium, e.g. between 1 and 30 embryos may be cultured per dish.

Images are acquired over time, and are then analyzed to arrive at measurements of the one or more cellular parameters. Time-lapse imaging may be performed with any computer-controlled microscope that is equipped for digital image storage and analysis, for example, inverted microscopes equipped with heated stages and incubation chambers, or custom built miniature microscope arrays that fit inside a conventional incubator. The array of miniature microscopes enables the concurrent culture of multiple dishes of samples in the same incubator, and is scalable to accommodate multiple channels with no limitations on the minimum time interval between successive image capture. Using multiple microscopes eliminates the need to move the sample, which improves the system accuracy and overall system reliability. The individual microscopes in the incubator can be partially or fully isolated, providing each culture dish with its own controlled environment. This allows dishes to be transferred to and from the imaging stations without disturbing the environment of the other samples.

The imaging system for time-lapse imaging may employ brightfield illumination, darkfield illumination, phase contrast, Hoffman modulation contrast, differential interference contrast, or fluorescence. In some embodiments, darkfield illumination may be used to provide enhanced image contrast for subsequent feature extraction and image analysis. In addition, red or near-infrared light sources may be used to reduce phototoxicity and improve the contrast ratio between cell membranes and the inner portion of the cells.

Images that are acquired may be stored either on a continuous basis, as in live video, or on an intermittent basis, as in time lapse photography, where a subject is repeatedly imaged in a still picture. Preferably, the time interval between images should be between 1 to 30 minutes in order to capture significant morphological events as described below. In an alternative embodiment, the time interval between images could be varied depending on the amount of cell activity. For example, during active periods images could be taken as often as every few seconds or every minute, while during inactive periods images could be taken every 10 or 15 minutes or longer. Real-time image analysis on the captured images could be used to detect when and how to vary the time intervals. In our methods, the total amount of light received by the samples is estimated to be equivalent to approximately 24 minutes of continuous low-level light exposure for 5-days of imaging. The light intensity for a time-lapse imaging systems is significantly lower than the light intensity typically used on an assisted reproduction microscope due to the low-power of the LEDs (for example, using a 1 W LED compared to a typical 100 W Halogen bulb) and high sensitivity of the camera sensor. Thus, the total amount of light energy received by an embryo using the time-lapse imaging system is comparable to or less than the amount of energy received during routine handling at an IVF clinic. In addition, exposure time can be significantly shortened to reduce the total amount of light exposure to the embryo/pluripotent cell. For 2-days of imaging, with images captured every 5 minutes at 0.5 seconds of light exposure per image, the total amount of low-level light exposure is less than 5 minutes.

Following image acquisition, the images are extracted and analyzed for different cellular parameters, for example, cell size, thickness of the zona pellucida, degree of fragmentation, symmetry of daughter cells resulting from a cell division, time intervals between the first few mitoses, and duration of cytokinesis.

Cell parameters that may be measured by time-lapse imaging are usually morphological events. For example, in assessing embryos, time-lapse imaging may be used to measure the duration of a cytokinesis event, e.g. cytokinesis 1, cytokinesis 2, cytokinesis 3, or cytokinesis 4, where the duration of a cytokinesis event is defined as the time interval between the first observation of a cleavage furrow (the initiation of cytokinesis) and the resolution of the cleavage furrow into two daughter cells (i.e. the production of two daughter cells). Another parameter of interest is the duration of a cell cycle event, e.g. cell cycle 1, cell cycle 2, cell cycle 3, or cell cycle 4, where the duration of a cell cycle event is defined as the time interval between the production of a cell (for cell cycle 1, the fertilization of an ovum; for later cell cycles, at the resolution of cytokinesis) and the production of two daughter cells from that cell. Other cell parameters of interest that can be measured by time-lapse imaging include time intervals that are defined by these cellular events, e.g. (a) the time interval between cytokinesis 1 and cytokinesis 2, definable as any one of the interval between initiation of cytokinesis 1 and the initiation of cytokinesis 2, the interval between the resolution of cytokinesis 1 and the resolution of cytokinesis 2, the interval between the initiation of cytokinesis 1 and the resolution of cytokinesis 2; or the interval between the resolution of cytokinesis 1 and the initiation of cytokinesis 2; or (b) the time interval between cytokinesis 2 and cytokinesis 3, definable as any one of the interval between the initiation of cytokinesis 2 and the initiation of cytokinesis 3, or the interval between resolution of the cytokinesis 2 and the resolution of cytokinesis 3, or the interval between initiation of cytokinesis 2 and the resolution of cytokinesis 3, or the interval between resolution of cytokinesis 2 and the initiation of cytokinesis 3.

For the purposes of in vitro fertilization, it is considered advantageous that the embryo be transferred to the uterus early in development, e.g. by day 2 or day 3, i.e. up through the 8-cell stage, to reduce embryo loss due to disadvantages of culture conditions relative to the in vitro environment, and to reduce potential adverse outcomes associated with epigenetic errors that may occur during culturing (Katari et al. (2009) Hum Mol. Genet. 18(20):3769-78; Sepúlveda et al. (2009) Fertil Steril. 91(5):1765-70). Accordingly, it is preferable that the measurement of cellular parameters take place within 2 days of fertilization, although longer periods of analysis, e.g. about 36 hours, about 54 hours, about 60 hours, about 72 hours, about 84 hours, about 96 hours, or more, are also contemplated by the present methods.

Examples of cell parameters in a maturing oocyte that may be assessed by time-lapse imaging include, without limitation, changes in morphology of the oocyte membrane, e.g. the rate and extent of separation from the zona pellucida; changes in the morphology of the oocyte nucleus, e.g. the initiation, completion, and rate of germinal vesicle breakdown (GVBD); the rate and direction of movement of granules in the cytoplasm and nucleus; the cytokinesis of oocyte and first polar body and the movement of and/or duration of the extrusion of the first polar body. Other parameters include the duration of cytokinesis of the mature secondary oocyte and the second polar body.

Examples of cell parameters in a stem cell or population of stem cells that may be assessed by time-lapse imaging include, without limitation, the duration of cytokinesis events, time between cytokinesis events, size and shape of the stem cells prior to and during cytokinesis events, number of daughter cells produced by a cytokinesis event, spatial orientation of the cleavage furrow, the rate and/or number of asymmetric divisions observed (i.e. where one daughter cell maintains a stem cell while the other differentiates), the rate and/or number of symmetric divisions observed (i.e. where both daughter cells either remain as stem cells or both differentiate), and the time interval between the resolution of a cytokinesis event and when a stem cell begins to differentiate.

Parameters can be measured manually, or they may be measured automatically, e.g. by image analysis software. When image analysis software is employed, image analysis algorithms may be used that employ a probabilistic model estimation technique based on sequential Monte Carlo method, e.g. generating distributions of hypothesized embryo/pluripotent cell models, simulating images based on a simple optical model, and comparing these simulations to the observed image data. When such probabilistic model estimations are employed, cells may be modeled as any appropriate shape, e.g. as collections of ellipses in 2D space, collections of ellipsoids in 3D space, and the like. To deal with occlusions and depth ambiguities, the method can enforce geometrical constraints that correspond to expected physical behavior. To improve robustness, images can be captured at one or more focal planes.

Gene Expression Analysis

In some embodiments, the embryos or pluripotent cells are assessed by measuring gene expression. In such embodiments, the cell parameter is a gene expression level or gene expression profile. Determining the expression of one or more genes, i.e. obtaining an expression profile or expression evaluation, may be made by measuring nucleic acid transcripts, e.g. mRNAs, of the one or more genes of interest, e.g. a nucleic acid expression profile; or by measuring levels of one or more different proteins/polypeptides that are expression products of one or more genes of interest, e.g. a proteomic expression profile. In other words, the terms "expression profile" and "expression evaluation" are used broadly to include a gene expression profile at the RNA level or protein level.

In some embodiments, expression of genes may be evaluated by obtaining a nucleic acid expression profile, where the amount or level of one or more nucleic acids in the sample is determined, e.g., the nucleic acid transcript of the one or more genes of interest, in these embodiments, the sample that is assayed to generate the expression profile is a nucleic acid sample. The nucleic acid sample includes a plurality or population of distinct nucleic acids that includes the expression information of the genes of interest of the embryo or cell being assessed. The nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as is, amplified, employed to prepare cDNA, cRNA, etc., as is known in the differential expression art. The sample may be prepared from a single cell, e.g. a pluripotent cell of a culture of pluripotent cells of interest, or a single cell (blastomere) from an embryo of interest; or from several cells, e.g. a fraction of a cultures of pluripotent cells, or 2, 3, or 4, or more blastomeres of an embryo of interest, using standard protocols.

The expression profile may be generated from the initial nucleic acid sample using any convenient protocol. While a variety of different manners of generating expression profiles are known, such as those employed in the field of differential gene expression analysis, one representative and convenient type of protocol for generating expression profiles is array-based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively.

Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed. The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptosome), may be both qualitative and quantitative.

Alternatively, non-array based methods for quantitating the level of one or more nucleic acids in a sample may be employed, including those based on amplification protocols, e.g., Polymerase Chain Reaction (PCR)-based assays, including quantitative PCR, reverse-transcription PCR(RT-PCR), real-time PCR, and the like.

In some embodiments, expression of genes may be evaluated by obtaining a proteomic expression profile, where the amount or level of one or more proteins/polypeptides in the sample is determined, e.g., the protein/polypeptide encoded by the gene of interest. In these embodiments, the sample that is assayed to generate the expression profile employed in the methods is a protein sample. Where the expression profile is proteomic expression profile, i.e. a profile of one or more protein levels in a sample, any convenient protocol for evaluating protein levels may be employed wherein the level of one or more proteins in the assayed sample is determined.

While a variety of different manners of assaying for protein levels are known in the art, one representative and convenient type of protocol for assaying protein levels is ELISA. In ELISA and ELISA-based assays, one or more antibodies specific for the proteins of interest may be immobilized onto a selected solid surface, preferably a surface exhibiting a protein affinity such as the wells of a polystyrene microtiter plate. After washing to remove incompletely adsorbed material, the assay plate wells are coated with a non-specific "blocking" protein that is known to be antigenically neutral with regard to the test sample such as bovine serum albumin (BSA), casein or solutions of powdered milk. This allows for blocking of non-specific adsorption sites on the immobilizing surface, thereby reducing the background caused by non-specific binding of antigen onto the surface. After washing to remove unbound blocking protein, the immobilizing surface is contacted with the sample to be tested under conditions that are conducive to immune complex (antigen/antibody) formation. Such conditions include diluting the sample with diluents such as BSA or bovine gamma globulin (BGG) in phosphate buffered saline (PBS)/Tween or PBS/Triton-X 100, which also tend to assist in the reduction of nonspecific background, and allowing the sample to incubate for about 2-4 hrs at temperatures on the order of about 25°-27° C. (although other temperatures may be used). Following incubation, the antisera-contacted surface is washed so as to remove non-immunocomplexed material. An exemplary washing procedure includes washing with a solution such as PBS/Tween, PBS/Triton-X 100, or borate buffer. The occurrence and amount of immunocomplex formation may then be determined by subjecting the bound immunocomplexes to a second antibody having specificity for the target that differs from the first antibody and detecting binding of the second antibody. In certain embodiments, the second antibody will have an associated enzyme, e.g. urease, peroxidase, or alkaline phosphatase, which will generate a color precipitate upon incubating with an appropriate chromogenic substrate. For example, a urease or peroxidase-conjugated anti-human IgG may be employed, for a period of time and under conditions which favor the development of immunocomplex formation (e.g., incubation for 2 hr at room temperature in a PBS-containing solution such as PBS/Tween). After such incubation with the second antibody and washing to remove unbound material, the amount of label is quantified, for example by incubation with a chromogenic substrate such as urea and bromocresol purple in the case of a urease label or 2,2'-azino-di-(3-ethyl-benzothiazoline)-6-sulfonic acid (ABTS) and $H_2O_2$, in the case of a peroxidase label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The solid substrate upon which the antibody or antibodies are immobilized can be made of a wide variety of materials and in a wide variety of shapes, e.g., microtiter plate, microbead, dipstick, resin particle, etc. The substrate may be chosen to maximize signal to noise ratios, to minimize background binding, as well as for ease of separation and cost. Washes may be effected in a manner most appropriate for the substrate being used, for example, by removing a bead or dipstick from a reservoir, emptying or diluting a reservoir such as a microtiter plate well, or rinsing a bead, particle, chromatographic column or filter with a wash solution or solvent.

Alternatively, non-ELISA based-methods for measuring the levels of one or more proteins in a sample may be employed. Representative examples include but are not limited to mass spectrometry, proteomic arrays, xMAP™ microsphere technology, flow cytometry, western blotting, and immunohistochemistry.

The resultant data provides information regarding expression for each of the genes that have been probed, wherein the expression information is in terms of whether or not the gene is expressed and, typically, at what level, and wherein the expression data may be both qualitative and quantitative.

In generating the expression profile, in some embodiments a sample is assayed to generate an expression profile that includes expression data for at least one gene/protein, sometimes a plurality of genes/proteins, where by plurality is meant at least two different genes/proteins, and often at least about 3, typically at least about 10 and more usually at least about 15 different genes/proteins or more, such as 50 or more, or 100 or more, etc.

In the broadest sense, the expression evaluation may be qualitative or quantitative. As such, where detection is qualitative, the methods provide a reading or evaluation, e.g., assessment, of whether or not the target analyte, e.g., nucleic acid or expression product, is present in the sample being assayed. In yet other embodiments, the methods provide a quantitative detection of whether the target analyte is present in the sample being assayed, i.e., an evaluation or assessment of the actual amount or relative abundance of the target analyte, e.g., nucleic acid or protein in the sample being assayed. In such embodiments, the quantitative detection may be absolute or, if the method is a method of detecting two or more different analytes, e.g., target nucleic acids or protein, in a sample, relative. As such, the term "quantifying" when used in the context of quantifying a target analyte, e.g., nucleic acid(s) or protein(s), in a sample can refer to absolute or to relative quantification. Absolute quantification may be accomplished by inclusion of known concentration(s) of one or more control analytes and referencing, i.e. normalizing, the detected level of the target analyte with the known control analytes (e.g., through generation of a standard curve). Alternatively, relative quantification can be accomplished by comparison of detected levels or amounts between two or more different target analytes to provide a relative quantification of each of the two or more different analytes, e.g., relative to each other.

Examples of genes whose expression levels are predictive of zygote developmental potential include Cofillin (NM_005507), DIAPH1 (NM_001079812, NM_005219), ECT2 (NM_018098), MYLC2/MYL5 (NM_002477), DGCR8 (NM_022720), Dicer/DICER1 (NM_030621, NM_177438), TARBP2 (NM_004178, NM_134323, NM_134324), CPEB1 (NM_001079533, NM_001079534, NM_001079535, NM_030594), Symplekin/SYMPK (NM_004819), YBX2 (NM_015982), ZAR1 (NM_175619), CTNNB1 (NM_001098209, NM_001098210, NM_001098210, NM_001904), DNMT3B (NM_006892, NM_175848, NM_175849, NM_175850), TERT (NM_198253, NM_198255), YY1 (NM_003403), IFGR2/IFNGR2 (NM_005534), BTF3 (NM_001037637, NM_001207), and NELF (NM_001130969, NM_001130970, NM_001130971, NM_015537). Other genes whose expression levels may serve as cell parameters predictive of embryo developmental potential are provided in FIG. 8. In arriving at a gene expression level measurement, the expression level is often evaluated and then normalized to a standard control, e.g. the expression level in the sample of a gene that is known to be constant through development, e.g. GAPDH or RPLPO, or of a gene whose expression at that timepoint is known.

Gene expression levels may be determined from a single cell, e.g. a blastomere from an embryo of interest, or an isolated oocyte, or an isolated cell from a culture of stem cells, etc., or they may be determined from a embryo, e.g. 2, 3, or 4, or more blastomeres of an embryo of interest, up to and including the whole embryo of interest, or multiple cells from a culture of stem cells, up to and including the whole culture of stem cells, etc.

In other aspects, the present invention comprises a protocol for performing concurrent genotyping and gene expression analysis on a single cell. For embryos, this can be used to improve pre-implantation genetic diagnosis (PGD), a procedure where a single cell is removed from an embryo and its DNA is tested for karyotypic defects or the presence of specific disease genes. Our method allows for concurrent genetic and gene expression analysis. The method involves the following steps: (1) collecting a single cell into a small volume of medium or buffer, (2) performing one-step reverse transcription and polymerase chain reaction (PCR) amplification using a mixture of genotyping and gene expression analysis primers, (3) collecting an aliquot of the amplified cDNA after fewer than 18 cycles of PCR to preserve linearity of the amplification, (4) using the cDNA aliquot to perform gene expression analysis with standard techniques such as quantitative real-time PCR, (5) using the remaining sample to perform a second round of PCR to further amplify the genetic information for genotyping purposes, and (6) genotyping using standard techniques such as gel electrophoresis.

Determining Developmental Potential from Image and/or Gene Expression Analysis

Once cell parameter measurements have been obtained, the measurements are employed to determine the developmental potential of the embryo/pluripotent cell. As discussed above, the terms "developmental potential" and "developmental competence" refer to the ability or capacity of a pluripotent cell or tissue to grow or develop. For example, in the case of an oocyte or embryo, the developmental potential may be the ability or capacity of that oocyte or embryo to grow or develop into a healthy blastocyst. As another example, in the case of a stein cell, the developmental potential is the ability or capacity to grow or develop into one or more cells of interest, e.g. a neuron, a muscle, a B- or T-cell, and the like. In some embodiments, the developmental potential of an oocyte or embryo is the ability or capacity of that oocyte or embryo to develop into a healthy blastocyst; to successfully implant into a uterus; to go through gestation; and/or to be born live. In some embodiments, the developmental potential of a pluripotent cell is the ability or capacity of that pluripotent cell to develop into one or more cells of interest, e.g. a neuron, a muscle, a B- or T-cell, and the like; and/or to contribute to a tissue of interest in vivo.

By "good developmental potential', it is meant that the embryo/pluripotent cell is statistically likely to develop as desired, i.e. it has a 55%, 60%, 70%, 80%, 90%, 95% or more chance, e.g. a 100% chance, of developing as desired. In other words, 55 out of 100, 60 out of 100, 70 out of 100, 80 out of 100, 95 out of 100, 95 out of 100, or 100 out of 100 embryos or pluripotent cells demonstrating the cell parameter measurements used to arrive at the determination of good developmental potential do, in fact, go on to develop as desired. Conversely, by "poor developmental potential' it is meant that the embryo/pluripotent cell is not statistically likely to develop as desired, i.e. it has a 50%, 40%, 30%, 20%, 10%, 5% or less chance, e.g. 0% chance, of developing as desired. In other words, only 50 out of 100, 40 out of 100, 30 out of 100, 20 out of 100, 10 out of 100, or 5 out of 100 or less of the embryos or pluripotent cells demonstrating the cell parameter measurements used to arrive at the determination of poor developmental potential do, in fact, go on to develop as desired. As used herein. "normal' or "healthy' embryos and pluripotent cells demonstrate good developmental potential, whereas "abnormal' embryos and pluripotent cells display poor developmental potential.

In some embodiments, the cell parameter measurement is used directly to determine the developmental potential of the embryo/pluripotent cell. In other words, the absolute value of the measurement itself is sufficient to determine the developmental potential. Examples of this in embodiments using time-lapse imaging to measure cell parameters include, without limitation, the following, any of which alone or in combination are indicative of good developmental potential in a human embryo: (a) a cytokinesis 1 that lasts about 0-30 minutes, for example, about 6-20 minutes, on average about 12-14 minutes; (b) a cell cycle 1 that lasts about 20-27 hours, e.g. about 25-27 hours; (c) a time interval between the resolution of cytokinesis 1 and the onset of cytokinesis 2 that is about 8-15 hours, e.g. about 9-13 hours, with an average value of about 11+/−2.1 hours; (d) a time interval, i.e. synchronicity, between the initiation of cytokinesis 2 and the initiation of cytokinesis 3 that is about 0-5 hours, e.g. about 0-3 hours, with an average time of about 1+/−1.6 hours. Examples of direct measurements, any of which alone or in combination are indicative of poor developmental potential in a human embryo, include without limitation: (a) a cytokinesis 1 that lasts longer than about 30 minutes, for example, about 32, 35, 40, 45, 50, 55, or 60 minutes or more; (b) a cell cycle 1 that lasts longer than about 27 hours, e.g. 28, 29, or 30 or more hours; (c) a time interval between the resolution of cytokinesis 1 and the onset of cytokinesis 2 that last more that 15 hour, e.g. about 16, 17, 18, 19, or 20 or more hours, or less than 8 hours, e.g. about 7, 5, 4, or 3 or fewer hours; (d) a time interval between the initiation of cytokinesis 2 and the initiation of cytokinesis 3 that is 6, 7, 8, 9, or 10 or more hours.

In some embodiments, the cell parameter measurement is employed by comparing it to a cell parameter measurement from a reference, or control, embryo/pluripotent cell, and using the result of this comparison to provide a determination of the developmental potential of the embryo/pluripotent cell. The terms "reference" and "control" as used herein mean a standardized embryo or cell to be used to interpret the cell parameter measurements of a given embryo/pluripotent cell and assign a determination of developmental potential thereto. The reference or control may be an embryo/pluripotent cell that is known to have a desired phenotype, e.g., good developmental potential, and therefore may be a positive reference or control embryo/pluripotent cell. Alternatively, the reference/control embryo/pluripotent cell may be an embryo/pluripotent cell known to not have the desired phenotype, and therefore be a negative reference/control embryo/pluripotent cell.

In certain embodiments, the obtained cell parameter measurement(s) is compared to a comparable cell parameter measurement(s) from a single reference/control embryo/pluripotent cell to obtain information regarding the phenotype of the embryo/cell being assayed. In yet other embodiments, the obtained cell parameter measurement(s) is compared to the comparable cell parameter measurement(s) from two or more different reference/control embryos or pluripotent cells to obtain more in depth information regarding the phenotype of the assayed embryo/cell. For example, the obtained cell parameter measurements from the embryo(s) or pluripotent cell(s) being assessed may be compared to both a positive and negative embryo or pluripotent cell to obtain confirmed information regarding whether the embryo/cell has the phenotype of interest.

As an example, cytokinesis 1 in a normal human embryo, i.e. with good developmental potential, is about 0-30 minutes, more usually about 6-20 minutes, on average about 12-14 minutes, i.e. about 1, 2, 3, 4, or 5 minutes, more usually about 6, 7, 8, 9, 10, 11, 12, 13, 14, 15, 16, 17, 18, 19, or 20 minutes, in some cases 21, 22, 23, 24, 25, 26, 27, 28, 29, or up to about 30 minutes. A longer period of time to complete cytokinesis 1 in the embryo being assessed as compared to that observed for a normal reference embryo is indicative of poor developmental potential. As a second example, cell cycle 1 in a normal embryo, i.e. from the time of fertilization to the completion of cytokinesis 1, is typically completed in about 20-27 hours, more usually in about 25-27 hours, i.e. about 15, 16, 17, 18, or 19 hours, more usually about 20, 21, 22, 23, or 24 hours, and more usually about 25, 26 or 27 hours. A cell cycle 1 that is longer in the embryo being assessed as compared to that observed for a normal reference embryo is indicative of poor developmental potential. As a third example, the resolution of cytokinesis 1 and the onset of cytokinesis 2 in normal human embryos is about 8-15 hours, more often about 9-13 hours, with an average value of about 11+/−2.1 hours; i.e. 6, 7, or 8 hours, more usually about 9, 10, 11, 12, 13, 14 or up to about 15 hours. A longer or shorter cell cycle 2 in the embryo being assessed as compared to that observed for a normal reference embryo is indicative of poor developmental potential. As a fourth example, the time interval between the initiation of cytokinesis 2 and the initiation of cytokinesis 3, i.e. the synchronicity of the second and third mitosis, in normal human embryos is usually about 0-5 hours, more usually about 0, 1, 2 or 3 hours, with an average time of about 1+/−1.6 hours; a longer interval between the completion of cytokinesis 2 and cytokinesis 3 in the embryo being assessed as compared to that observed in a normal reference embryo is indicative of poor developmental potential. Finally, as an example of how this embodiment may be applied when using gene expression levels as parameters for assessing developmental potential, lower expression levels of Cofillin, DIAPH1, ECT2, MYLC2, DGCR8, Dicer, TARBP2, CPEB1, Symplekin, YBX2, ZAR1, CTNNB1, DNMT3B, TERT, YY1, IFGR2, BTF3 and/or NELF, i.e. 1.5-fold, 2-fold, 3-fold, 4-fold, 5-fold, 10-fold, 20-fold, 50-fold, or 100-fold lower expression, in 2-cell embryos being assessed as compared to that observed for a normal reference 2-cell embryo is indicative of poor developmental potential, whereas expression that is equal to or greater than that observed for a normal reference 2-cell embryo is indicative of good developmental potential. Other examples may be derived from empirical data, e.g. by observing one or more reference embryos or pluripotent cells alongside the embryo/pluripotent cell to be assessed. Any reference embryo/pluripotent cell may be employed, e.g. a normal reference sample with good developmental potential, or an abnormal reference sample with poor developmental potential. In some cases, more than one reference sample may be employed, e.g. both a normal reference sample and an abnormal reference sample may be used.

In some embodiments, it may be desirable to use cell parameter measurements that are arrived at by time-lapse microscopy or by expression profiling, but not by both time-lapse microscopy and expression profiling. In other embodiments, it may be desirable to use cell parameter measurements that are arrived at by time-lapse microscopy as well as cell parameter measurements that are arrived at by expression profiling.

As discussed above, one or more parameters may be measured and employed to determine the developmental potential of an embryo or pluripotent cell. In some embodiments, a measurement of a single parameter may be sufficient to arrive at a determination of developmental potential. In some embodiments, it may be desirable to employ measurements of more than one parameter, for example, 2 cell parameters, 3 cell parameters, or 4 or more cell parameters.

In certain embodiments, assaying for multiple parameters may be desirable as assaying for multiple parameters may provide for greater sensitivity and specificity. By sensitivity it is meant the proportion of actual positives which are correctly identified as being such. This may be depicted mathematically as:

$$\text{Sensitivity} = \frac{(\text{Number of true positives})}{(\text{Number of true positives} + \text{Number of false negatives})}$$

Thus, in a method in which "positives" are the embryos that have good developmental potential, i.e. that will develop into blastocysts, and "negatives" are the embryos that have poor developmental potential, i.e. that will not develop into blastocysts, a sensitivity of 100% means that the test recognizes all embryos that will develop into blastocysts as such. In some embodiments, the sensitivity of the assay may be about 70%, 80%, 90%, 95%, 98% or more, e.g. 100%. By specificity it is meant the proportion of negatives which are correctly identified as such. This may be depicted mathematically as $$\text{Specificity} = \frac{(\text{Number of true positives})}{(\text{Number of true negatives} + \text{Number of false positives})}$$

Thus, in a method in which positives are the embryos that have good developmental potential, i.e. that will develop into blastocysts, and negatives are the embryos that have poor developmental potential, i.e. that will not develop into blastocysts, a specificity of 100% means that the test recognizes all embryos that will not develop into blastocysts, i.e. will arrest prior to the blastocyst stage, as such. In some embodiments, the specificity of the assay may be about 70%, 80%, 90%, 95%, 98% or more, e.g. 100%.

Figure 7:
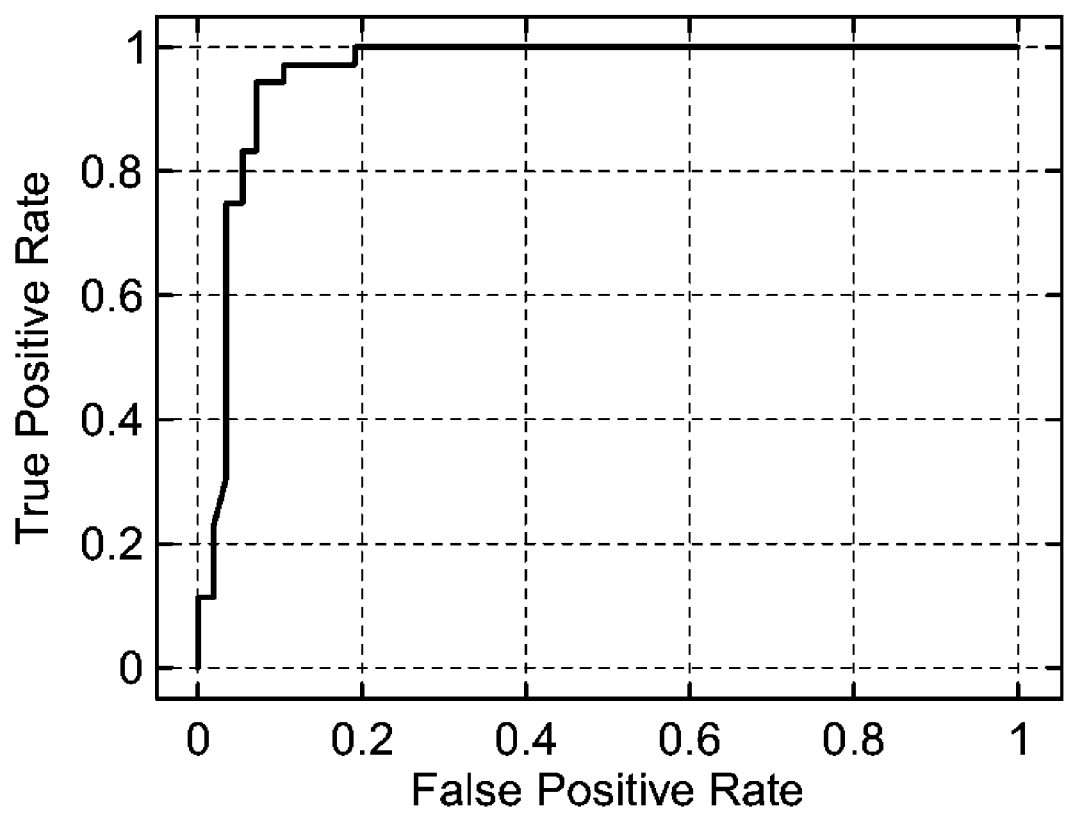
FIG. 7 is a graph showing a receiver operating characteristic (ROC) curve for predicting blastocyst formation using the 3 dynamic morphological parameters.

As demonstrated in the examples sections below and in FIG. 7, the use of three parameters provides sensitivity of 94% and specificity of 93% with a cutoff point of 3 times the standard deviations of the blastocyst distribution. In other words, methods of the invention are able to correctly identify the number of embryos that are going to develop into blastocysts 94% of the time (sensitivity), and the number of embryos that are going to arrest before the blastocyst stage 93% of the time (specificity). In addition, the specified mean values and/or cut-off points may be modified depending upon the data set used to calculate these values as well as the specific application.

In some embodiments, the assessment of an embryo or pluripotent cell includes generating a written report that includes the artisan's assessment of the subject embryo/pluripotent cell, e.g. a "developmental potential assessment", an "assessment of chromosomal abnormalities", etc. Thus, a subject method may further include a step of generating or outputting a report providing the results of such an assessment, which report can be provided, in the form of an electronic medium (e.g., an electronic display on a computer monitor), or in the form of a tangible medium (e.g., a report printed on paper or other tangible medium).

A "report," as described herein, is an electronic or tangible document which includes report elements that provide information of interest relating to an assessment arrived at by methods of the invention. A subject report can be completely or partially electronically generated. A subject report includes at least an assessment of the developmental potential of the subject embryo or pluripotent cell, an assessment of the probability of the existence of chromosomal abnormalities, etc. A subject report can further include one or more of: 1) information regarding the testing facility; 2) service provider information; 3) subject data; 4) sample data; 5) a detailed assessment report section, providing information relating to how the assessment was arrived at, e.g. a) cell parameter measurements taken, b) reference values employed, if any; and 6) other features.

The report may include information about the testing facility, which information is relevant to the hospital, clinic, or laboratory in which sample gathering and/or data generation was conducted. Sample gathering can include how the sample was generated, e.g. how it was harvested from a subject, and/or how it was cultured etc. Data generation can include how images were acquired or gene expression profiles were analyzed. This information can include one or more details relating to, for example, the name and location of the testing facility, the identity of the lab technician who conducted the assay and/or who entered the input data, the date and time the assay was conducted and/or analyzed, the location where the sample and/or result data is stored, the lot number of the reagents (e.g., kit, etc.) used in the assay, and the like. Report fields with this information can generally be populated using information provided by the user.

The report may include information about the service provider, which may be located outside the healthcare facility at which the user is located, or within the healthcare facility. Examples of such information can include the name and location of the service provider, the name of the reviewer, and where necessary or desired the name of the individual who conducted sample preparation and/or data generation. Report fields with this information can generally be populated using data entered by the user, which can be selected from among pre-scripted selections (e.g., using a drop-down menu). Other service provider information in the report can include contact information for technical information about the result and/or about the interpretive report.

The report may include a subject data section, including medical history of subjects from which oocytes or pluripotent cells were harvested, patient age, in vitro fertilization cycle characteristics (e.g. fertilization rate, day 3 follicle stimulating hormone (FSH) level), and, when oocytes are harvested, zygote/embryo cohort parameters (e.g. total number of embryos). This subject data may be integrated to improve embryo assessment and/or help determine the optimal number of embryos to transfer. The report may also include administrative subject data (that is, data that are not essential to the assessment of developmental potential) such as information to identify the subject (e.g., name, subject date of birth (DOB), gender, mailing and/or residence address, medical record number (MRN), room and/or bed number in a healthcare facility), insurance information, and the like), the name of the subject's physician or other health professional who ordered the assessment of developmental potential and, if different from the ordering physician, the name of a staff physician who is responsible for the subject's care (e.g., primary care physician).

The report may include a sample data section, which may provide information about the biological sample analyzed in the assessment, such as the type of sample (embryo or pluripotent cell, and type of pluripotent cell), how the sample was handled (e.g. storage temperature, preparatory protocols) and the date and time collected. Report fields with this information can generally be populated using data entered by the user, some of which may be provided as pre-scripted selections (e.g., using a drop-down menu).

The report may include an assessment report section, which may include information relating to how the assessments/determinations were arrived at as described herein. The interpretive report can include, for example, time-lapse images of the embryo or pluripotent cell being assessed, and/or gene expression results. The assessment portion of the report can optionally also include a recommendation(s) section. For example, where the results indicate good developmental potential of an embryo, the recommendation can include a recommendation that a limited number of embryos be transplanted into the uterus during fertility treatment as recommended in the art.

It will also be readily appreciated that the reports can include additional elements or modified elements. For example, where electronic, the report can contain hyperlinks which point to internal or external databases which provide more detailed information about selected elements of the report. For example, the patient data element of the report can include a hyperlink to an electronic patient record, or a site for accessing such a patient record, which patient record is maintained in a confidential database. This latter embodiment may be of interest in an in-hospital system or in-clinic setting. When in electronic format, the report is recorded on a suitable physical medium, such as a computer readable medium, e.g., in a computer memory, zip drive, CD, DVD, etc.

It will be readily appreciated that the report can include all or some of the elements above, with the proviso that the report generally includes at least the elements sufficient to provide the analysis requested by the user (e.g., an assessment of developmental potential).

Utility

As discussed above, methods of the invention may be used to assess embryos or pluripotent cells to determine their developmental potential. This determination of developmental potential may be used to guide clinical decisions and/or actions. For example, in order to increase pregnancy rates, clinicians often transfer multiple embryos into patients, potentially resulting in multiple pregnancies that pose health risks to both the mother and fetuses. Using results obtained from the methods of the invention, the developmental potential of embryos being transferred to develop into fetuses is determined prior to transplantation, allowing the practitioner to decide how many embryos to transfer so as to maximize the chance of success of a full term pregnancy while minimizing risk.

Assessments made by following methods of the invention may also find use in ranking embryos or pluripotent cells in a group of embryos or pluripotent cells for their developmental potential. For example, in some instances, multiple embryos may be capable of developing into blastocysts, i.e. will have good developmental potential. However, some embryos will be more likely to achieve the blastocysts stage or a higher-quality blastocyst than other, i.e. they will have better developmental potential than other embryos. In such cases, methods of the invention may be used to rank the embryos in the group. In such methods, one or more cell parameters for each embryo/pluripotent cell is measured to arrive at a cell parameter measurement for each embryo/pluripotent cell. The one or more cell parameter measurements from each of the embryos or pluripotent cells are then employed to determine the developmental potential of the embryos or pluripotent cells relative to one another. In some embodiments, the cell parameter measurements from each of the embryos or pluripotent cells are employed by comparing them directly to one another to determine the developmental potential of the embryos or pluripotent cells. In some embodiments, the cell parameter measurements from each of the embryos or pluripotent cells are employed by comparing the cell parameter measurements to a cell parameter measurement from a reference embryo/pluripotent cell to determine the developmental potentials for each embryo/pluripotent cell, and then comparing the determined developmental potentials for each embryo/pluripotent cell to determine the developmental potential of the embryos or pluripotent cells relative to one another. In this way, a practitioner assessing, for example, multiple zygotes/embryos, can choose only the best quality embryos, i.e. those with the best developmental potential, to transfer so as to maximize the chance of success of a full term pregnancy while minimizing risk.

Assessments made by following the methods of the invention may also find use in determining the developmental potential of oocytes that are matured in vitro and stem cells that are cultured in vitro. Information on the developmental potential of oocytes obtained by the methods of the invention can guide the practitioner's selection of oocytes to fertilize, resulting in higher probability of success in deriving blastocysts from these oocytes. Likewise, information on the developmental potential of stem cells can inform the practitioner's selection of stem cells to use in procedures to, e.g. reconstitute or replace a tissue in vivo in a subject in need thereof.

Reagents, Devices and Kits

Also provided are reagents, devices and kits thereof for practicing one or more of the above-described methods. The subject reagents, devices and kits thereof may vary greatly. Reagents and devices of interest include those mentioned above with respect to the methods of measuring any of the aforementioned cell parameters, where such reagents may include culture plates, culture media, microscopes, imaging software, imaging analysis software, nucleic acid primers, arrays of nucleic acid probes, antibodies, signal producing system reagents, etc., depending on the particular measuring protocol to be performed. For example, reagents may include PCR primers that are specific for one or more of the genes Cofilin, DIAPH1, ECT2, MYLC2/MYL5, DGCR8, Dicer/DICER1, TARBP2, CPEB1, Symplekin/SYMPK, YBX2, ZAR1, CTNNB1, DNMT3B, TERT, YY1, IFGR2/IFNGR2, BTF3, and NELF, as described above. Other examples of reagents include arrays that comprise probes that are specific for one or more of the genes of interest, or antibodies to the proteins encoded by these genes of interest.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, diskette, CD, etc., on which the information has been recorded. Yet another means that may be present is a website address which may be used via the internet to access the information at a removed site. Any convenient means may be present in the kits.

Automated Cell Imaging with a Microscope Array

Some of the methods described above require the ability to observe embryo and stem cell development via time-lapse imaging. This can be achieved using a system comprised of a miniature, multi-channel microscope array that can fit inside a standard incubator. This allows multiple samples to be imaged quickly and simultaneously without having to physically move the dishes. One illustrative prototype, shown in FIG. 22, consists of a 3-channel microscope array with dark-field illumination, although other types of illumination could be used. By "three channel," it is meant that there are three independent microscopes imaging three distinct culture dishes simultaneously. A stepper motor is used to adjust the focal position for focusing or acquiring 3D image stacks. White-light LEDs are used for illumination, although we have observed that for human embryos, using red or near-infrared (IR) LEDs can improve the contrast ratio between cell membranes and the inner portions of the cells. This improved contrast ratio can help with both manual and automated image analysis. In addition, moving to the infrared region can reduce phototoxicity to the samples. Images are captured by low-cost, high-resolution webcams, but other types of cameras may be used.

Figure 22:
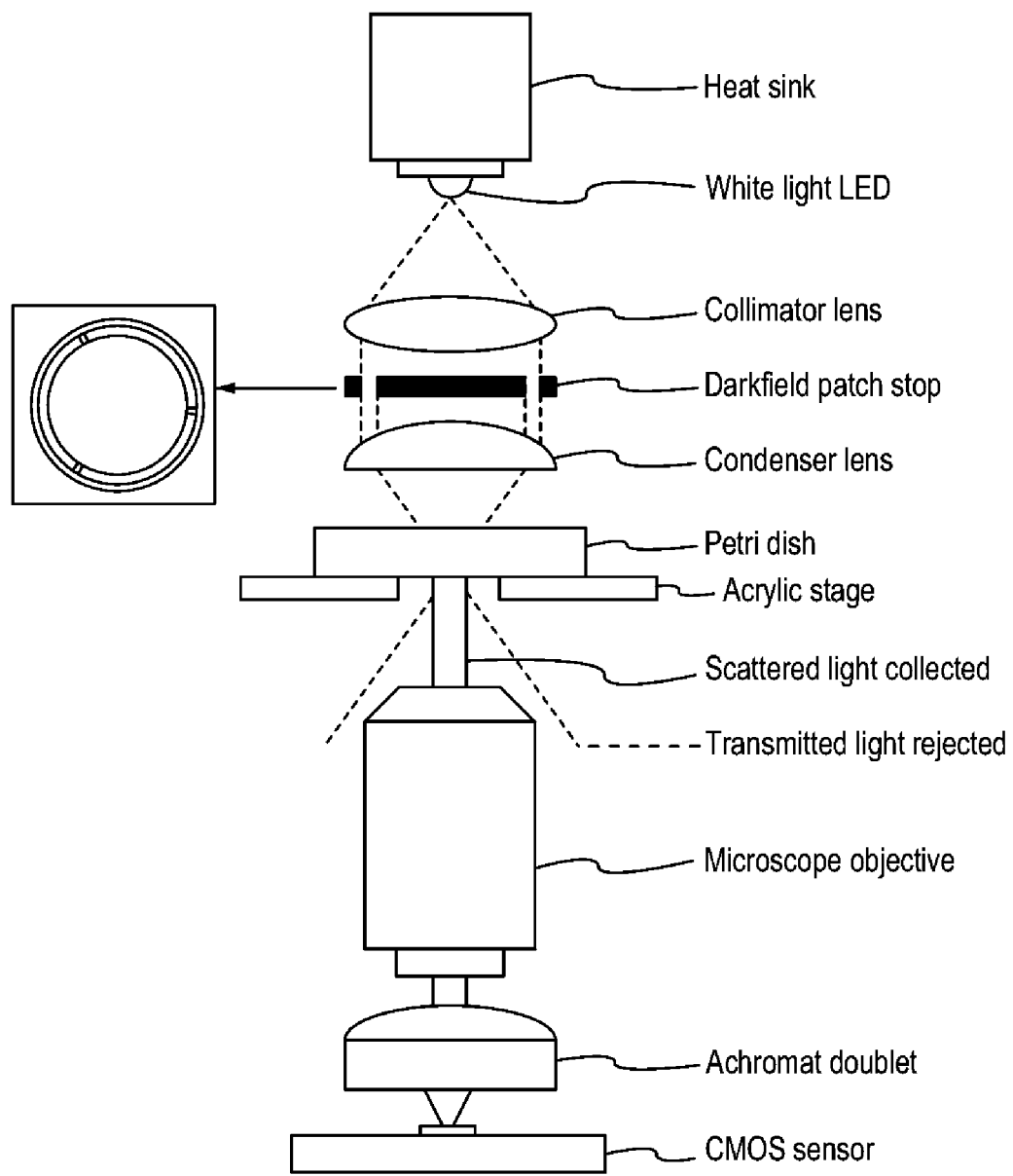
FIG. 22 is a schematic drawing of a dark field microscope according to the present invention; the inset on the left shows a laser machined darkfield patch set up.

As shown in FIG. 22, each microscope of the prototype system described above is used to image a culture dish which may contain anywhere from 1-30 embryos. The microscope collects light from a white light LED connected to a heat sink to help dissipate any heat generated by the LED, which is very small for brief exposure times. The light passes through a conventional dark field patch for stopping direct light, through a condenser lens and onto a specimen labeled "petri dish," which is a culture dish holding the embryos being cultured and studied. The culture dish may have wells that help maintain the order of the embryos and keep them from moving while the dish is being carried to and from the incubator. The wells can be spaced close enough together so that embryos can share the same media drop. The scattered light is then passed through a microscope objective, then through an achromat doublet, and onto a CMOS sensor. The CMOS sensor acts as a digital camera and is connected to a computer for image analysis and tracking as described above.

This design is easily scalable to provide significantly more channels and different illumination techniques, and can be modified to accommodate fluidic devices for feeding the samples. In addition, the design can be integrated with a feedback control system, where culture conditions such as temperature, $CO_2$ (to control pH), and media are optimized in real-time based on feedback and from the imaging data. This system was used to acquire time-lapse videos of human embryo development, which has utility in determining embryo viability for in vitro fertilization (IVF) procedures. Other applications include stem cell therapy, drug screening, and tissue engineering.

In one embodiment of the device, illumination is provided by a Luxeon white light-emitting diode (LED) mounted on an aluminum heat sink and powered by a BuckPuck current regulated driver. Light from the LED is passed through a collimating lens. The collimated light then passes through a custom laser-machined patch stop, as shown in FIG. 22, and focused into a hollow cone of light using an aspheric condenser lens. Light that is directly transmitted through the sample is rejected by the objective, while light that is scattered by the sample is collected. In one embodiment, Olympus objectives with 20× magnification are used, although smaller magnifications can be used to increase the field-of-view, or larger magnifications can be used to increase resolution. The collected light is then passed through an achromat doublet lens (i.e. tube lens) to reduce the effects of chromatic and spherical aberration. Alternatively, the collected light from the imaging objective can be passed through another objective, pointed in the opposing direction, that acts as a replacement to the tube lens. In one configuration, the imaging objective can be a 10× objective, while the tube-lens objective can be a 4× objective. The resulting image is captured by a CMOS sensor with 2 megapixel resolution (1600×1200 pixels). Different types of sensors and resolutions can also be used.

Figure 23:
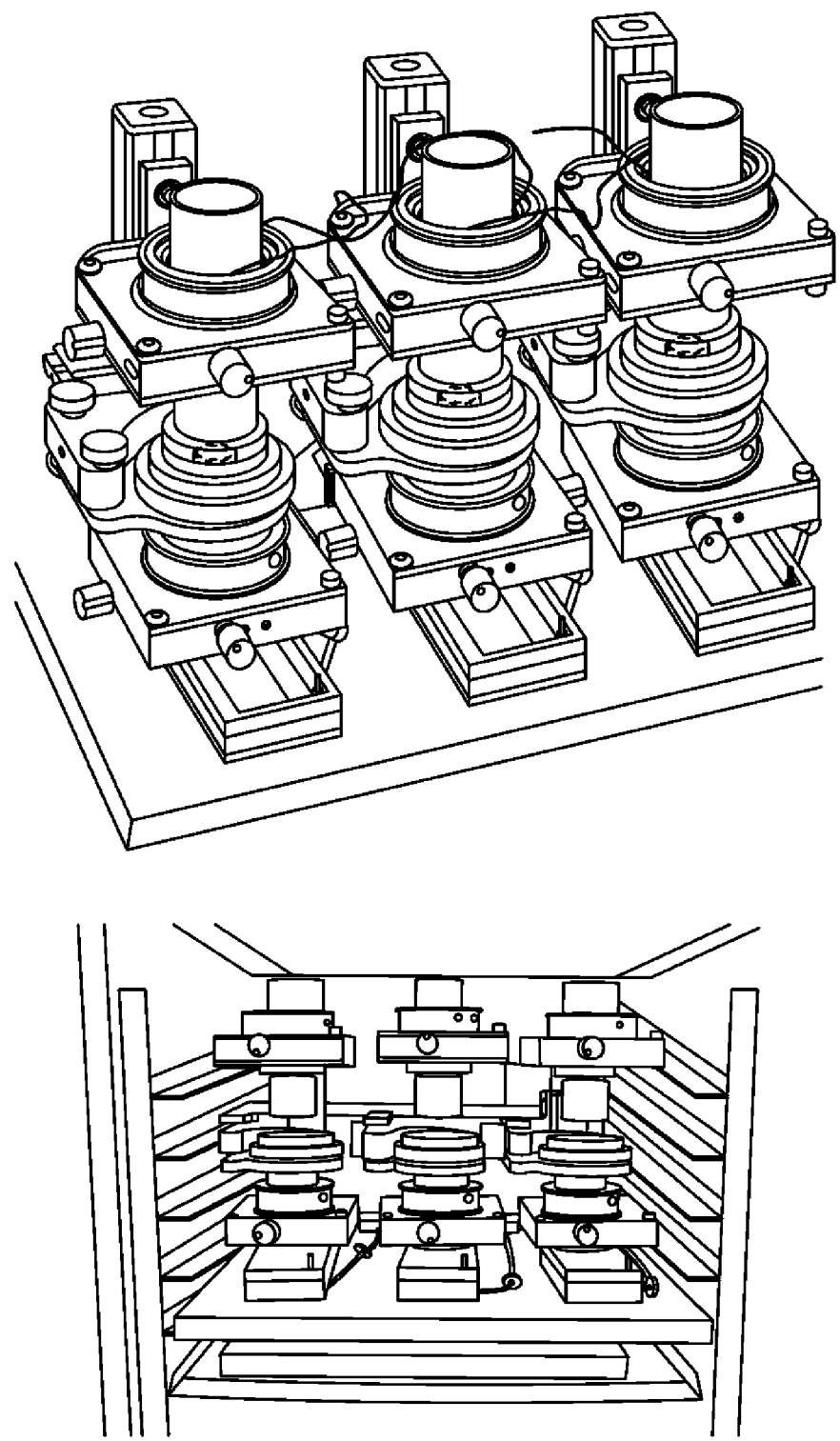
FIG. 23 is a schematic drawing of an array of three microscopes as illustrated in FIG. 22, mounted on a support for installation into an incubator and for computer connections.

FIG. 23A shows a schematic drawing of the multi-channel microscope array having 3 identical microscopes. All optical components are mounted in lens tubes. In operation of the array system, Petri dishes are located on the acrylic platforms that are mounted on manual 2-axis tilt stages, which allow adjustment of the image plane relative to the optical axis. These stages are fixed to the base of the microscope and do not move after the initial alignment. The illumination modules, consisting of LEDs, collimator lenses, patch stops, and condenser lenses, are mounted on manual xyz stages for position and focusing the illumination light. The imagine modules consisting of he objectives, achromat lenses, and CMOS sensors, are also mounted on the manual xyz states for positioning of the field-of-view and focusing the objectives. All 2 of the imaging modules are attached to linear slides and supported by a single lever arm, which is actuated using a stepper motor. This allows for computer-controlled focusing and automatic capture of image-stacks. Other methods of automatic focusing as well as actuation can be used.

The microscope array was placed inside a standard incubator, as shown in FIG. 23B. The CMOS image sensors are connected via USB connection to a single hub located inside the incubator, which is routed to an external PC along with other communication and power lines. All electrical cables exit the incubator through the center of a rubber stopper sealed with silicone glue.

Figure 24:
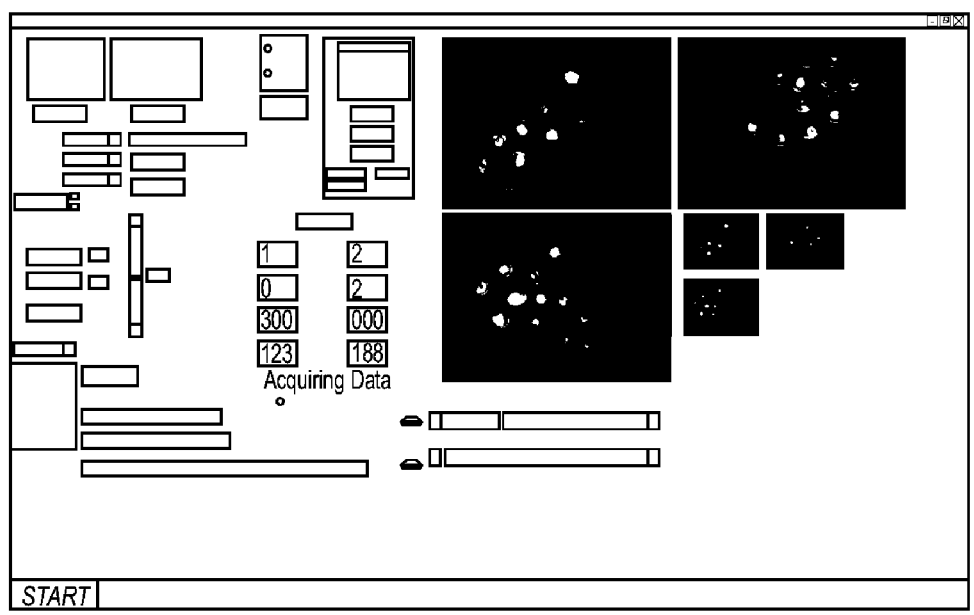
FIG. 24 is a screen shot of image capture software used in the present work, showing embryos being imaged from 3 channels.

The above described microscope array was used to record time-lapse images of early human embryo development and documented growth from zygote through blastocyst stages. Four different experiments monitored a total of 242 embryos. Out of this group, 100 were imaged up to day 5 or 6; the others were removed from the imaging stations at various time points for gene expression analysis. A screen shot of the image capture software and imaged embryos is shown in FIG. 24. Images were captured every 5 minutes with roughly 1 second of low-light exposure per image. The total amount of light received by the samples was equivalent to 24 minutes of continuous exposure, similar to the total level experienced in an IVF clinic during handling. The 1 second duration of light exposure per image can be reduced. Prior to working with the human embryos, we performed extensive control experiments with mouse pre-implantation embryos to ensure that both the blastocyst formation rate and gene expression patterns were not affected by the imaging process.

Figure 26:
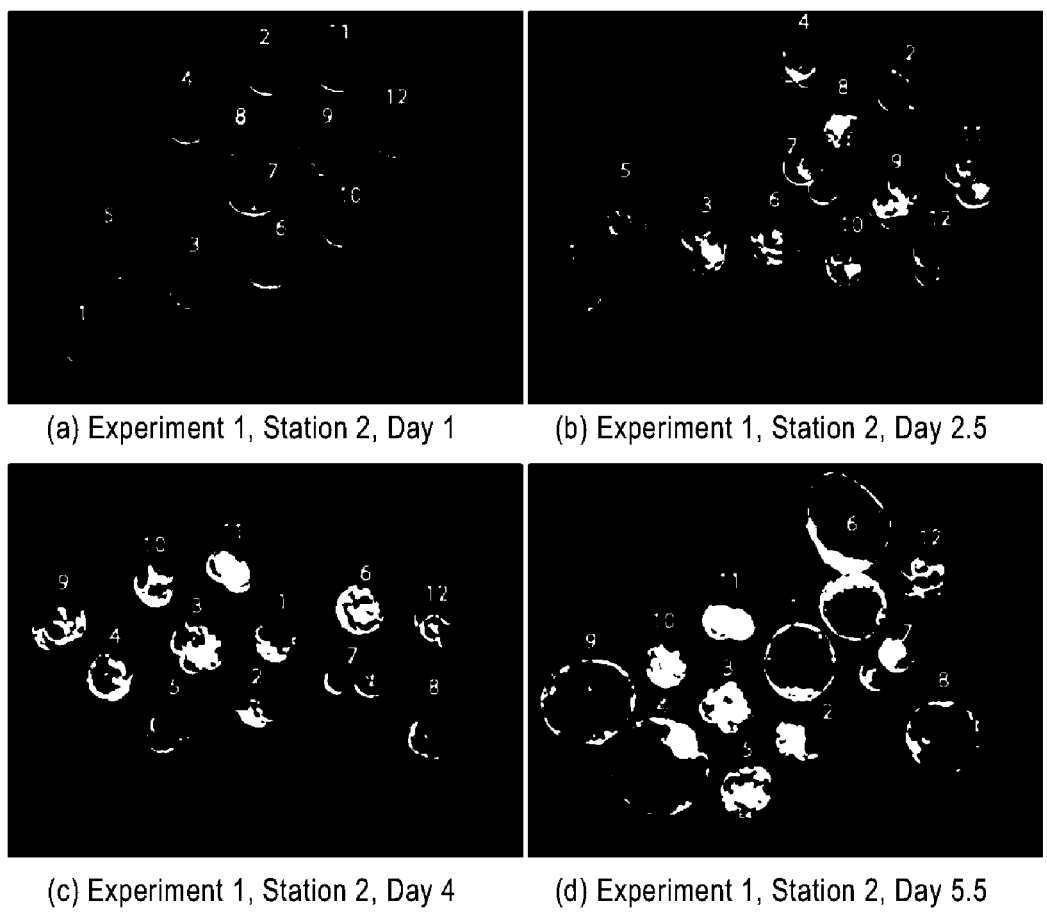
FIG. 26 A through D is a series of four photographs showing selected time-lapse images from experiment 1, station 2.

FIGS. 25 and 26 show selected images from the time-lapse sequences. Images are shown for day 1, day 2.5, day 4, and day 5.5. For the sequence shown in FIG. 25, 3 out of the 9 embryos developed into blastocysts, and for the sequence shown in FIG. 26, 5 out of the 12 embryos develop into blastocysts. Individual embryos were followed over time, even though their positions in the photographic field shifted as the embryos underwent a media change at day 3. The use of sequential media is needed to meet the stage-specific requirements of the developing embryos. During media change, the embryos were removed from the imaging station for a few minutes and transferred to new petri dishes. In order to keep track of each embryo's identity during media change, the transfer of samples from one dish to the other was videotaped to verify that embryos were not mixed up. This process was also used during the collection of samples for gene expression analysis. The issue of tracking embryo identity can be mitigated by using wells to help arrange the embryos in a particular order.

Petri Dish with Micro-Wells

Figure 27A:
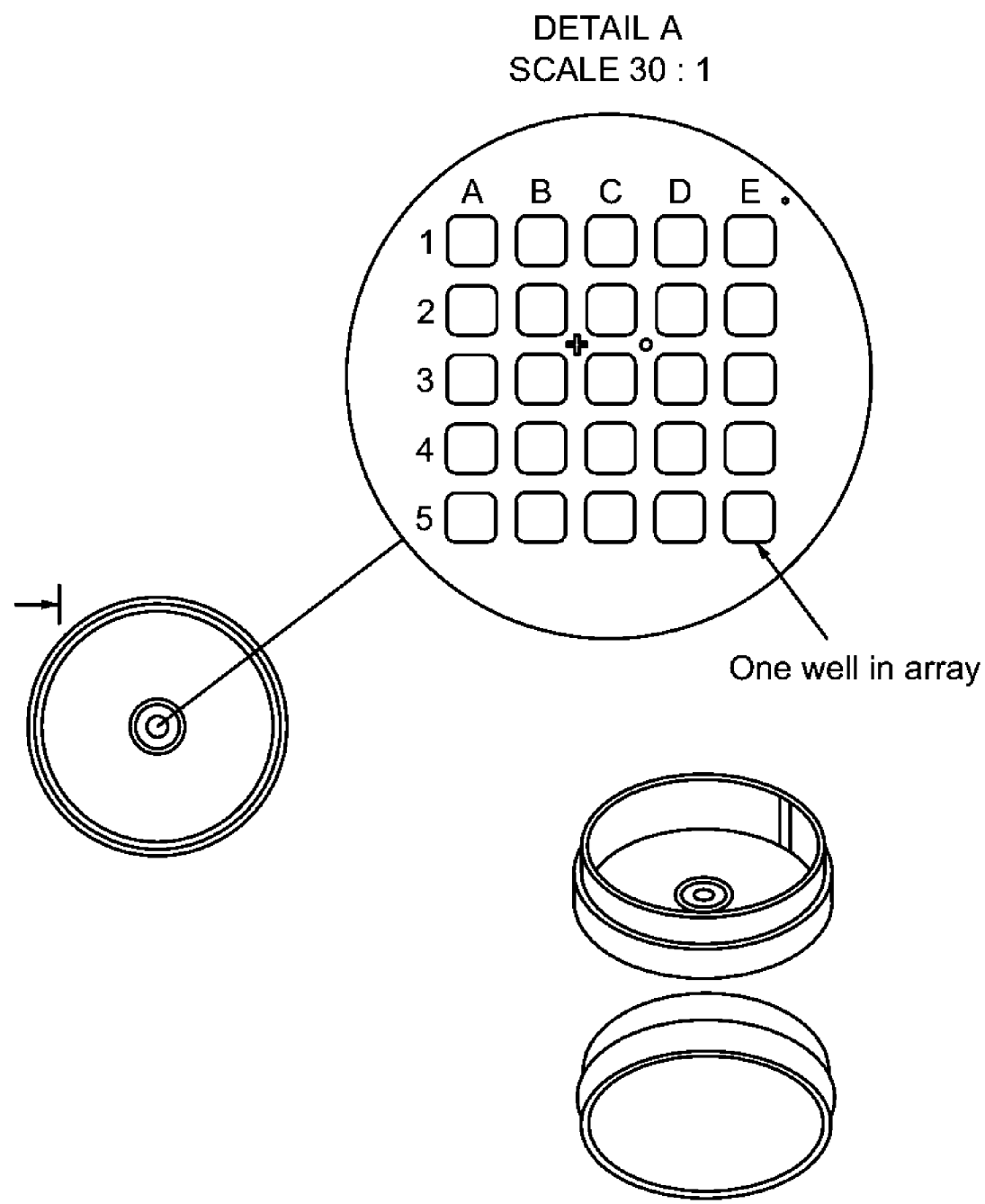
FIG. 27A shows a drawing of the dish with dimensions.
Figure 27B:
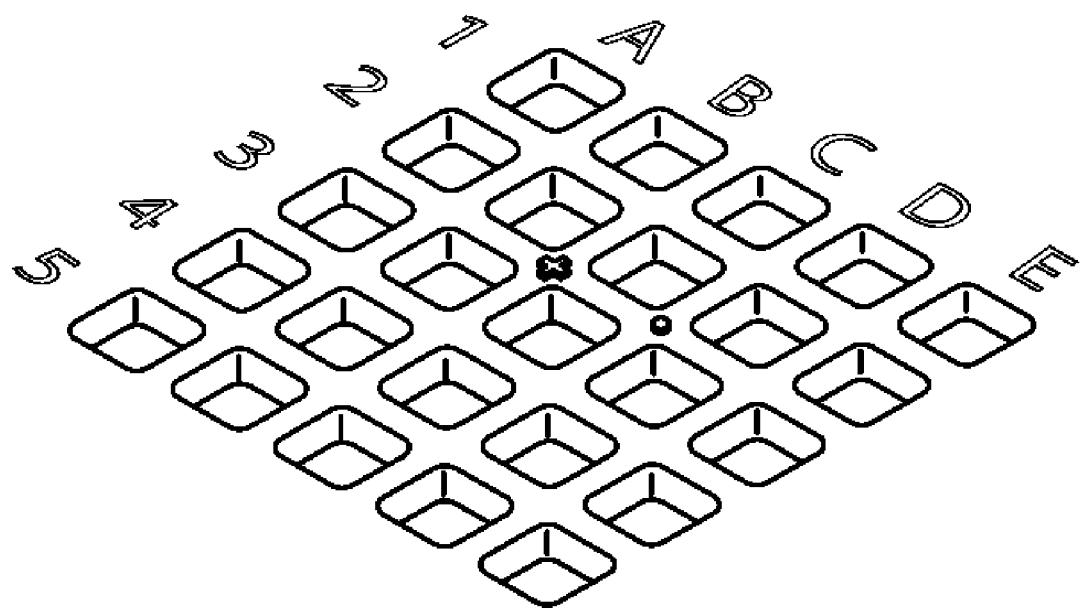
FIG. 27B shows a 3D-view of the micro-wells.

When transferring the petri dishes between different stations, the embryos can sometimes move around, thereby making it difficult to keep track of embryo identity. This poses a challenge when time-lapse imaging is performed on one station, and the embryos are subsequently moved to a second station for embryo selection and transfer. One method is to culture embryos in individual petri dishes. However, this requires each embryo to have its own media drop. In a typical IVF procedure, it is usually desirable to culture all of a patient's embryos on the same petri dish and in the same media drop. To address this problem, we have designed a custom petri dish with micro-wells. This keeps the embryos from moving around and maintains their arrangement on the petri dish when transferred to and from the incubator or imaging stations. In addition, the wells are small enough and spaced closely together such that they can share the same media drop and all be viewed simultaneously by the same microscope. The bottom surface of each micro-well has an optical quality finish. FIG. 27A shows a drawing with dimensions for one embodiment. In this version, there are 25 micro-wells spaced closely together within a 1.7×1.7 mm field-of-view. FIG. 27B shows a 3D-view of the micro-wells, which are recessed approximately 100 microns into the dish surface. Fiducial markers, including letters, numbers, and other markings, are included on the dish to help with identification.

All references cited herein are incorporated by reference in their entireties.

EXAMPLES

The following examples are put forth so as to provide those of ordinary skill in the art with a disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Sample Source

All embryos used in this study were collected over a multi-year period and fertilized and cryopreserved by multiple embryologists. The average number of embryos per patient in our study was 3, and all age groups encountered in a routine IVF center were included. Notably, all of the embryos used for these experiments were IVF-generated (as opposed to ICSI), so the embryos were derived from sperm that had relatively normal function (at least in terms of their ability to penetrate the cumulus, zona, and oolemma and form a pronuclei). Stimulation protocols were standard long lupron protocols (cdc.gov/art). Cryopreservation of supernumerary human embryos was accomplished by placing them in freezing medium (1.5 M 1,2 propanediol+0.2 M sucrose) for 25 minutes at room temperature (22+2° C.). The embryos were then frozen using a slow-freeze protocol (−1° C./min to −6.5° C.; hold for 5 min; seed; hold for 5 min; −0.5° C./min to −80° C.; plunge in liquid nitrogen). Committee. No protected health information could be associated with the embryos.

A large set of cryopreserved embryos were validated and the following observations were made: 1) The embryos demonstrated timing indicative of normal embryo development in terms of landmarks including: Cleavage to 2 cells (occurred early Day 2), onset of RNA degradation (occurred on Days 1 to 3), cleavage to 4 and 8 cells (occurred on late Day 2 and Day 3, respectively), activation of the embryonic genome (on Day 3 at the 8-cell stage), and formation of the morula and blastocyst (occurred on Days 4 and 5, respectively). 2) The embryos demonstrated an efficiency in reaching blastocyst stage that is typical of embryos obtained in a clinical setting. This is likely due to the fact that the embryos were cryopreserved at the 2PN stage and represented the array of embryos encountered in an IVF clinic since no "triage" of those that would and would not develop was done prior to cryopreservation at the 1-cell stage (as is typical of embryos cryopreserved later in development at the Day 3 or blastocyst stages). Thus, our data confirms that these embryos exhibited similar blastocyst formation rates compared to those observed in typical IVF clinics. 3) Previous studies have demonstrated that embryos that are frozen at the 2PN stage exhibit a similar potential for development, implantation, clinical pregnancy, and delivery when compared to fresh embryos. Other studies have also shown similar results for frozen oocytes suggesting that the earliest events of human embryo development maintain an appropriate timeline post-cryopreservation. 4) We focused on parameters that were not dependent on time of fertilization or thaw time. The first parameter that we measure (duration of the first cytokinesis) is of short duration (ca 10-15 min) and is not dependent on the time of fertilization in this study (it is able to be measured independently in all embryos regardless of final outcome). Moreover, all subsequent parameters are measured relative to this initial measurement point and compared between embryos that succeed to develop to blastocyst and those that fail to do so. 5) Finally, we note that fresh (unfrozen) embryos that are 3PN are known to develop along the same time frame as fresh normal embryos; we compared parameters in fresh 3PN embryos that we obtained from the Stanford IVF clinic, and observed that they were not different from those of our cryopreserved embryos or published reports.

Experimental Plan

In four experimental sets, we tracked the development of 242 pronuclear stage embryos (61, 80, 64 and 37, respectively). In each set of experiments, human zygotes were thawed on Day 1 and cultured in small groups on multiple plates. Each plate was observed independently with time-lapse microscopy under darkfield illumination on separate imaging stations. At approximately 24 hour intervals, one plate of embryos was removed from the imaging system and collected as either single embryos or single cells (blastomeres) for high throughput real-time quantitative PCR gene expression analysis. Each plate typically contained a mixture of embryos that reached the expected developmental stage at the time of harvest (termed "normal") and those that were arrested or delayed at earlier development stages, or fragmented extensively (termed "abnormal"). Embryos were analyzed as either single intact embryos or were disassociated into single blastomeres followed by gene-specific RNA amplification. A subset of embryos (100 out of 242) was imaged until Day 5 or 6 in order to monitor blastocyst formation.

Human Embryo Culture and Microscopy

Human embryos were thawed by removing the cryovials from the liquid nitrogen storage tank and placing them at room temp. Once a vial was thawed, it was opened and the embryos were visualized under a dissecting microscope. The contents of the vial were then poured into the bottom of a 3003 culture dish. The embryos were located in the drop and the survival of each embryo was assessed and recorded. At room temperature, the embryos were transferred to a 3037 culture dish containing 1.0 M 1,2 propanediol+0.2M sucrose for 5 minutes, then 0.5 M 1,2 propanediol+0.2M sucrose for 5 minutes, and 0.0 M 1,2 propanediol+0.2M sucrose for 5 minutes. Subsequently, embryos were cultured in Quinn's Advantage Cleavage Medium (CooperSurgical) supplemented with 10% Quinn's Advantage Serum Protein Substitute (SPS; CooperSurgical) between Day 1 to 3, and Quinn's Advantage Blastocyst Medium (CooperSurgical) with 10% SPS after Day 3 using microdrops under oil. All of the experiments used the same type of cleavage-stage medium, except for two stations during the first experiment, which used a Global medium (LifeGlobal, Guilford, Conn.). In this small subset (12 embryos), the embryos exhibited a slightly lower blastocyst formation rate (3 out of 12, or 25%) but the sensitivity and specificity of our predictive parameters were both 100% for this group.

Time-lapse imaging was performed on multiple systems to accommodate concurrent analysis of multiple samples as well as to validate the consistency of the data across different platforms. The systems consisted of 7 individual microscopes: (1) two modified Olympus IX-70/71 microscopes equipped with Tokai Hit heated stages, white-light Luxeon LEDs, and an aperture for darkfield illumination; (2) two modified Olympus CKX-40/41 microscopes equipped with heated stages, white-light Luxeon LEDs, and Hoffman Modulation Contrast illumination (note: these systems were used only during the first of 4 experiments after it was decided that darkfield illumination was preferable for measuring the parameters); and (3) a custom built 3-channel miniature microscope array that fits inside a standard incubator, equipped with white-light Luxeon LEDs and apertures for darkfield illumination. We observed no significant difference in developmental behaviour, blastocyst formation rate, or gene expression profiles between embryos cultured on these different systems; indeed, our parameters for blastocyst prediction were consistent across multiple systems and experiments.

The light intensity for all systems was significantly lower than the light typically used on an assisted reproduction microscope due to the low-power of the LEDs (relative to a typical 100 W Halogen bulb) and high sensitivity of the camera sensors. Using an optical power meter, we determined that the power of a typical assisted reproduction microscope (Olympus IX-71 Hoffman Modulation Contrast) at a wavelength of 473 nm ranges from roughly 7 to 10 mW depending on the magnification, while the power of our imaging systems were measured to be between 0.2 and 0.3 mW at the same wavelength. Images were captured at a 1 second exposure time every 5 minutes for up to 5 or 6 days, resulting in approximately 24 minutes of continuous light exposure. At a power of 0.3 mW, this is equivalent to roughly 1 minute of exposure under a typical assisted reproduction microscope.

To track the identity of each embryo during correlated imaging and gene expression experiment, we installed a video camera on the stereomicroscope and recorded the process of sample transfer during media change and sample collection. We performed control experiments with mouse preimplantation embryos (n=56) and a small subset of human embryos (n=22), and observed no significant difference (p=0.96) in the blastocyst formation rate between imaged and control embryos.

High Throughput qRT-PCR Analysis

For single embryo or single blastomere qRT-PCR analysis, embryos were first treated with Acid Tyrode's solution to remove the zona pellucida. To collect single blastomeres, the embryos were incubated in Quinn's Advantage $Ca^{2+}Mg^{2+}$ free medium with HEPES (CooperSurgical) for 5 to 20 minutes at 37° C. with rigorous pipetting. Samples were collected directly into 10 µl of reaction buffer; subsequent one-step reverse transcription/pre-amplification reaction was performed as previously described. Pooled 20×ABI assay-on-demand qRT-PCR primer and probe mix (Applied Biosystems) were used as gene-specific primers during the reverse transcription and pre-amplification reactions. High throughput qRT-PCR reactions were performed with Fluidigm Biomark 96.96 Dynamic Arrays as previously described using the ABI assay-on-demand qRT-PCR probes. All samples were loaded in 3 or 4 technical replicates. qRT-PCR data analysis was performed with qBasePlus (Biogazelle), Microsoft Excel, and a custom built software. Certain genes were omitted from data analysis due to either poor data quality (e.g. poor PCR amplification curves) or consistent low to no expression in the embryos assessed. For the analysis of blastomere age, the maternal transcript panel used includes DAZL, GDF3, IFITM1, STELLAR, SYCP3, VASA, GDF9, PDCD5, ZAR1 and ZP1, whereas the embryonic gene panel includes ATF7IP, CCNA1, EIF1AX, EIF4A3, H2AFZ, HSP70.1, JARID1B, LSM3, PABPC1, and SERTAD1. The expression value of each gene relative to the reference genes GAPDH and RPLP0, as well as relative to the gene average, was calculated using the geNorm and $\Delta\Delta Ct$ methods. GAPDH and RPLP0 were selected as the reference genes for this study empirically based on the gene stability value and coefficient of variation: 1.18 and 46% for GAPDH and 1.18 and 34% for RPLP0. These were the most stable among the 10 housekeeping genes that we tested and well within range of a typical heterogeneous sample set. Second, we observed that in single blastomeres, as expected, the amount of RPLP0 and GAPDH transcripts decreased by approximately 1 Ct value per division between 1-cell and 8-cell stage, congruent with expectations that each cell inherits approximately one half of the pool of mRNA with each cleavage division, in the absence of new transcripts prior to EGA during the first 3 days of human development. Third, we noted that the expression level of these reference genes in single blastomeres remained stable between 8-cell to morula stage, after EGA began. At the intact embryo level, the Ct values of both RPLP0 and GAPDH remained largely constant throughout development until the morula stage with a slight increase following in the blastocyst stage perhaps due to increased transcript levels in the greater numbers of blastomeres present. Most of the gene expression analysis performed in this study focused on developmental stages prior to the morula stage, however, when the expression level of the reference genes was extremely stable.

Automated Cell Tracking

Our cell tracking algorithm uses a probabilistic framework based on sequential Monte Carlo methods, which in the field of computer-vision is often referred to as the particle filter. The particle filter tracks the propagation of three main variables over time: the state, the control, and the measurement. The state variable is a model of an embryo and is represented as a collection of ellipses. The control variable is an input that transforms the state variable and consists of our cell propagation and division model. The measurement variable is an observation of the state and consists of our images acquired by the time-lapse microscope. Our estimate of the current state at each time step is represented with a posterior probability distribution, which is approximated by a set of weighted samples called particles. We use the terms particles and embryo models interchangeably, where a particle is one hypothesis of an embryo model at a given time. After initialization, the particle filter repeatedly applies three steps: prediction, measurement, and update.

Prediction: Cells are represented as ellipses in 2D space, and each cell has an orientation and overlap index. The overlap index specifies the relative height of the cells. In general, there are two types of behaviour that we want to predict: cell motion and cell division. For cell motion, our control input takes a particle and randomly perturbs each parameter for each cell, including position, orientation, and length of major and minor axes. The perturbation is randomly sampled from a normal distribution with relatively small variance (5% of the initialized values). For cell division, we use the following approach. At a given point in time, for each particle, we assign a 50% probability that one of the cells will divide. This value was chosen empirically, and spans a wide range of possible cell divisions while maintaining good coverage of the current configuration. If a division is predicted, then the dividing cell is chosen randomly. When a cell is chosen to divide, we apply a symmetric division along the major axis of the ellipse, producing two daughter cells of equal size and shape. We then randomly perturb each value for the daughter cells. Finally, we randomly select the overlap indices of the two daughter cells while maintaining their collective overlap relative to the rest of the cells.

After applying the control input, we convert each particle into a simulated image. This is achieved by projecting the elliptical shape of each cell onto the simulated image using the overlap index. The corresponding pixel values are set to a binary value of 1 and dilated to create a membrane thickness comparable to the observed image data. Since the embryos are partially transparent and out-of-focus light is collected, cell membranes at the bottom of the embryo are only sometimes visible. Accordingly, occluded cell membranes are added with 10% probability. In practice, we have found that these occluded membrane points are crucial for accurate shape modeling, but it is important to make them sparse enough so that they do not resemble a visible edge.

Measurement: Once we have generated a distribution of hypothesized models, the corresponding simulated images are compared to the actual microscope image. The microscope image is pre-processed to create a binary image of cell membranes using a principle curvature-based method followed by thresholding. The accuracy of the comparison is evaluated using a symmetric truncated chamfer distance, which is then used to assign a weight, or likelihood, to each particle.

Update: After weights are assigned, particles are selected in proportion to these weights to create a new set of particles for the next iteration. This focuses the particle distribution in the region of highest probability. Particles with low probability are discarded, while particles with high probability are multiplied. Particle re-sampling is performed using the low variance method.

Once the embryos have been modeled, we can extract the dynamic imaging parameters such as duration of cytokinesis and time between mitosis, as discussed in the main text. Our cell tracking software was previously implemented in Matlab, and computation times ranged from a couple seconds to half a minute for each image depending on the number of particles. Our current version of the software is implemented in C, and computation times range from 1 to 5 seconds depending on the number of particles.

Example 1

Imaging analysis to determine developmental potential of embryos.

Methods

Frozen 1-cell human embryos, also referred to as zygotes, were thawed and placed into culture and cultured under conditions such as those used in IVF procedures. As described in more detail above, these embryos appear to be representative of the typical in vitro fertilization (IVF) population as they were frozen at the 2PN stage and thus indiscriminately cryopreserved. This is in contrast to embryos typically cryopreserved at later stages of development following transfer of those perceived to be of the highest quality, during fresh cycles. For some experiments, embryos were placed in a standard culture dish. For other experiments, embryos were cultured in custom culture dish with optical quality microwells.

The growing embryos, typically between 1 to 30 per dish, were followed individually by time lapse imaging with a computer controlled microscope equipped for digital image storage and analysis. In some instances, time-lapse imaging was performed with inverted microscopes equipped with heated stages and incubation chambers. In other instances, time-lapse imaging was performed with custom built miniature microscope arrays that fit inside a conventional incubator, which enabled the concurrent culture of multiple dishes of samples in the same incubator and was scalable to accommodate multiple channels with no limitations on the minimum time interval between successive image capture. Using multiple microscopes also eliminated the need to move the sample, which improved the system accuracy and overall system reliability. The imaging systems used darkfield illumination, which provided enhanced image contrast for subsequent feature extraction and image analysis, although it was noted that other illumination would have been sufficient. The individual microscopes in the incubator were isolated from one another, providing each culture dish with its own controlled environment. This allowed dishes to be transferred to and from the imaging stations without disturbing the environment of the other samples.

Time-lapse images were collected for subsequent analysis of cellular morphology, including measurement of at least one of the following cellular parameters: the duration of first cytokinesis, the time interval between first and second cell division, and the time interval between the second and third cell division. The images shown in the figures were taken at 1 second exposure time every 5 minutes for up to 5 or 6 days. As described in greater detail below, first cytokinesis usually occurs one day after fertilization and lasts between about 14 minutes. First and second cell divisions are usually separated by an average of about 11 hours. Second and third cell divisions are usually separated by an average of about 1 hour. Thus, imaging was over a period of time lasting approximately 36 hours (plus or minus several hours) after fertilization.

Results

Figure 2:
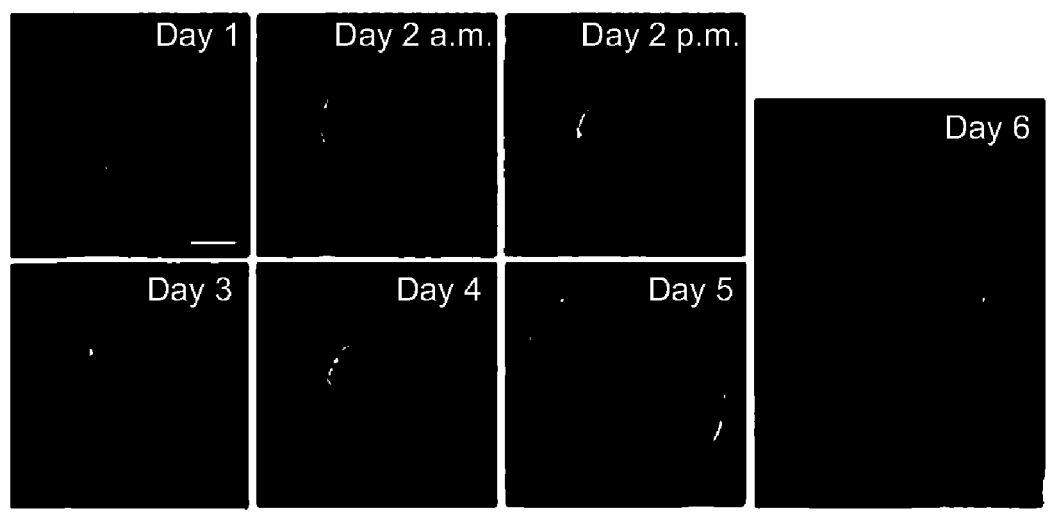
FIG. 2 is a series of photographs showing cell cleavage and division over period of 6 days. Images are labeled day 1 through day 6. Scale bar represents 50 μm.

The developmental timeline of a healthy human preimplantation embryo in culture was documented over a six day period by time lapse imaging (FIG. 2). It was observed that a normal human zygote undergoes the first cleavage division early on Day 2. Subsequently, the embryo cleaves to a 4-cell and 8-cell embryo later on Day 2 and Day 3 respectively, before compacting into a morula on Day 4. The first morphologically evident cellular differentiation is observed on Day 5 and 6 during blastocyst formation, when the totipotent blastomeres differentiate to either trophectoderm cells, which give rise to extra-embryonic structures like the placenta, or inner cell mass, which develops into the fetus in vivo and pluripotent embryonic stem cells in vitro.

Figure 3:
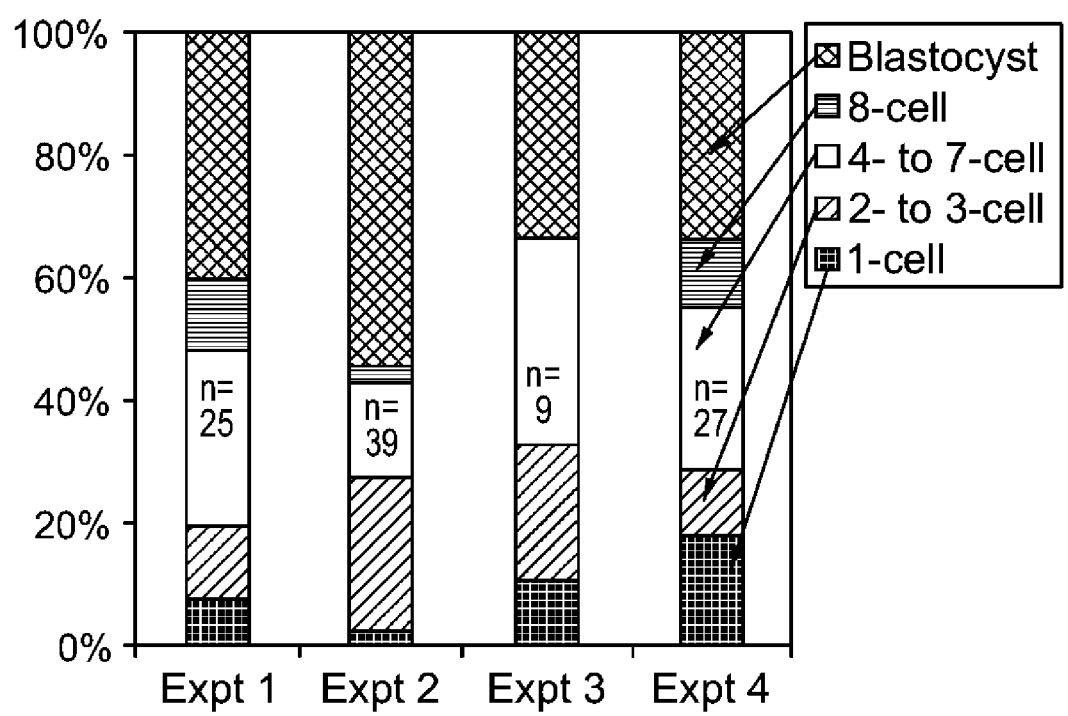
FIG. 3 is a bar graph showing percentages of successful development into blastocysts from 1-cell embryos (zygotes). Over the course of 4 separate experiments, a total of 100 embryos were observed until Day 5 to 6 via time-lapse microscopy. The percentage of cells reaching each indicated stage (blastocyst, 8-cell, 4- to 7-cell, 2- to 3-cell and 1-cell) is shown.

We next tracked the development of 242 normally-fertilized embryos in four independent experiment sets and documented the distribution of normal and arrested embryos among samples that were cultured to Day 5 or 6. Of the 242 embryos, 100 were cultured to Day 5 or 6 and the blastocyst formation rate was observed to be between 33%-53%, similar to the blastocyst formation rate at a typical IVF clinic (FIG. 3). The remaining embryos arrested at different stages of development, most commonly between 2-cell and 8-cell stage, and were defined as abnormal (FIG. 3). In order to identify quantitative imaging parameters that predict success in embryo development to the blastocyst stage, we extracted and analyzed several parameters from timelapse videos, including blastomere size, thickness of the zona pellucida, degree of fragmentation, length of the first cell cycles, time intervals between the first few mitoses, and duration of the first cytokinesis. During video image analysis of both developmentally normal and abnormal embryos, we observed that many arrested embryos underwent aberrant cytokinesis during the first cell division. Normal embryos completed cytokinesis in a narrow time window of 14.3+/−6.0 min from appearance of the cleavage furrows to complete separation of the daughter cells, in a smooth and controlled manner. This is shown in FIG. 4 top. In contrast, abnormal embryos commonly showed one of two aberrant cytokinesis phenotypes. In the milder phenotype, the morphology and mechanism of cytokinesis appeared normal, but the time required to complete the process was longer, ranging from a few additional minutes to an hour (FIG. 4). Occasionally, an embryo that underwent a slightly prolonged cytokinesis still developed into a blastocyst. In the more severe phenotype, the morphology and mechanism of cytokinesis were perturbed. For example, as shown in the example in the bottom panel of FIG. 4, embryos formed a one-sided cleavage furrow and underwent an unusual series of membrane ruffling events for several hours before finally fragmenting into smaller components. Other variations of such behaviour were also observed. Additionally, abnormal embryos demonstrating these more severe phenotypes frequently became fragmented, providing direct evidence that embryo fragmentation is likely a by-product of aberrant cytokinesis that subsequently results in abnormal embryo development.

Figure 5:
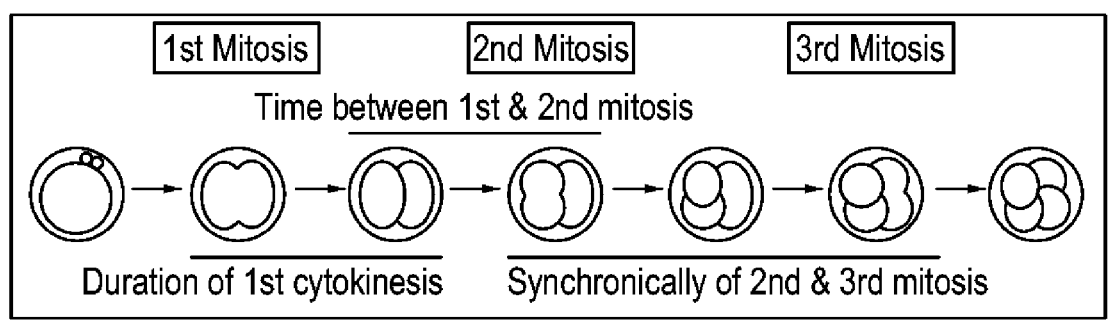
FIG. 5 is a diagram showing time lapses between stages used for the present evaluations, including the duration of the first cytokinesis, time between the first and second division (measured as the time interval between the resolution of cytokinesis 1 and the onset of cytokinesis 2), and time between the 2nd and 3rd mitosis (measured as the time interval between the initiation of cytokinesis 2 and the initiation of cytokinesis 3).

Detailed analysis of the our imaging results indicated that normal embryos followed strict timing in cytokinesis and mitosis during early divisions, before embryonic gene activation (EGA) begins, suggesting that the developmental potential of an embryo is predetermined by inherited maternal programs. In particular, we noted three temporal intervals, or parameters, in the cell cycles of early-stage embryo that were strictly regulated: (1) duration of the first cytokinesis, (2) time interval between the first and second mitosis, and (3) synchronicity of the second and third mitosis. The relationship between these three time intervals and morphological changes is shown in FIG. 5. For normal embryos, we measured these parameters to be, approximately, 14.3+/−6.0 minutes, 11.1+/−2.1 hours, and 1.0+/−1.6 hours, respectively (given here as mean plus/minus standard deviation).

We also performed imaging on a small set (n=10) of fresh (non-cryopreserved) embryos that were 3PN (triploid) starting at the single-cell stage. 3PN embryos have been shown to follow the same timeline of landmark events as normal fresh embryos through at least the first three cell cycles. These embryos were imaged prior to our main experiments in order to validate the imaging systems (but for technical reasons were not followed out to blastocyst). Out of this set of fresh embryos, 3 of the embryos followed a similar timeline of events as our cryopreserved 2PN embryos, with duration of cytokinesis ranging from 15 to 30 min, time between first and second mitosis ranging from 9.6 to 13.8 hours, and time between second and third mitosis ranging from 0.3 to 1.0 hours. However, in 7 of the embryos we observed a unique cytokinesis phenotype that was characterized by the simultaneous appearance of 3 cleavage furrows, a slightly prolonged cytokinesis, and ultimately separation into three daughter cells (FIG. 4). These embryos had a duration of cytokinesis ranging from 15 to 70 min (characterized as the time between the initiation of the cleavage furrows until complete separation into 3 daughter cells), time between first and second mitosis (3-cell to 4-cell) ranging from 8.7 to 12.7 hours, and time between second and third mitosis (4-cell to 5-cell) ranging from 0.3 to 2.6 hours. This observation, together with the diverse range of cytokinesis phenotypes displayed by abnormal embryos, suggests that our cryopreserved embryos are not developmentally delayed by the cryopreservation process and behave similarly to fresh zygotes that cleave to 2 blastomeres.

Figure 6:
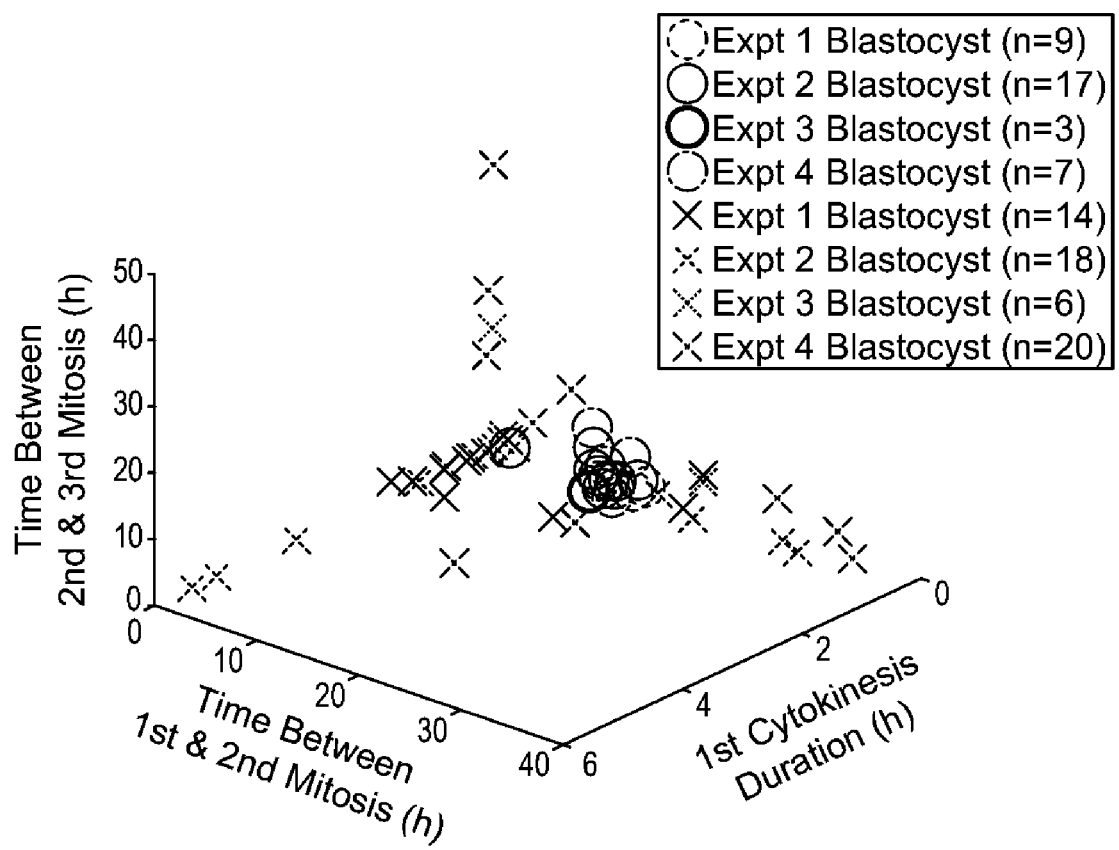
FIG. 6 is a 3-D point graph showing the measurement of three events, including the duration of the first cytokinesis, the time interval between the first and second cell divisions (measured as the time interval between the resolution of cytokinesis 1 and the onset of cytokinesis 2), and the time interval between the second cell and third cell divisions (measured as the time interval between the initiation of cytokinesis 2 and the initiation of cytokinesis 3), for a large group of embryos. The embryos that reach the blastocyst stage (marked with circles) are shown to cluster together on the 3-D graph, while embryos that arrest (marked with X's) before reaching blastocyst are scattered throughout.

Embryos that reached the blastocyst stage could be predicted, with sensitivity and specificity of 94% and 93% respectively, by having a first cytokinesis of between 0 to 33 min, a time between first and second mitosis of between 7.8 to 14.3 hours, and a time between second and third mitosis of between 0 to 5.8 hours (FIG. 6). Conversely, embryos that exhibited values outside of one or more of these windows were predicted to arrest. All the normal embryos that successfully developed into a blastocyst exhibited similar values in all three parameters. In contrast, the abnormal embryos exhibited a highly amount of variability in the lengths of time they took to complete the intervals (FIG. 6). We observed that (1) a longer period of time to complete first cytokinesis than normal indicates poor developmental potential; (2) a longer or shorter interval between first and second cell divisions than normal indicates poor developmental potential; and (3) a longer interval between the second and third cell divisions than normal indicates poor developmental potential. Thus, these parameters were predictive of the ability of the embryo to proceed to blastocyst formation and blastocyst quality.

Finally, we noted that while each parameter was autonomously predictive of the developmental potential of the embryo, the use of all three parameters provided sensitivity and specificity that both exceeded 90%, with a cutoff point of 3 times the standard deviations. The receiver operating characteristic (ROC) curve for these parameters is shown in FIG. 7. The curve in this figure shows the true positive rate (sensitivity) vs. the false positive rate (1—specificity) for various standard deviation cutoffs. To arrive at this ROC, the following numbers were used: Number of true positives=34 (correctly predicted to reach blastocyst); number of true negatives=54 (correctly predicted to arrest); number of false positives=4 (incorrectly predicted to reach blastocyst); number of false negatives=2 (incorrectly predicted to arrest).

Discussion

Our analysis indicates that embryos that follow strict timing in mitosis and cytokinesis during the first three cleavage divisions are much more likely to both develop to blastocyst stage and form a high-quality blastocyst with an expanded inner cell mass (ICM). The dynamic morphological parameters can be used to select the optimal embryos for transfer or cryo-preservation during an IVF procedure. These parameters can also be used to distinguish between different qualities of blastocyst, allowing for a ranking of the relative developmental potentials of embryos within a group. The standard practice in IVF clinics is to transfer at the 8-cell stage (day-3). Some clinics choose to culture embryos to the blastocyst stage (day-5 since blastocyst transfer has up to double the implantation rates compared to day-3 transfer, However, many clinics avoid prolonged culture due to increased risk of epigenetic disorders. The predictive imaging parameters can be used to predict embryo viability by the 4-cell stage (on day-2) and prior to embryonic gene activation. This can allow for the transfer or cryo-preservation of embryos a full day earlier than is typically practiced and before the embryos undergo significant changes in their molecular programs. This can also allow for the most optimal embryos to be selected for PGD or other types of analysis.

Example 2

Validation of imaging parameters through gene expression analysis, and use of gene expression analysis to determine developmental potential.

Methods

Frozen 1-cell human embryos, also referred to as zygotes, were thawed and placed into culture and cultured under conditions such as those used in IVF procedures. For some experiments, embryos were placed in a standard culture dish. For other experiments, embryos were cultured in custom culture dish with optical quality micro-wells.

Embryos were removed from the culture and imaging system and collected as either single embryos or single cells (blastomeres) thr gene expression analysis. Each plate typically contained a mixture of embryos, with some reaching the expected developmental stage at the time of harvest, and others arresting at earlier developmental stages or fragmenting extensively. Those that reached the expected developmental stage at the time of harvest were classified as "normal", whereas those that arrested were considered "abnormal. For example, when a plate of embryos was removed from the imaging station on late Day 2 for sample collection, any embryo that had reached 4-cell stage and beyond would be identified as normal, whereas those that failed to reach 4-cell stage would be labelled as arrested. These arrested embryos were categorized by the developmental stage at which they became arrested, such that an embryo with only 2 blastomeres on late Day 2 would be analyzed as an arrested 2-cell embryo. Care was taken to exclude embryos that morphologically appeared to be dead and porous at the time of sample collection (e.g. degenerate blastomeres). Only embryos that appeared alive (for both normal and arrested) were used for gene expression analysis. However, it is possible that embryos that appeared normal during the time of collection might ultimately arrest if they were allowed to grow to a later stage. Gene expression analysis of embryos representative of each of these classes was performed by quantitative RT-PCR (qRT-PCR). At approximately 24 hour intervals, embryos were collected from the individual imaging systems for high throughput qRT-PCR gene expression analysis with multiplex reactions of up to 96 genes assayed against 96 sample. Gene expression analysis was performed with the Fluidigm Biomark System, which can carry out up to 9216 simultaneous TaqMan assay-based qRT-PCR reactions in nanoliter quantities.

Results

In order to elucidate molecular mechanisms that may underlie the morphological events, we performed correlated gene expression profiling. The expression levels of 96 different genes belonging to different categories were assayed per sample, including housekeeping genes, germ cell markers, maternal factors, EGA markers, trophoblast markers, inner cell mass markers, pluripotency markers, epigenetic regulators, transcription factors, hormone receptors and others (Table 1, in FIG. 19). Two slightly different but overlapping sets of genes were assayed in two different experimental sets, providing a unique set of genes diagnostic of human embryo fate. The unique gene sets were compiled from data regarding gene expression in embryos from model organisms or in human embryonic stem cells, as well as from our own unpublished microarray data. The expression status of these gene sets in human preimplantation embryos is revealed for the first time in this study.

The expression value of each gene relative to the reference genes GAPDH and RPLPO, as well as relative to the gene average, was calculated using the geNorm (El-Toukhy T, et al. (2009) Hum Reprod) and AACt (Vanneste E, et al, (2009) Nat Med 15:577-83) methods. The gene stability value and coefficient of variation was 1.18 and 46% for GAPDH and 1.18 and 34% for RPLPO, most stable among the 10 housekeeping genes we tested and well within range of a typical heterogeneous sample set. In single blastomeres, as expected, the amount of RPLPO and GAPDH transcripts decreased by approximately 1 Ct value per division between 1-cell and 8-cell stage, due to the halving effect of cleavage division as well as the lack of EGA during the first 3 days of human development. The expression level of these reference genes in single blastomeres remained stable between 8-cell to morula stage. At the whole embryo level, the Ct values of both RPLPO and GAPDH remained largely constant throughout development until the morula stage. The expression level of RPLPO and GAPDH increased significantly in the blastocysts, most likely due to the increased number of blastomeres present. These variations did not affect the validity of RPLPO and GAPDH as reference genes. Most of the gene expression analysis performed in this study focused on developmental stages before the morula stage, when the expression level of the reference genes was extremely stable.

Figure 8:
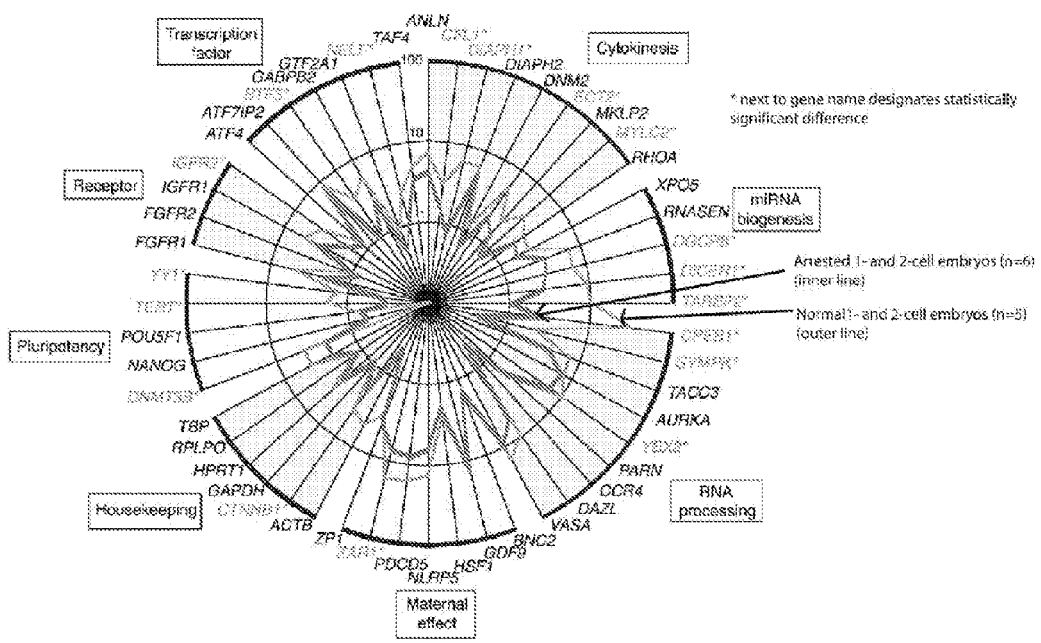
FIG. 8 is a radar graph showing gene expression levels of 52 genes from 6 arrested 1- to 2-cell embryos and 5 normal 1- to 2-cell embryos. The difference in expression levels between normal and abnormal embryos was statistically significant for those genes highlighted in yellow and denoted with an asterisk, as determined by the Mann-Whitney test.

Differential gene expression between normal and abnormal embryos. FIG. 8 shows the average expression level of 52 genes from 6 abnormal 1- to 2-cell embryos and 5 normal 1- to 2-cell embryos plotted in a radar graph on a logarithmic scale. Arrested embryos in general showed reduced amount of mRNA compared to normal embryos, with genes that facilitated cytokinesis, RNA processing and miRNA biogenesis most severely affected. Genes highlighted with an asterisk indicate a statistically significant difference ($p<0.05$) between normal and abnormal embryos as determined by the Mann-Whitney test. These 18 genes are Cofillin, DIAPH1, ECT2, MYLC2, DGCR8, Dicer, TARBP2, CPEB1, Symplekin, YBX2, ZAR1, CTNNB1, DNMT3B, TERT, YY1, IFGR2, BTF3 and NELF. Each gene belongs to a group as indicated in the Figure, namely Cytokinesis: Cofillin, DIAPH1, ECT2 and MYCL2; miRNA biogenesis: DGCR8, Dicer and TARBP2; RNA processing: YBX2; maternal factors: ZAR1; housekeeping: CTNNB1; pluripotency: DNMT3B, TERT and YY1; receptor: IGFR2; and transcription factor: BTF3 and NELF. In most cases, expression of these genes was higher in normal 1- and 2-cell embryos than in arrested 1- and 2-cell embryos.

Interestingly, certain gene categories were affected more in abnormal embryos than others. For example, in abnormal embryos, most of the housekeeping genes, hormone receptors and maternal factors were not appreciably altered in gene expression, whereas many genes involved in cytokinesis and miRNA biogenesis showed significantly reduced expression. Furthermore, among the genes that were affected, some genes showed a much larger difference between normal and abnormal embryos than others. For example, genes involved in the miRNA biogenesis pathway, such as DGCR8, Dicer and TARBP2, exhibited highly reduced expression levels in abnormal embryos. Notably, CPEB1 and Symplekin, two of the most severely affected genes, belonged to the same molecular mechanism that regulates maternal mRNA storage and reactivation by manipulating the length of a transcript's poly(A) tail (Bettegowda, A. et al. (2007) Front. Biosci. 12:3713-3726). These data suggest that embryo abnormality correlates with defects in the embryo's mRNA regulation program.

Correlating cytokinesis with gene expression profiles. Gene expression analysis was performed with genes that coded for key cytokinesis components. The identity of each embryo was tracked by installing a camera on the stereomicroscope and videotaping the process of sample transfer during media change and sample collection. When assessing the gene expression profiles of abnormal embryos, we observed a strong correlation between aberrant cytokinesis and lower gene expression level in key cytokinesis components. Interestingly, the gene expression profiles of abnormal embryos were as diverse and variable as their aberrant morphological phenotypes.

Figure 9:
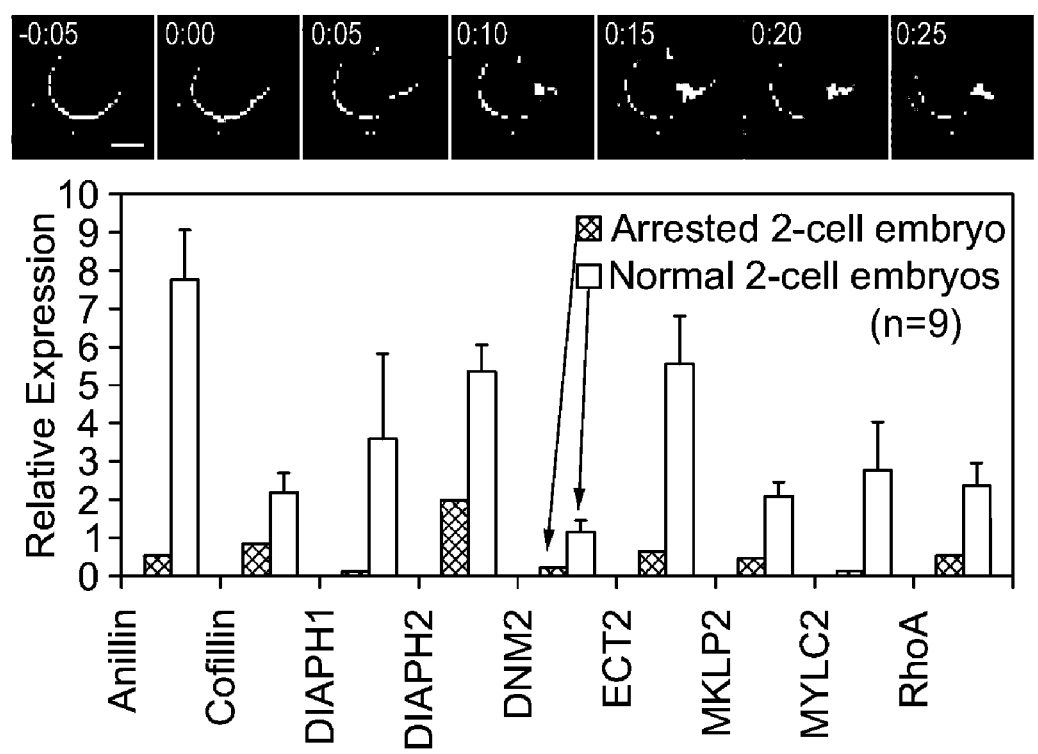
FIG. 9 is a bar graph showing expression levels of different genes in an arrested 2-cell embryo and normal 2-cell embryos. A select number of the time-lapse images for the arrested 2-cell embryo are shown at the top.
Figure 10:
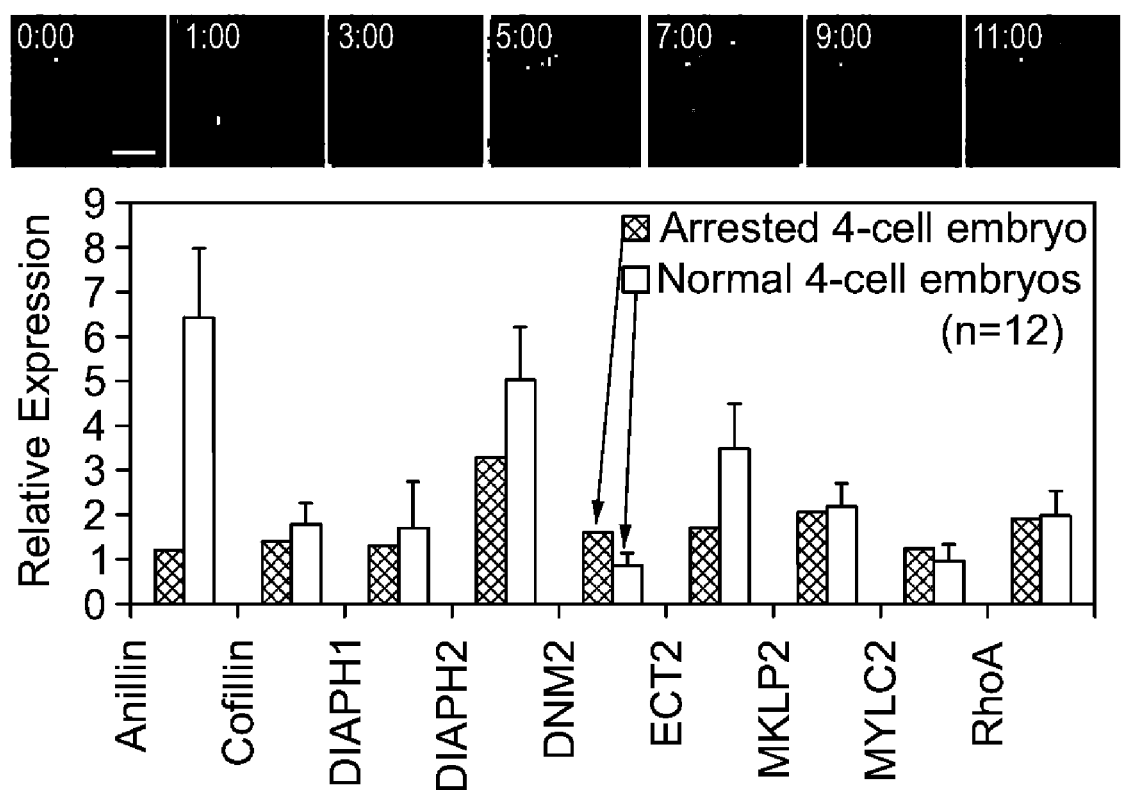
FIG. 10 is a bar graph showing a comparison of the same genes presented in FIG. 9, in an arrested 4-cell embryo and normal 4-cell embryos. A select number of the time-lapse images for the arrested 4-cell embryo are shown at the top.

It was discovered that cytokinesis gene expression varied as between normal 2-cell embryos and abnormal 2-cell embryos (FIG. 9) and as between normal and abnormal 4-cell embryos (FIG. 10). FIGS. 9 and 10 show relative expressions of genes which are more highly expressed in normal two cell human embryos (FIG. 9) and normal 4 cell embryos (FIG. 10), correlated with different cytokinesis phenotypes. As represented in FIG. 9, an arrested 2-cell embryo that showed abnormal membrane ruffling during the first cytokinesis had significantly reduced expression level of all cytokinesis regulatory genes tested. Genes showing differences in FIG. 9 are anillin, cofillin, DIAPH1, DIAPH2, DNM2, ECT2, MKLP2, MYCL2 and RhoA. The normal expression levels are given in the bars to the right and can be seen to be higher in each gene. In the photographs above the graphs of FIG. 9, showing abnormal two cell embryos, the scale bar represents 50 μm. FIG. 10 shows results from an arrested 4-cell embryo that underwent aberrant cytokinesis with a one-sided cytokinesis furrow and extremely prolonged cytokinesis during the first division showed decreased expression in the cytokinesis regulators Anillin and ECT2. Scale bar in FIG. 10 also represents 50 μm.

Figure 11:
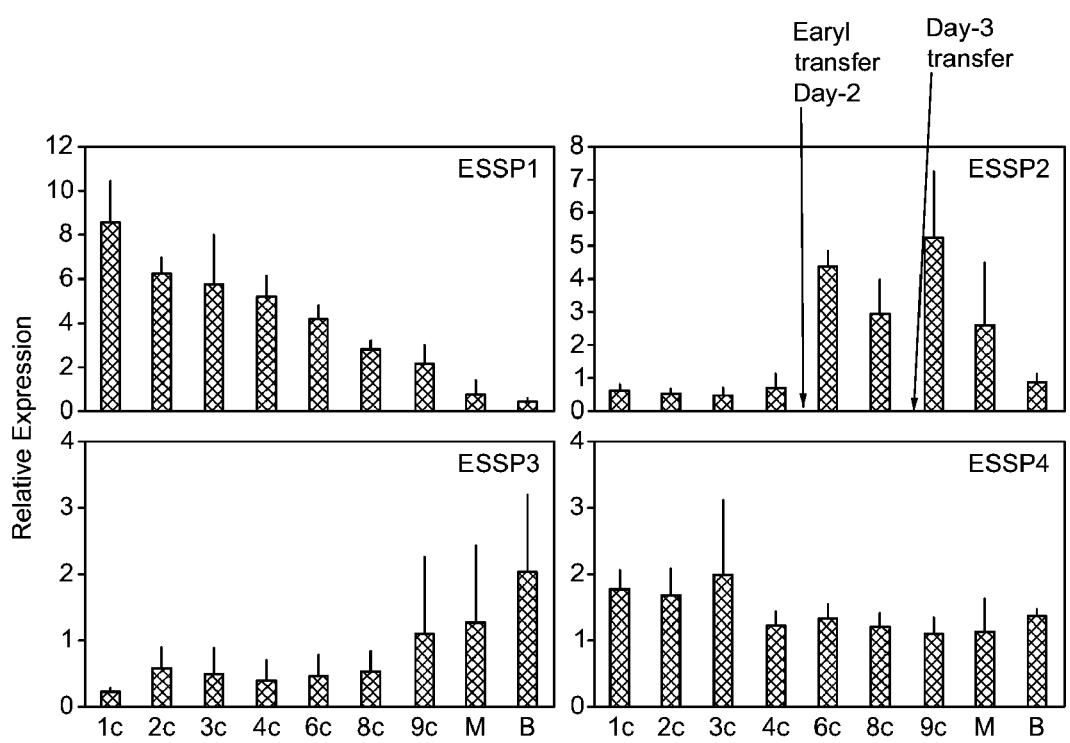
FIG. 11 is a series of bar graphs showing gene expression patterns (ESSP) having 4 distinct patterns. Indicated are times of early transfer prior to embryonic gene activation (day 2) and typical expression at day 3.

Embryonic stage specific gene expression patterns. FIG. 11 shows four Embryonic Stage Specific Patterns (ESSPs) that were identified during gene expression analysis of 141 normally developed single embryos and single blastomeres. The genes which fall into each one of the four ESSPs are listed in Table 2 (FIG. 20). The plots in FIG. 11 were created by grouping genes based on similar expression patterns and averaging their expression values (relative to reference genes). Relative expression level of an ESSP was calculated by averaging the expression levels of genes with similar expression pattern. Gene expression levels are plotted against different cell stages, i.e. 1c=one cell; M=morula, B=blastocyst. In FIG. 11, relative expression of genes in each of the four ESSPs is shown as a function of development, from 1-cell (1c) to morula and blastocyst. ESSP1 shows maternally inheritance, ESSP2 shows gene transcription activation, ESSP3 shows late stage activation, and ESSP4 shows persistent transcripts. As indicated on ESSP2, the typical transfer point in an IVF clinic occurs at day 3, when the embryos are undergoing significant developmental changes due to embryonic gene activation. Time-lapse image data indicates that the developmental potential of an embryo can be identified by the 4-cell stage, thereby allowing earlier transfer of embryos on day 2 and prior to this gene activation. This early transfer is useful for improving the success rate of IVF procedures.

Table 2 (FIG. 20) lists genes that belong to each of the four ESSPs identified. Relative gene expression level of each gene was calculated against the reference genes (GAPDH and RPLPO) and relative to the gene average. The expression pattern of each gene against the embryo's developmental timeline followed one of the four following ESSPs: ESSP pattern (1) Early-stage: genes that start high, slowly degrade, and turn off before blastocyst; ESSP pattern (2) Mid-stage: genes that turn on after 4-cell stage; ESSP pattern (3) Late-stage: genes that turn on at morula or blastocyst; and ESSP pattern (4) Constant: genes that have relatively constant expression values.

ESSP1 described the pattern of maternally inherited genes. These transcripts started with a high expression level at the zygote stage and subsequently declined as the embryos developed into blastocysts. The half-life of these transcripts was approximately 21 hours. Classical maternal factors from other model organisms, such as GDF9 and ZAR1, as well as germ cell (oocyte) specific genes VASA and DAZL fell under this category. ESSP2 included the embryonic activated genes, which were first transcribed in the embryos after the 4-cell stage. Some genes in this category appeared to display two waves of activation, the first and smaller one at the 5- to 6-cell stage, and the second and larger one at the 8-cell stage. Known EGA genes from other model organisms, such as EIF1AX31 and JARID1 B32, fell into this category. ESSP3 was comprised of late activated genes that were not expressed until the blastocyst stage, including the trophoblast marker GCM1. ESSP4 contained persistent transcripts that maintained stable expression relative to the reference genes throughout development. The half-life of these genes was 193 hours, approximately 9-fold longer than ESSP1. This category included a mixture of housekeeping genes, transcription factors, epigenetic regulators, hormone receptors and others. These 4 patterns of gene expression were confirmed in another experiment set using 61 samples of single normal embryos and blastomeres.

Abnormal embryos exhibiting aberrant cytokinetic and mitotic behavior during the first divisions, correlated with highly erratic gene expression profiles, especially in genes involved in embryonic RNA management. Thus, one may combine these methodologies to provide methods which may be used to predict pre-implantation embryo viability. Results suggest that abnormal embryos begin life with defective programs in RNA processing and miRNA biogenesis, causing excessive degradation of maternal mRNA. The stochastic nature of such unregulated RNA degradation leads to random destruction of transcripts, causing the wide variety of aberrant phenotypes observed in abnormal embryos. Decreased level of miRNAs cause defects in regulated maternal RNA degradation, leading to developmental arrest at different stages.

Individual blastomere analysis. In order to assess when molecular differentiation began in human preimplantation embryos, the expression level of CDX2 in single blastomeres harvested from 17 embryos at different developmental stages was analyzed. FIG. 12A shows the relative expression level of two genes, CTBBN1 (dark bars) and CDX2 (light bars) as a function of developmental stage, from 2 cell to blastocyst. As can be seen, CDX2 was expressed sporadically at low levels in some single blastomeres from embryos prior to the 4-cell stage (FIG. 12A). However, from the 6-cell stage onward, every embryo contained at least 1 blastomere that expressed CDX2 at a significant level. The expression level of the housekeeping gene CTNNB1 also shown in FIG. 12A remained constant among blastomeres from the same embryo, indicating that the heterogeneous expression pattern of CDX2 was not a qPCR artefact. Data from an independent experiment demonstrate similar observations. These results indicate that molecular differentiation in human preimplantation embryos might occur as early as immediately after the 4-cell stage.

Interestingly, inspection of gene expression profiles in single blastomeres revealed embryos that contained blastomeres with gene expression signatures corresponding to different developmental ages. The gene expression profile of any given embryo at any given time equals the sum of maternal mRNA degradation and EGA. A younger blastomere of early developmental age typically contains a high amount of maternal transcripts and a low amount of zygotic genes, and the opposite holds true for an older blastomere at a more advanced developmental age. In this experiment, the material program was defined as the average expression values of 10 ESSP1 markers (maternal transcripts), and the embryonic program by the average expression values of 10 ESSP2 markers (embryonic transcripts). The maternal transcript panel used includes DAZL, GDF3, IFITM1, STELLAR, SYCP3, VASA, GDF9, PDCD5, ZAR1 and ZP1, whereas the embryonic gene panel includes ATF7IP, CCNA1, EIF1 AX, EIF4A3, H2AFZ, HSP70.1, JARID1 B, LSM3, PABPC1, and SERTAD1. Among the 6 blastomeres successfully collected from this particular 8-cell embryo, 3 blastomeres displayed a gene expression signature similar to blastomeres from a normal 3-cell embryo sample, whereas the other 3 blastomeres were similar to blastomeres from a normal 8-cell embryo sample (FIG. 12B). The most likely explanation of this observation is arrest of a sub-population of cells within the embryo. This partial arrest phenotype was also observed in another 9-cell embryo and 2 morulas among the samples we tested. The fact that maternal transcript level remained high in the arrested blastomeres, which had spent the same amount of time in culture as their normal sister cells, indicates that degradation of maternal RNA is not a spontaneous process that simply occurs through time but most likely requires the functioning of specific RNA degradation mechanisms such as microRNAs (miRNAs). These data also provide further evidence that maternal mRNA degradation is a conserved developmental event during mammalian embryogenesis and is required for normal embryo development (Bettegowda, A., et al. (2008) Reprod. Fertil. Dev. 20:45-53). In addition, these data suggest that individual blastomeres in an embryo are autonomous and can develop independently of each other. Further, these results indicate that one may use the gene expression level tests described here to test for a level of an mRNA (which is indicative of gene expression level) in a cell to be tested, where the RNA is of a gene known to be part of the maternal program, and the persistence of such expression level in a later stage of embryonic development is correlated with a likelihood of abnormal outcome, or part of the embryonic program, where absence over time is indicative of a likelihood of an abnormal outcome. The maternal program genes examined here are ZAR1, PDCD5, NLRP5, H5F1, GDF9 and BNC2. Other maternal effect genes are known and may be used.

Embryonic gene activation. The present methods are at least in part based on findings that abnormal, developmentally arrested embryos frequently exhibit aberrant cytokinesis and mitotic timing during the first three divisions before EGA (embryonic gene activation) occurs. This suggests that the fate of embryo development is largely determined by maternal inheritance, a finding in remarkable accordance with a mathematical model of human preimplantation development performed by Hardy et al. in 200134. Moreover, anomalies of cytokinesis and mitosis strongly correlate with decreased levels of maternal transcripts in genes that regulate miRNA biogenesis and maternal mRNA masking, storage and reactivation. miRNAs regulate translation by promoting mRNA degradation in diverse biological processes, including organism development and differentiation (Blakaj, A. & Lin, H. (2008) J. Biol. Chem. 283:9505-9508; Stefani, G. & Slack, F. J. (2008) Nat. Rev. Mol. Cell. Biol. 9:219-230). Increasing evidence from model organisms show that miRNAs may be the key regulators of maternal transcript degradation in early embryos (Bettegowda, A., et al. (2008) Reprod. Fertil. Dev. 20:45-53). Thus, defects in miRNA biogenesis will likely lead to abnormal embryo development. On the other hand, failure to properly manage maternal mRNAs may also lead to poor embryogenesis. Mammalian oocytes synthesize a large pool of maternal RNA transcripts required to support early embryo growth before the mother's birth. These transcripts are repressed and stored for a prolonged period of time, until they are reactivated after fertilization. Defects in this maternal RNA management program will likely affect the amount and quality of the maternal transcripts and thus jeopardize the chance of successful development.

Figure 13:
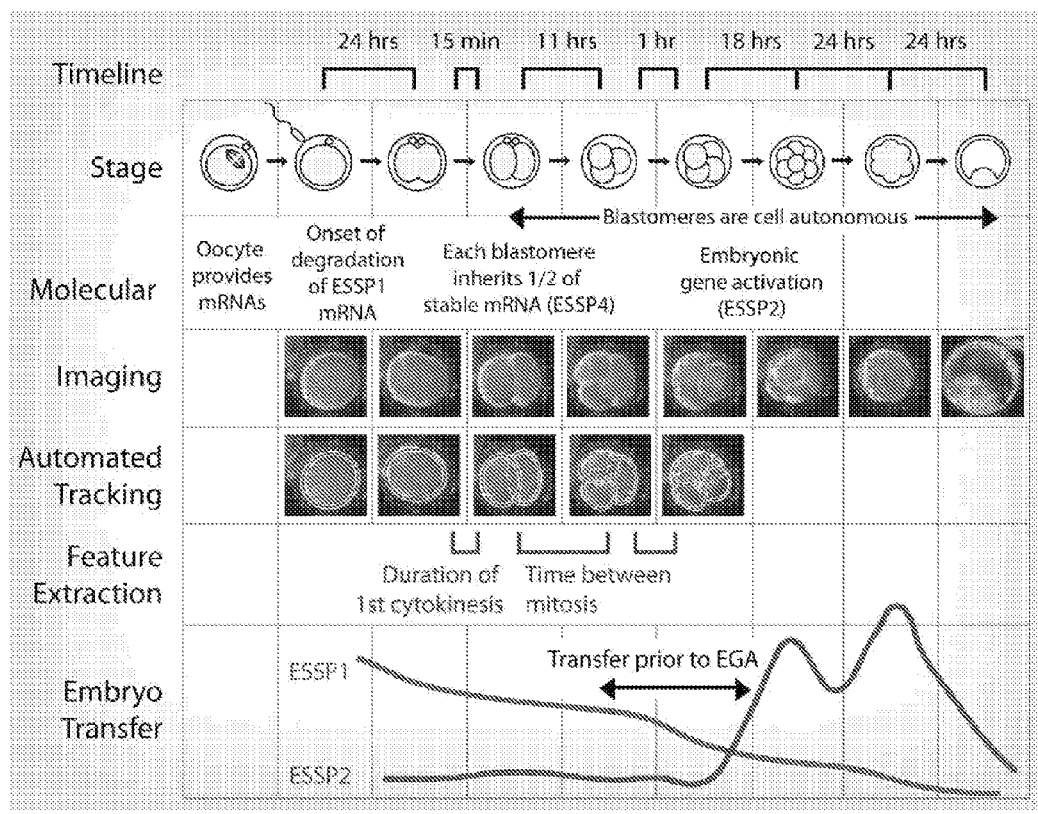
FIG. 13 is a drawing of a model for using time-lapse image analysis and correlated molecular analysis to assess embryo viability.

Model for assessing embryo viability. FIG. 13 shows a model for human embryo development based on correlated imaging and molecular analysis. Shown is the timeline of development from zygote to blastocyst including critical brief times for prediction of successful development to blastocyst and a diagram of embryo development. Key molecular data, as diagrammed, indicates that human embryos begin life with a distinct set of oocyte RNAs that are inherited from the mother. This set of RNAs is maintained and packaged properly by specific RNA management programs in the egg. Following fertilization, degradation of a subset of maternal RNAs specific to the egg (ESSP1; Embryonic Stage Specific Pattern 1) must be degraded as the transition from oocyte to embryo begins. In parallel, other RNAs are ideally partitioned equally to each blastomere as development continues (ESSP4). The successful degradation and partitioning of RNAs culminates with embryonic genome activation (EGA) and transcription of the genes of ESSP2 in a cell autonomous manner. Notably, during the cleavage divisions, embryonic blastomeres may arrest or progress independently. The outcome of cell autonomous development in the embryo is that individual blastomeres may arrest or progress and as the 8-cell embryo progresses to morula stage and beyond, blastocyst quality will be impacted by the number of cells that arrested or progressed beyond 8 cells. Imaging data demonstrates that there are critical periods of development that predict success or failure: first cytokinesis, the second cleavage division and synchronicity of the second and third cleavage divisions. These parameters can be measured automatically using the cell tracking algorithms and software previously described. The systems and methods described can be used to diagnose embryo outcome with key imaging predictors and can allow for the transfer of fewer embryos earlier in development (prior to EGA).

Example 3

Imaging oocyte maturation and subsequent embryo development.

Results

One of the major limitations of current IVF procedures is oocyte quality and availability. For example, current IVF protocols recruit oocytes from the small cyclic pool, providing a small number of oocytes (e.g. 1-20) for fertilization. Moreover, approximately 20% of oocytes retrieved following hormone stimulation during IVF procedures are classified as immature, and are typically discarded due to a reduced potential for embryo development under current culture conditions.

Figure 14:
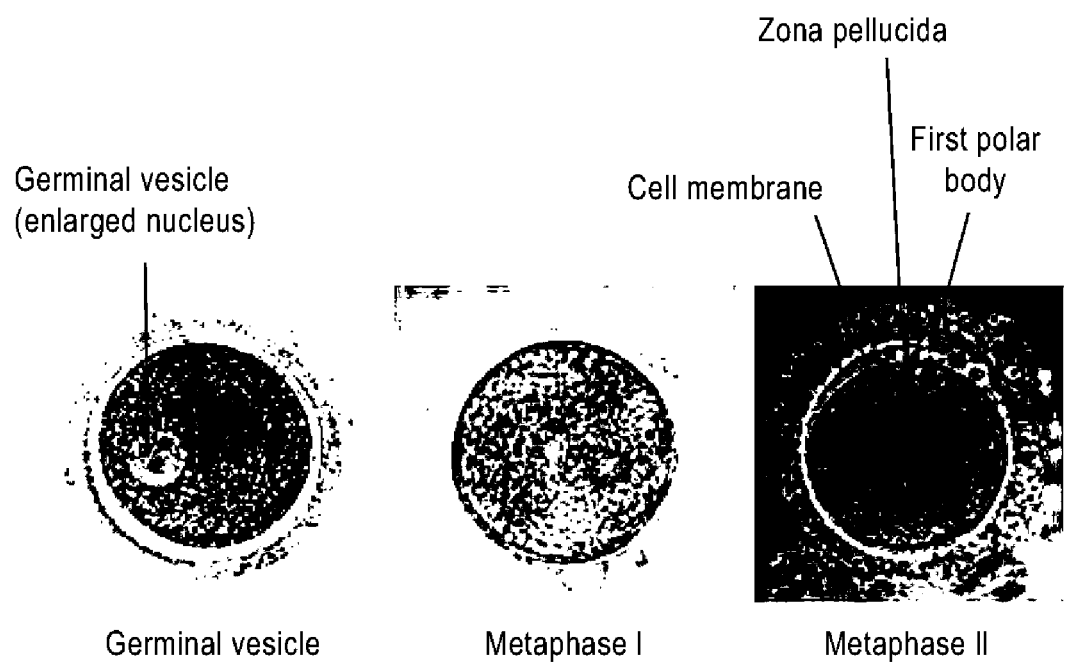
FIG. 14 is a series of photographs showing three stages of development during in vitro oocyte maturation.
Figure 15:
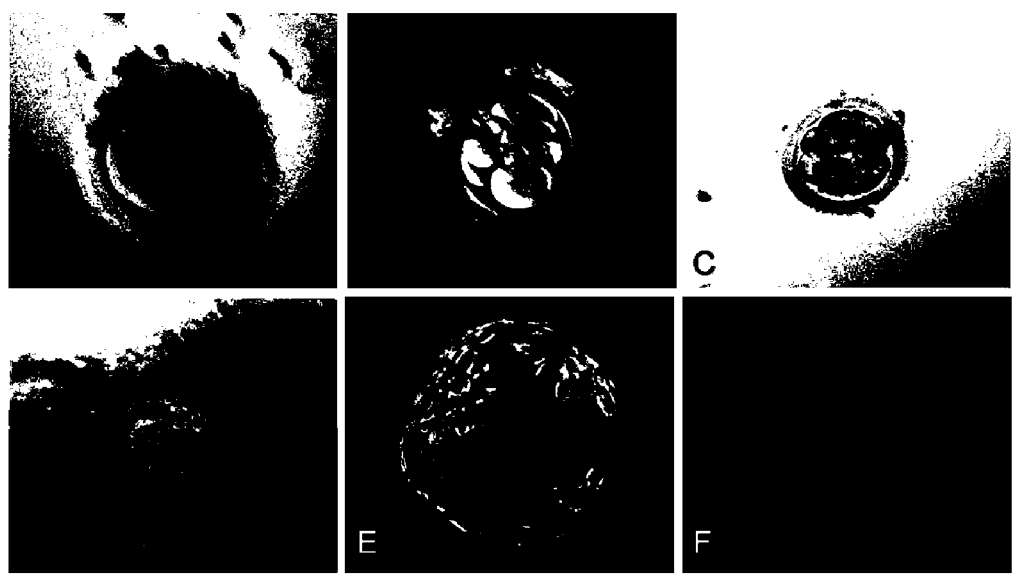
FIG. 15 is a series of photographs showing the process of embryo development after in vitro oocyte maturation.
Figure 16:
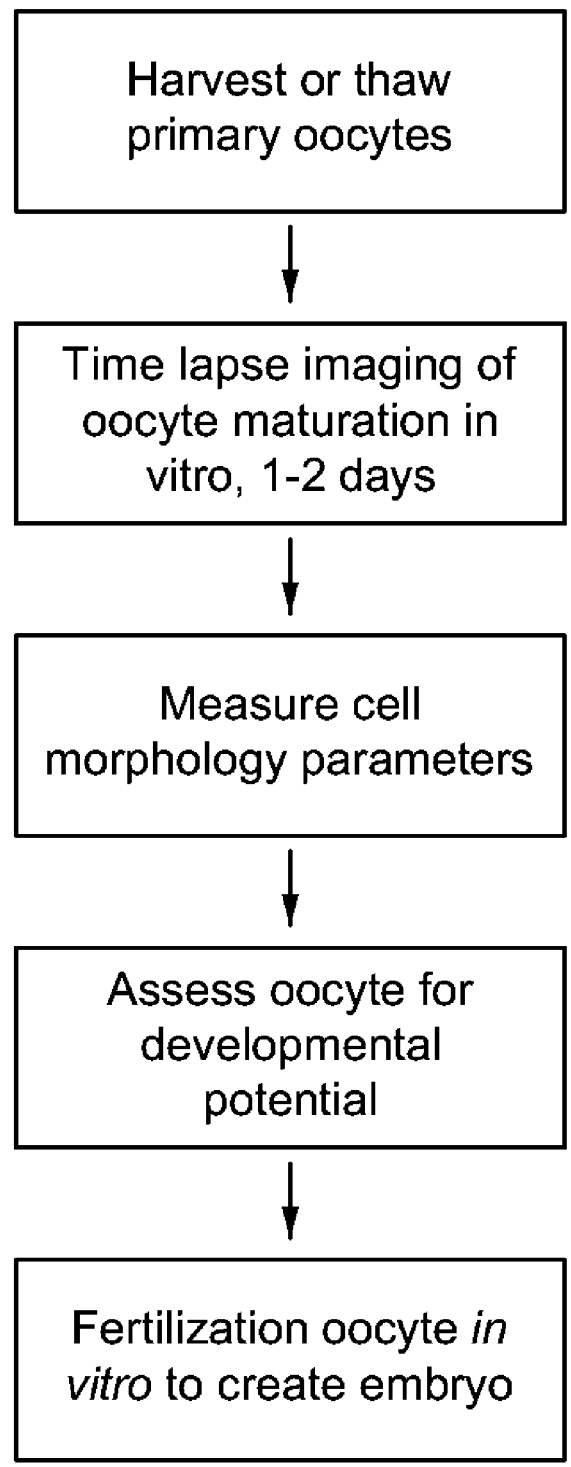
FIG. 16 is a flow chart showing processes used to assess oocytes.

One method to increase the oocyte pool is through in vitro maturation. FIG. 14 shows three stages of development during in vitro maturation, including germinal vesicle, metaphase I, and metaphase II. The germinal vesicle and metaphase I stages are classified as immature oocytes, while metaphase II is classified, as mature due to the presence of the first polar body, which occurs at 24-48 hours after initiating in vitro maturation. FIG. 15 shows embryo development of an oocyte that has been matured in vitro.

Another method, to increase the oocyte pool is recruit oocytes from the primary and secondary pool, providing up to several thousands of oocytes. In this procedure, dormant follicles are recruited from the ovary and programmed in vitro to produce oocytes with normal chromosome composition, epigenetic status, RNA expression, and morphology. In other aspects, the oocytes may be derived from pluripotent stem cells differentiated in vitro into germ cells and matured into human oocytes.

As illustrated in FIG. 14, the maturation process of an oocyte in vitro is marked by several cellular changes that may be used to define cellular parameters for measurement and analysis in the methods of the subject invention. These include, for example, changes in morphology of the oocyte membrane, e.g. the rate and extent of separation from the zona pellucida; changes in the morphology of the oocyte nucleus, e.g. the initiation, completion, and rate of germinal vesicle breakdown (GVBD); the rate and direction of movement of granules in the cytoplasm and nucleus; and the movement of and extrusion of the first polar body.

Example 4

Imaging stem cell differentiation.

Results

Figure 17:
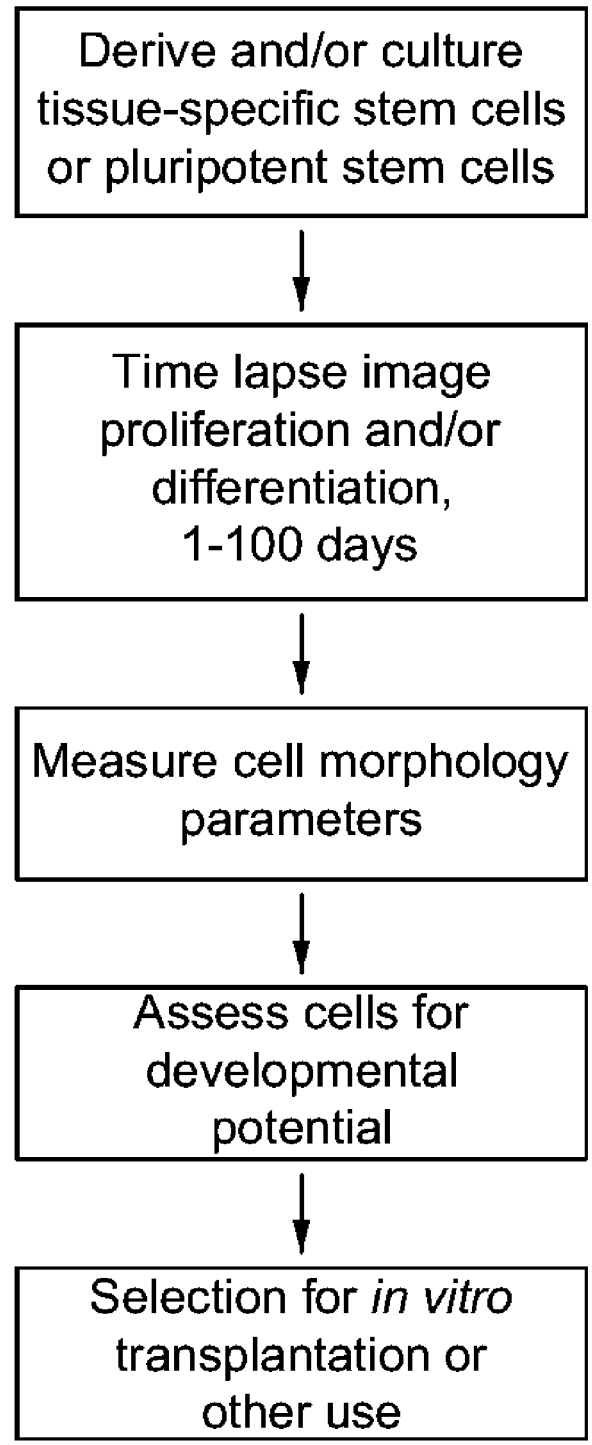
FIG. 17 is a flow chart showing processes used to assess stem cells and pluripotent stem cells.

Time-lapse image analysis can also be used to assess the viability, developmental potential, and outcome of other types of cells, such as stem cells, induced pluripotent stem cells (iPSCs), and human embryonic stem cells (hESCs). The developmental potential of stem cells can be assessed by using time-lapse image analysis to measure changes in morphology during cell development and differentiation (FIG. 17). The differentiated cells can then be analyzed and selected for in vivo transplantation or other use. Several parameters of stem cells may be extracted and analyzed from time-lapse image data, such as the duration of cytokinesis, time between mitosis events, cell size and shape, number of cells, motion of cells, division patterns, differentiation, asymmetric division (where one daughter cell maintains a stem cell while the other differentiates), symmetric division (where both daughter cells either remain as stem cells or both differentiate), and fate specification (determining precisely when a stem cell differentiates).

The basic formula of stem cell therapy is that undifferentiated stem cells may be cultured in vitro, differentiated to specific cell types, and subsequently transplanted to recipients for regeneration of injured tissues and/or organs. Time-lapse image analysis can be used as a high-throughput non-invasive device to identify stem cells that form non-tumorigenic differentiated progeny capable of integration into mature tissues. Potential applications include the treatment of neurological disorders such as Alzheimer's and Parkinson's, vascular system disorders and heart diseases, muscular and skeletal disorders such as arthritis, autoimmune diseases and cancers, as well as drug discovery by evaluating targets and novel therapeutics.

Figure 18:
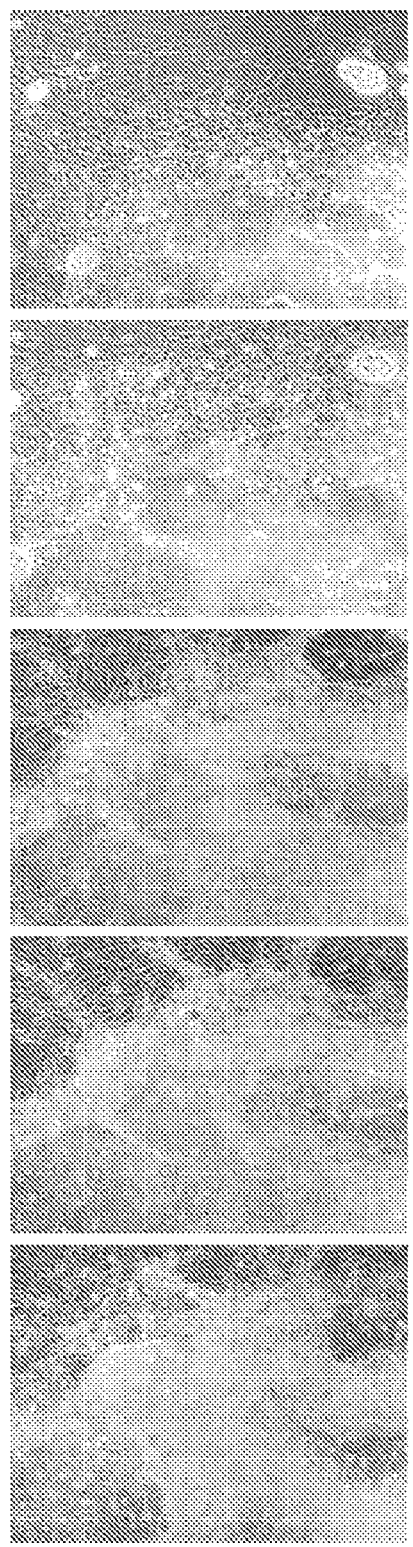
FIG. 18 is a series of photographs showing the process of induced pluripotent stem cells differentiating into neuron rosettes.

In humans, damaged tissues are generally replaced by continuous recruitment and differentiation from stem cells in the body. However, the body's ability for regeneration is reduced with aging. One example of this is urinary incontinence resulting from sphincter deficiency. Aging is believed to be one of the principal causes of sphincter deficiency because the number of muscle fibers and nerves density diminish with age. In order to treat patients with incontinence, iPSCs may be derived from fibroblast cultured from vaginal wall tissues in order to produce differentiated smooth muscle cells. These differentiated cells can then be transplanted in vivo. Prior to transplantation, time-lapse image analysis can be used to characterize the iPSCs with respect to pluripotency, differentiation, methylation, and tumorigenicity. Other applications include time-lapse imaging of iPSCs that are derived from skin cells of patients with Parkinson's and differentiated into neurons for transplantation (FIG. 18).

Example 5

Validation of Imaging Parameters Through Automated Analysis

As evidenced by our time-lapse image data, human embryo development is a highly variable process between embryos within a cohort and embryos can exhibit a wide range of behaviours during cell division. Thus, the manual characterization of certain developmental events such as the duration of highly abnormal cytokinesis (FIG. 4) may be subject to interpretation. To validate our imaging parameters and the ability to systematically predict blastocyst formation, we developed an algorithm for automated tracking of cell divisions up to the 4-cell stage. Our tracking algorithm employs a probabilistic model estimation technique based on sequential Monte Carlo methods. This technique works by generating distributions of hypothesized embryo models, simulating images based on a simple optical model, and comparing these simulations to the observed image data (FIG. 21a).

Embryos were modeled as a collection of ellipses with position, orientation, and overlap index (to represent the relative heights of the cells). With these models, the duration of cytokinesis and time between mitosis can be extracted. Cytokinesis is typically defined by the first appearance of the cytokinesis furrow (where bipolar indentations form along the cleavage axis) to the complete separation of daughter cells. We simplified the problem by approximating cytokinesis as the duration of cell elongation prior to a 1-cell to 2-cell division. A cell is considered elongated if the difference in axes lengths exceeds 15% (chosen empirically). The time between mitosis is straightforward to extract by counting the number of cells in each model.

Figure 21:
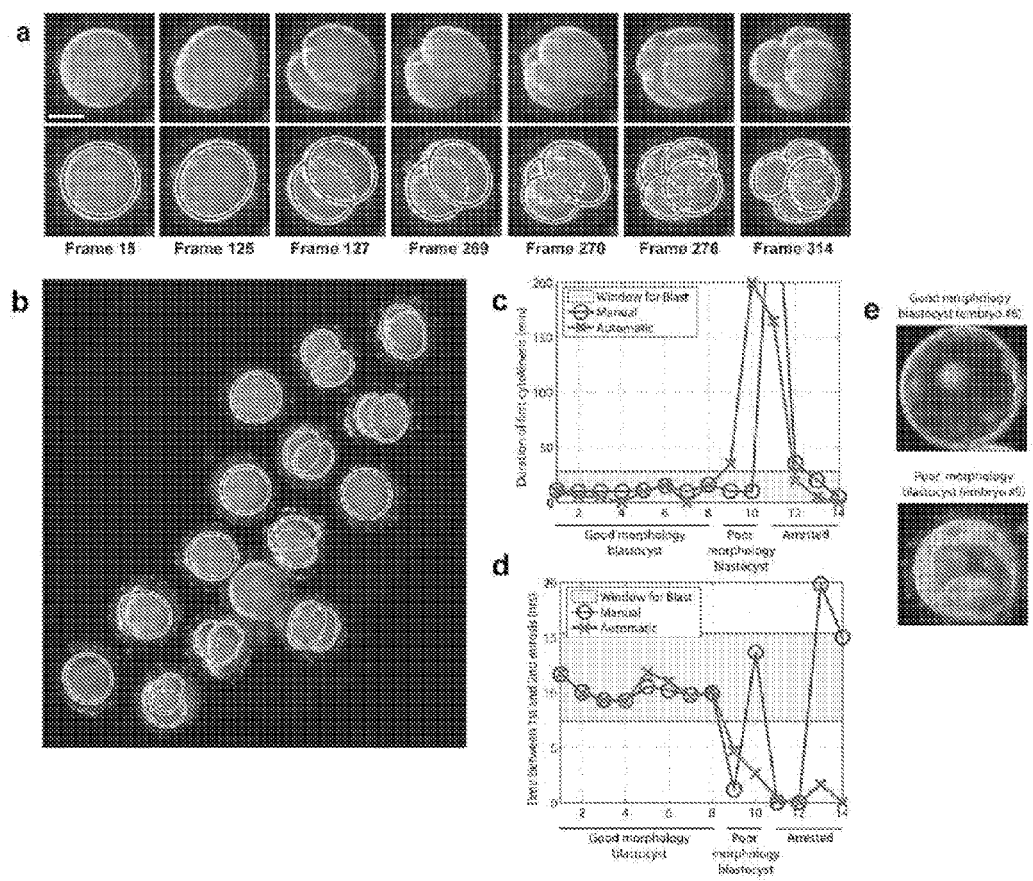
FIG. 21 shows automated image analysis demonstrating the ability of imaging parameters to predict blastocyst formation. (A) Shows the results of the tracking algorithm for a single embryo. (B) Shows a set of 14 embryos that were analyzed. (C) Shows the comparison of manual image analysis to automated image analysis for the duration of cytokinesis (D) Shows the comparison of manual image analysis for the time between first and second mitosis. (E) Shows the comparison of good blastocyst morphology to bad blastocyst morphology.

We tested our algorithm on a set of 14 human embryos (FIG. 21b) and compared the automated measurements to manual image analysis (FIG. 21c, FIG. 21d). In this data set, 8 of the 14 embryos reached the blastocyst stage with good morphology (FIG. 21e top). The automated measurements were closely matched to the manual measurements, and all 8 embryos were correctly predicted to reach blastocyst. 2 of the 14 embryos reached blastocyst with poor morphology (poor quality of inner cell mass; FIG. 21e bottom). For these embryos, manual assessment indicated that 1 would reach blastocyst and 1 would arrest, while the automated assessment predicted that both would arrest. Finally, 4 of the 14 embryos arrested prior to the blastocyst stage, and were all correctly predicted to arrest by both methods.

Particle Filter Framework

The particle filter is a model estimation technique based on Monte Carlo simulation. It is used to estimate unknown or "hidden" models by generating distributions of hypothesized models and comparing these models to observed data. Its ability to accommodate arbitrary motion dynamics and measurement uncertainties makes it an ideal candidate for tracking cell divisions.

The particle filter tracks the propagation of three main variables over time: the state x, the control u, and the measurement z. The state variable x is a model of the embryo we wish to estimate and is represented as a collection of ellipses (for 2D) or ellipsoids (for 3D). The control variable u is an input that transforms the state variable and consists of our cell propagation and division model. The measurement variable z is an observation of the state and consists of our images acquired by the time-lapse microscope. These parameters are described in greater detail in the following sections.

An estimate of the current state x at each time step t is represented with a posterior probability distribution. This posterior is often referred to as the belief and is defined as the conditional probability of the current state $x_t$ given all past image measurements $z_{1:t}$ and past controls $u_{1:t}$.

$$\mathrm{bel}(x_t) = p(x_t | u_{1:t}, z_{1:t}).$$

The particle filter approximates the posterior with a set of weighted samples, or particles, denoted as:

$$x_t = x_t^{[1]}, x_t^{[2]}, \ldots, x_t^{[M]},$$

where M is the number of particles. The terms particles and embryo models are used interchangeably herein. Thus, a single particle $x_t^{[m]}$ (where $1 \leq m \leq M$) is one hypothesis of the embryo model at time t.

After initialization, the particle filter repeatedly applies three steps. The first step is prediction, where each particle is propagated using the control input:

$$x_t^{[m]} \sim p(x_t | u_t, x_{t-1}^{[m]}).$$

The resulting set of particles is an approximation of the prior probability. The second step is measurement update, where each particle is assigned an importance weight corresponding to the probability of the current measurement:

$$w_t^{[m]} = p(z_t | x_t^{[m]}).$$

The set of weighted particles is an approximation of the posterior bel(xt).

A key component of the particle filter comes in the third step, where the set of particles is re-sampled according to their weights. This re-sampling step focuses the particle distribution in the region of highest probability.

Cell Representation

Cells are represented as ellipses in 2D space. Each cell has a major axis, minor axis, and 2-dimensional position in Cartesian coordinates, given by the equation:

$$\frac{(x-x_0)^2}{a^2} + \frac{(y-y_0)^2}{b^2} = 1.$$

Each ellipse also has a heading direction θ (yaw), which allows it to rotate in the x-y plane. Since ellipses almost always overlap with one another, we also denote an overlap index h, which specifies the order of overlap (or the relative height of the cells). The parameters for each embryo model at time t are therefore given as:

$$x_t^{[m]} = \begin{bmatrix} x_{0_1} & y_{0_1} & a_1 & b_1 & \theta_1 & h_1 \\ x_{0_2} & y_{0_2} & a_2 & b_2 & \theta_2 & h_2 \\ \vdots & \vdots & \vdots & \vdots & \vdots & \vdots \\ x_{0_N} & y_{0_N} & a_N & b_N & \theta_N & h_N \end{bmatrix},$$

where N is the number of cells in that model.

Cell Perturbation and Division

The first step of the particle filter is prediction, where each particle is propagated using the control input. For our application, there are two types of behavior that we want to model. The first type of behavior includes cell motion, which includes translation, rotation about the yaw angle, and changes in length of the major and minor axes. The second type of behavior is cell division, where a cell splits into two new cells.

To model cell motion, our control input takes a particle and randomly perturbs each value for each cell: $x_{0i}, y_{0i}, a_i, b_i, \theta_i$. The perturbation is randomly sampled from a normal distribution with relatively small variance (typically set to 5% of the initialized values).

To model cell division, we use the following approach. At a given point in time, for each particle, we assign a 50% probability that one of the cells will divide. This value was chosen empirically, and spans a wide range of possible cell divisions while maintaining good coverage of the current configuration. If a division is predicted, then the dividing cell is chosen randomly. A more sophisticated model could take into account additional factors such as the number of cells in a particle and the history of their division patterns, and could potentially create models based on observed behavior from real data.

When a cell is chosen to divide, a symmetric division along the major axis of the ellipse, producing two daughter cells of equal size and shape is applied. Each value for the daughter cells is then randomly perturbed. The perturbation is again sampled from a normal distribution but with a larger variance (10% of the initialized values) to accommodate large variability in the new cell shapes. Finally, the overlap indices of the two daughter cells are randomly selected while maintaining their collective overlap relative to the rest of the cells.

Image Simulation

After applying the control input to each particle, the particle representation must be converted into a simulated image that can be compared to the real images. Accurate image simulation can be a difficult task, and often requires the use of ray-tracing techniques and optical models. Rather than attempt to simulate realistic images, the method of the present invention focuses on simulating features that are easily identifiable in the images. Specifically, images of cell membranes are simulated.

There are two physical observations that must be taken into account. First, although the microscope is focused on a single plane through the embryo, the depth of field is quite large and out-of-focus light is collected from almost the entire embryo. And second, the embryos are partially transparent, which means that the membranes of cells at the bottom of the embryo can sometimes (but not always) be seen through the cells at the top of the embryo.

With these physical observations in mind, there is now described the image simulation model. For each cell, its corresponding elliptical shape is projected onto the simulated image using the overlap index h. The corresponding pixel values are set to a binary value of 1 and dilated to create a membrane thickness comparable to the observed image data.

The overlap index h specifies the order in which cells lie on top of one another. Since occluded cell membranes are only visible sometimes, if occluded points are detected, they are placed in the simulated image with low probability (typically around 10%). In practice, while these occluded membrane points are necessary for accurate shape modeling, it is important to make them sparse enough so that they do not resemble a visible edge.

Image Pre-Processing

The measurement variable z will now be described. A goal of the method of the present invention is to extract binary images of cell membranes from the microscope images for comparison to the simulated images. These membranes exhibit high curvature and high contrast, but are not easily extracted using intensity or color-based thresholding techniques. Accordingly, a principle curvature-based detector is employed. This method uses the Hessian operator:

$$H(s, \sigma) = \begin{pmatrix} I_{xx}(s, \sigma) & I_{xy}(s, \sigma) \\ I_{xy}(s, \sigma) & I_{yy}(s, \sigma) \end{pmatrix},$$

where Ixx, Ixy, and Iyy, are second-order partial derivatives evaluated at pixel location s and Gaussian scale σ. The eigenvalues of the 2×2 Hessian matrix provide information about principle curvatures, while the sign of the eigenvalues distinguish "valleys" from "ridges"43. To detect bright peaks or ridges, the principle curvature at each pixel is calculated as $$P(s)=|\min(\lambda_2,0)|,$$

where λ2 is the minimum eigenvalue. To detect membranes of varying thickness, the Hessian operator over a range of scales (i.e. σ min<=σ<=σ max) is applied, and the maximum curvature over this range is extracted. Finally, the Hessian image is thresholded to create a binary image of the extracted cell membranes. The threshold level is typically set to twice the standard deviation of the pixel values in the Hessian.

Particle Weights

As described in the section entitled "Particle Filter Framework," the second main step of the particle filter is measurement update, where particles are assigned an importance weight corresponding to the probability of the current measurement given a particular model. In our case, the importance weight is determined by comparing the pre-processed microscope image discussed above," to the simulated image also discussed above.

This problem has been investigated previously, where particle filter weights were calculated by comparing simulated images to actual images using normalized mutual information. This approach is similar to the idea of occupancy grid matching, which searches for pixel locations that are either both occupied (value 1) or both empty (value 0). These methods can have trouble when the simulated and actual images are similar in shape but slightly misaligned. Instead, the method being described uses a likelihood function based on the chamfer distance, which measures the average value of the closest distances from one point set to another. Two sets of points A (in the set of real numbers of size m), and B (in the set of real numbers of size n), corresponding to the non-zero pixels in the simulated image and actual image, respectively, are defined. The forward chamfer distance from the point set A to B is given as:

$$d(A, B) = \frac{1}{m} \sum_{a_i \in A} \min_{b_j \in B} \|a_i - b_j\|.$$

The backward chamfer distance is defined similarly. The present method employs symmetric chamfer distance, which provides a measure of how well the simulated image matches the actual image, as well as how well the actual image matches the simulated image:

$$d_{sym}(A,B)=d(A,B)+d(B,A).$$

In practice, the individual distance measurements are truncated to reduce the influence of noise. To reduce computation time, distances are determined by looking up pixel locations in distance transforms of the images.

The chamfer distance is used as a likelihood measure of our data measurement given the estimated model. That is, at time t, for a given image measurement $z_t$ and a particle model $xt_{[m]}$, the particle importance weight is given as:

$$w_t^{[m]} \propto \exp[-\lambda \cdot d_{sym}(z_t, x_t^{[m]})].$$

The constant λ is typically set to 1 and can be varied to control the "flatness" of the likelihood distribution.

Particle Re-Sampling and Dynamic Allocation

The third main step of the particle filter is re-sampling, where particles are selected in proportion to their weight to create a new set of particles. Particles with low probability are discarded, while particles with high probability are multiplied. There has been much prior work on developing efficient algorithms for re-sampling. The present method uses the low variance approach.

An important issue in particle filters is the choice of the number of particles. The simplest choice is to use a fixed value, say M=1000. Then, for each time step, the set of M particles is transformed into another set of the same size. In the context of the application, there can be relatively long periods of time during which the cells are inactive or just slightly changing size and position. Advantage of this observation is taken to reduce the processing load by dynamically allocating the number of particles according to the amount of cell activity. That is, when the cells are active and dividing, we increase the number of particles, and when the cells are inactive, we reduce the number of particles.

Figure 30:
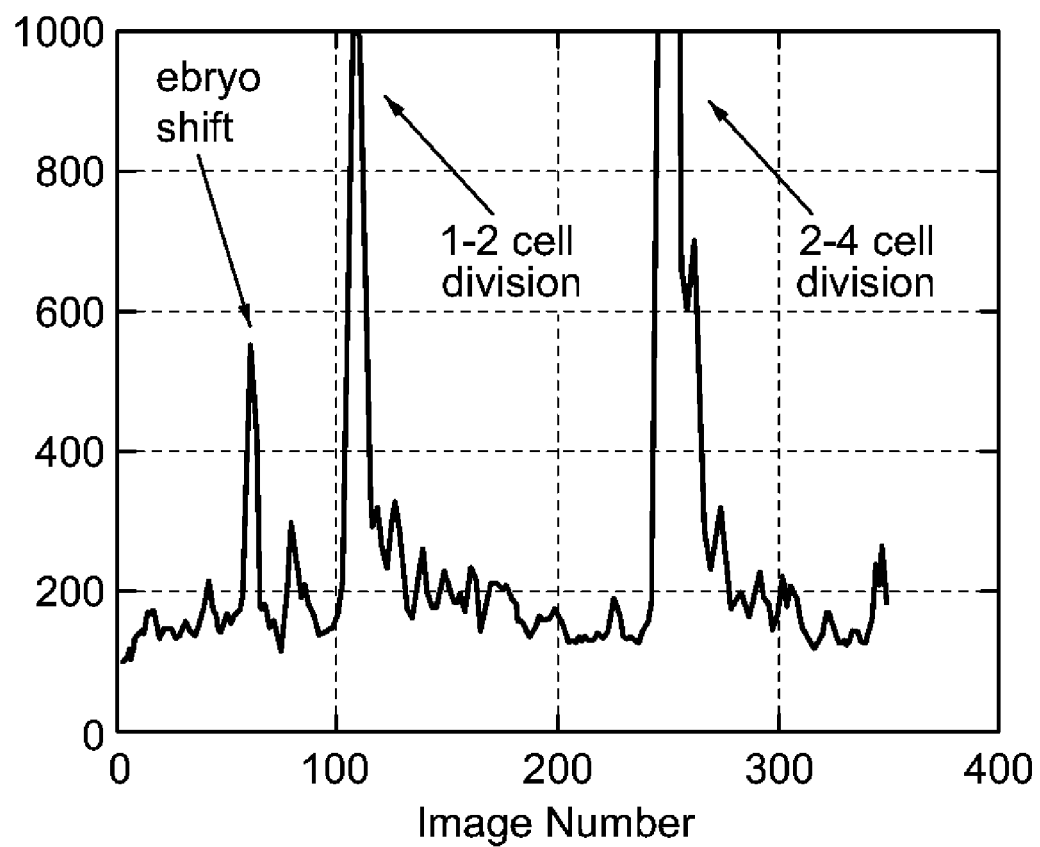
FIG. 30 is a graph showing the difference in pixel intensities between successive pairs of images during embryo development. This can be used on its own to assess embryo viability, or as a way to improve other algorithms, such as a particle filter, by determining how many particles (predicted embryo models) should be used.

To measure the degree of cell activity, the sum-of-squared differences (SSD) in pixel intensities between the new image (acquired by the microscope) and the previous image is calculated. To reduce noise, the images are first smoothed with a Gaussian filter, and the SSD value is smoothed over time with a causal moving average. The number of particles is then dynamically adjusted in proportion to this value and truncated to stay within the bounds 100<M<1000. FIG. 30 is a graph which shows how the number of particles could be allocated for an embryo dividing from the 1-cell to 4-cell stage. It should be noted that this method merely provides a measure of the amount of "activity" in the image, but does not distinguish between cell division and embryo motion (translation and/or rotation) because a prior image registration was not performed. In this situation (determining the number of particles) this is acceptable since the number of particles should increase in either event. In practice, we also adjust the number of particles based on the number of cells in the most likely embryo model. That is, more particles are generated when more cells are believed to be present in the images.

Limitations of Two-Dimensional Tracking

The 2D cell tracking algorithm described above is useful for determining the number of cells in the embryo as well as their 2D shapes. However, it is limited by the fact that there is no underlying physical representation. This may or may not be important for automatically tracking cell divisions in order to assess embryo viability. For example, certain parameters such as the duration of cytokinesis, and the time between cell divisions, can be measured using the 2D cell tracking algorithm. In the next section we extend our 2D model to 3D. To deal with occlusions and depth ambiguities that arise from estimating 3D shapes from 2D images, geometric constraints and constraints on conservation of cell volume are applied.

Cell Representation and Three Dimensional Tracking

This section describes an algorithm for 3D tracking of cell division. Many of the steps from the 2D algorithm carry over into this algorithm, with a few key exceptions. There is a new cell representation for 3D use. Cells are now represented as ellipsoids in 3D space, given by the equation:

$$\frac{(x-x_0)^2}{a^2} + \frac{(y-y_0)^2}{b^2} + \frac{(z-z_0)^2}{c^2} = 1.$$

Each ellipsoid also has a heading direction $\theta$, pitch $\psi$, and roll $\alpha$. Thus, the representation of each embryo model at time t is given as:

$$x_t^{[m]} = \begin{bmatrix} x_{0_1} & y_{0_1} & z_{0_1} & a_1 & b_1 & c_1 & \theta_1 & \psi 1 & \alpha_1 \\ x_{0_2} & y_{0_2} & z_{0_2} & a_2 & b_2 & c_2 & \theta_2 & \psi 2 & \alpha_2 \\ \vdots & \vdots & \vdots & \vdots & \vdots & \vdots & \vdots & \vdots & \vdots \\ x_{0_N} & y_{0_N} & z_{0_N} & a_N & b_N & c_N & \theta_N & \psi_N & \alpha_N \end{bmatrix}$$

One important effect of this revised model is that there can be ambiguities associated with inferring 3D shapes from 2D images. For example, a cell that is spherical in shape would have a similar appearance to a cell with a longer major axis and larger pitch rotation. This is not a major concern, since as will be shown later on, particle distribution will maintain these multiple hypotheses until enough information is available to make a distinction (e.g., from an event such as cell division).

Ellipsoids are considered rigid; that is, deformation is not explicitly modeled. However, we allow a small amount of overlap between neighboring ellipsoids, and in these regions of overlap we assume that the cells are flattened against each other. This is an important consideration since it is commonly observed in the embryos, and we account for it in the following sections.

Cell Perturbation and Division

Our 3D cell division and perturbation model is similar to the model in Section 4, "Cell Perturbation and Division," with a few key exceptions. The estimate of 3D shape can be used to enforce conservation of volume. This prevents cells from growing arbitrarily large, particularly in the z-direction. Volume conservation is applied in two situations. First, for cell perturbation, the axes a and b are varied, and c calculated such that volume is conserved for that individual cell. Second, for cell division, the following constraint is applied:

$$\frac{4}{3}\pi a_p b_p c_p = \frac{4}{3}\pi(a_{d_1} b_{d_1} c_{d_1} + a_{d_2} b_{d_2} c_{d_2}).$$

where the subscript p denotes a parent cell and the subscripts d1 and d2 denote the two daughter cells. In practice, we allow for a slight violation of these constraints by letting the total volume of the embryo fluctuate between plus/minus 5% of the original volume. This is used to compensate for potential inaccuracies in the initial volume estimate.

When a cell is chosen to divide in 3D, its division is modeled in the following way. First, for the chosen single cell, a division along the long axis of the ellipse, which could be either a, b, or c depending on the configuration, is applied. The daughter cells are initialized to be equal in size and spaced evenly apart, taking into account the rotation of the parent cell. Their parameters are then perturbed to cover a wide range of possible configurations, again using a normal distribution with variance set to 10% of the initialized values.

Geometric Constraints

The issues of occlusion and depth ambiguity are partially mitigated through conservation of volume. However, constraints regarding the spatial relationships of neighboring ellipsoids are also needed. The first constraint is that cells are prohibited from overlapping by more than 20% in radius. For cells that overlap by an acceptable amount, the assumption that they have flattened against each other is made. The particle model being described represents this phenomenon by ignoring points inside intersecting ellipsoids during image simulation. This was empirically motivated and correlates well with physically observed behavior.

A second constraint that keeps cells in close proximity is imposed. This constraint is directly related to the physical behavior of human embryos, where cells are constrained by a membrane called the zona pellucida. The zona is modeled as a spherical shell and use it to impose boundary conditions. The radius of the zona is set to 30% larger than the radius of the 1-cell embryo.

These constraints are enforced as follows. For each particle at a given time, a random control input is applied to generate a new particle, as discussed above. If either of the physical constraints has been violated, the new particle is discarded and a new random control is applied. If a satisfactory new particle is not generated after a certain number of attempts, then that particle is discarded.

Image Simulation

The advantage of darkfield illumination, used in the examples, is that cell membranes scatter light more than the cell interior. This effect is most pronounced at locations where the cell membranes are parallel to the optical axis (z-axis). Accordingly, to simulate images these locations are searched for in our 3D models, which are not necessarily located at the equators of the ellipsoids due to their rotation. The same rules regarding visible and occluded edges, as discussed above, are then followed.

Cell Tracking Example in 2D

This example pertains to automated cell microscopy and uses the above described algorithm for 2D tracking of cell divisions. This model is designed to track the number of cells in the image as well as the 2D contours of cell membranes. The first step is image acquisition, which motivates subsequent sections such as image simulation and image pre-processing. Time-lapse image sequences for this example were acquired with a custom Olympus IX-50 inverted microscope with a 10× objective. The microscope is modified for darkfield illumination, where a hollow cone of light is focused on the sample by placing a circular aperture between the light source and condenser lens. The objective lens collects light that is scattered by the sample and rejects directly transmitted light, producing a bright image on a dark background. An advantage of darkfield illumination is that cell membranes tend to scatter light more than the cell interior, thereby enhancing their contrast. The microscope is outfitted with a heated stage and custom incubation chamber to allow culturing of the embryos over a period of up to 5 or 6 days. Images were captured at 5-minute intervals by an Olympus SLR digital camera mounted on the side port of the IX-50.

Imaging of embryos began when they were zygotes, or fertilized eggs with roughly spherical shape. To initialize the set of particles, the thresholded Hessian is computed as described in Section 6, "Image Pre-Processing," and fit a circle to it using least squares. All particles are then initialized as circles with random orientations sampled from a uniform distribution.

Figure 31:
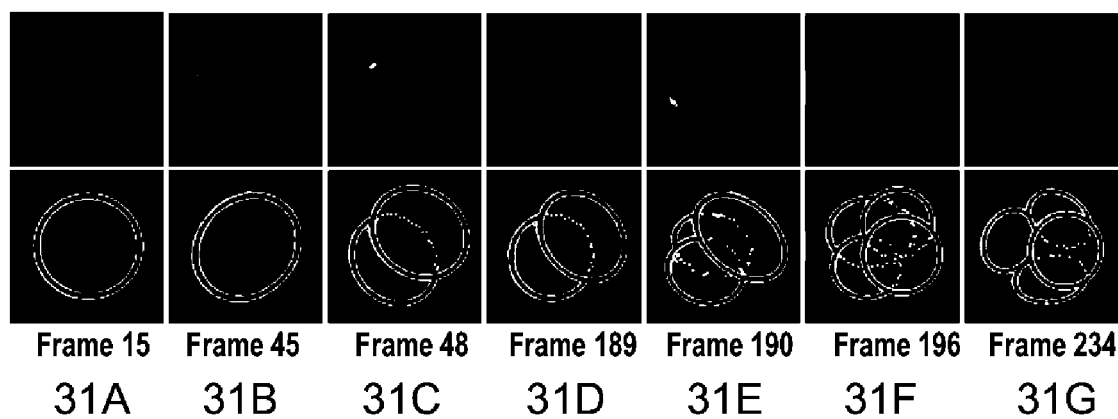
FIG. 31 A-G is a series of seven photographs showing results from 2D tracking at various cell stages. Cells progress as indicated by the frame numbers associated with each picture pair: Frame 15 (FIG. 31A), 45 (B), 48 (C), 189 (D), 190 (E), 196 (F) and 234 (G). The bottom row shows the overlaid simulated images. The contours are visible cell membranes, and the dotted white lines are occluded membranes. Image frames are captured every 5 minutes, and only a few are displayed.

FIG. 31 shows the results of the 2D algorithm for tracking cell divisions from the 1-cell to 4-cell stage. The results show that cell membranes are successfully extracted by the algorithm, even for cells toward the bottom that are partially occluded. It should be noted that in most particle filter applications, the "single" best model is often represented as a weighted sum of the state parameters from the particle distribution. However, for the results presented here, the particle with the highest probability is displayed.

Cell Tracking Example in 3D

Figure 33:
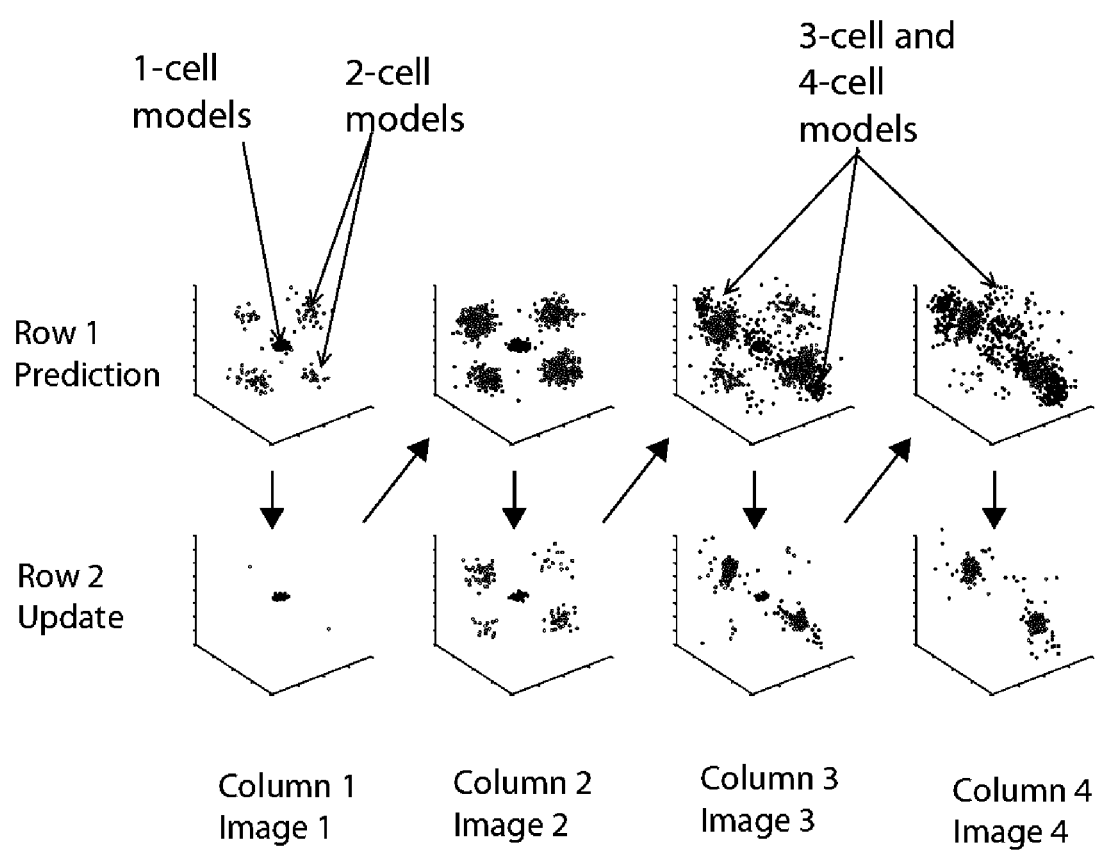
FIG. 33 is a diagrammatic representation of particle filter results for a 1-cell to 2-cell division. The data points are the 3D location of the cell centers. Dots are shown for 1-cell models, 2-cell models, 3-cell models, and 4-cell models. The top row shows the particles after prediction, and the bottom row shows particles after re-sampling.

FIG. 32 shows two successful applications of the above described 3D algorithm for tracking from the 1-cell to 4-cell stage. FIG. 33 is a diagram which shows an example of how particles are distributed during a 1-cell to 2-cell division (corresponding to the first example shown in FIG. 32). This plot shows the 3D location of the centers of each cell. As the cell starts to divide, the predictions show an ambiguity in terms of which daughter cell will lie on top of the other, but this is resolved within a couple of frames.

Extracting Predictive Parameters

Once the embryos have been modeled using the methods previously described, certain parameters can be extracted from the models. Typically, the best or most probable model is used. These parameters include, for example, the duration of first cytokinesis, the time between the first and second cell divisions, and the time between the second and third cell divisions. The duration of cytokinesis can be approximated by measuring how long a model of a cell is elongated before it splits into two cells. Elongation can be measured by looking at the ratio of the major to minor axes of the ellipse. Other parameters that can be extracted from the models include the time between fertilization and the first cell division, shapes and symmetries of cells and division processes, angles of division, fragmentation, etc. Parameters can be extracted using either the 2D cell tracking algorithm or the 3D cell tracking algorithm.

Cytokinesis is defined by the first appearance of the cytokinesis furrow to the complete separation of daughter cells. Since our embryo models are composed of non-deformable ellipses, identifying the appearance of the cytokinesis furrow is a challenging task. One method would be to allow the ellipses to deform, but this results in a more complex tracking problem. Another method would be to look for changes in curvature in the pre-processed microscope image; however, this defeats the purpose of tying to measure our predictive parameters directly from the embryo models. Thus, we simplify the problem by approximating the duration of first cytokinesis as the duration of cell elongation prior to a 1-cell to 2-cell division. Elongation is quantified by calculating the ratio of the major-axis a to minor-axis b of the ellipse. A cell is considered elongated if:

$$\frac{a-b}{b} \geq 15\%$$

This value of 15% was chosen empirically and works well for this particular data set; however other values can be used. Once an embryo model has divided into 2-cells, we can extract the approximated duration of first cytokinesis by calculating the duration of elongation for the 1-cell model.

In principle, measuring the time between mitosis events is straightforward. For example, the time between the first and second mitosis can be measured as the time between the 2-cell model and the 3-cell model. However, in some cases the embryos can exhibit unusual and random behavior. This includes, for example, an embryo that goes from 1-cell to 2-cell, from 2-cell to an apparent 3- or 4-cell, and then back to 2-cell. The described algorithm is capable of tracking this type of behavior, but it poses a challenge for determining the time interval between mitosis events.

One way to deal with this behavior is as follows: Instead of measuring the time between a 2-cell and 3-cell model (in order to find the time between the first and second mitosis), this can be approximated by simply counting the number of image frames in which a 2-cell model is most probable. This works well in some cases, but is not always representative of the true time between mitosis events. One can also deal with these events by enforcing a restriction on the models based on the number of cells. That is, when choosing the best or most probable model from the distribution at each iteration, one can require that the number of cells in the model always stay the same or increase, but never decrease. After enforcing this constraint, it is straightforward to calculate the time between mitosis events. This constraint is also useful for filtering tracking results that may show small amounts of jitter, which can occasionally occur when a model switches back-and-forth between a 1-cell and 2-cell model, for example.

Method for Extracting Predictive Parameters

Figure 35:
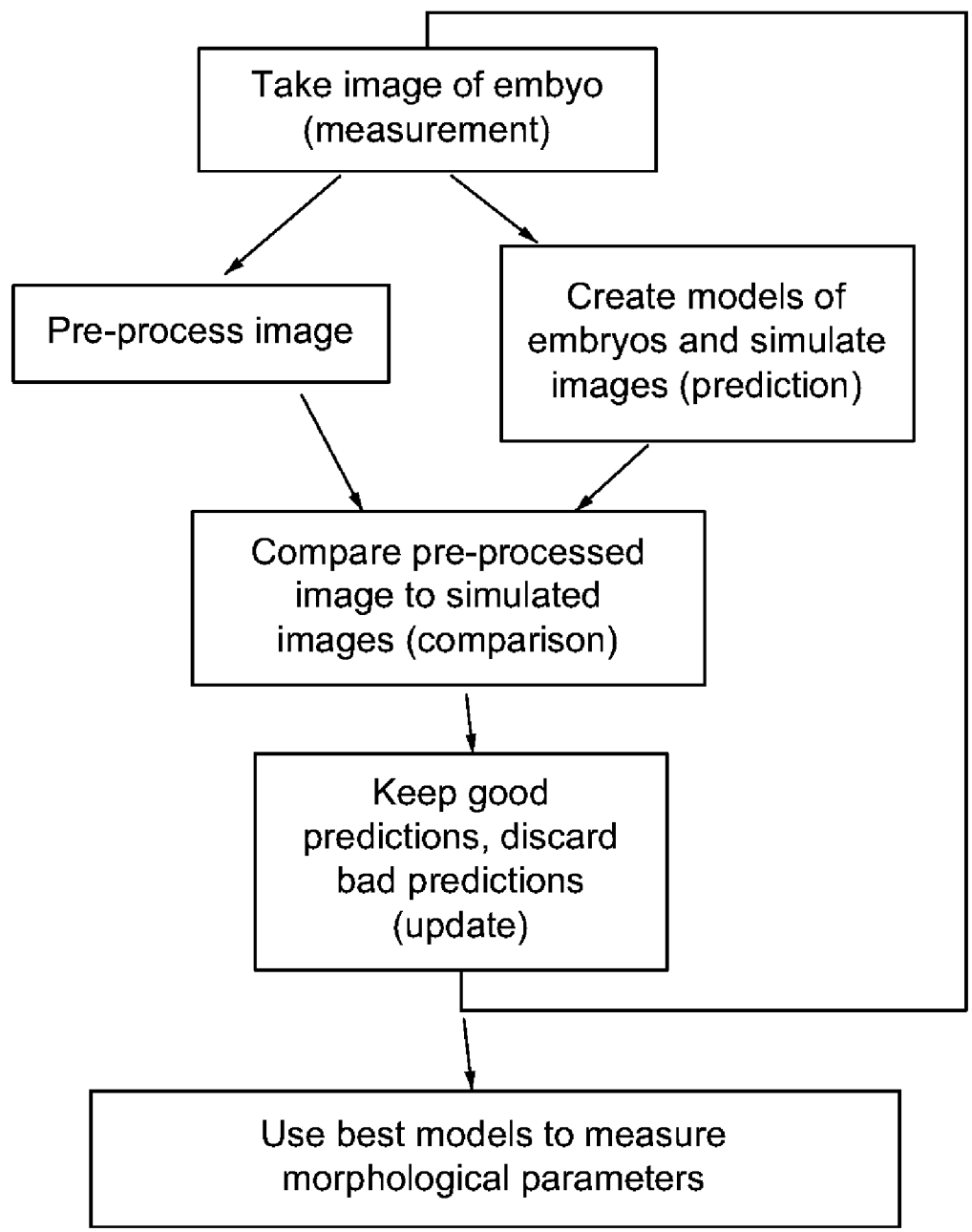
FIG. 35 is a flow chart showing how image analysis is used to model embryos and measure certain morphological parameters.

FIG. 35 shows a flow chart summarizing the methods described above. The flow chart shows how a single embryo can be analyzed (although this can be applied to multiple embryos or other types of cells and stem cells). In the first step, an image of an embryo is acquired with a time-lapse microscope ("measurement"). This image can be saved to file and re-opened at a later point in time. The image is usually pre-processed in order to enhance certain features, although this is not necessary. Models of possible embryo configurations are predicted, and images are simulated from these models ("prediction"). The simulated image could include images of cell membranes, as previously described, or images that more accurately represent the microscope images prior to pre-processing. The models are then compared to the pre-processed microscope image ("comparison"). Using this comparison, the best predictions are kept, while the bad predictions are discarded. The resulting set of predictions is then used to improve the predictions for the next image. After performing this process for multiple sequential images, it is possible to measure morphological parameters directly from the best model(s), such as, for example, the duration of cytokinesis and the time between mitosis events. These parameters can be used to assess embryo viability, as previously discussed.

Example 7

Automated Analysis of Cell Activity

The methods described above require the ability to track cell development via microscopy. For embryos, it is desirable to track multiple embryos, which are being cultured together in the same dish. The analytical methods used here also require that images be taken periodically (e.g. every 1-30 minutes over 1-5 days for embryos; different time intervals may be used for other types of cells such as stem cells). An imaging method was therefore devised to automatically track embryo development.

In time-lapse microscopy, cells are grown under controlled conditions and imaged over an extended period of time to monitor processes such as motility (movement within the environment), proliferation (growth and division), and changes in morphology (size and shape). Due to the length of experiments and the vast amounts of image data generated, extracting parameters such as the duration of and time between cell divisions can be a tedious task. This is particularly true for high-throughput applications where multiple samples are imaged simultaneously. Thus, there is a need for image analysis software that can extract the desired information automatically.

One way to assess embryo viability is to measure the amount of "cell activity" in the images. This can be achieved simply by taking sequential pairs of images and comparing their pixel values. More specifically, to measure the amount of cell activity for each new image, one calculates the sum-of-squared differences (SSD) in pixel intensities between the new image, denoted as I', and the previous image, denoted as I', over all overlapping pixels i:

$$SSD = \sum_i [I'(x'_i, y'_i) - I(x_i, y_i)]^2 = \sum_i e_i^2.$$

To reduce noise, the images can first be smoothed with a Gaussian filter. FIG. 28 shows a plot of the cell activity from day 1 to day 3 for a single embryo. As shown, there are sharp peaks corresponding to the 1-cell to 2-cell division, the 2-cell to 4-cell division, and the 4-cell to 8-cell division in a human embryo. The widths of the peaks are representative of the durations of the cell divisions.

One of the limitations of this approach is that the SSD metric only measures the amount of activity in the image, and events such as embryo motion (such as shifting or rotating) can look quite similar to cell division. One solution to this problem is to perform an image registration prior to calculating the SSD. Image registration is the process of finding a geometric relationship between two images in order to align them in the same coordinate system, and can be achieved using a variety of different techniques. For example, one may use a variation of the Levenberg-Marquardt iterative nonlinear routine, which registers images by minimizing the SSD in overlapping pixel intensities. The LM algorithm transforms pixel locations using a 3×3 homography matrix:

$$\begin{bmatrix} \tilde{x}' \\ \tilde{y}' \\ \tilde{w}' \end{bmatrix} = \begin{bmatrix} h_0 & h_1 & h_2 \\ h_3 & h_4 & h_5 \\ h_6 & h_7 & 1 \end{bmatrix} \begin{bmatrix} x \\ y \\ 1 \end{bmatrix},$$

where the destination pixel locations x' and y' are normalized as:

$$x' = \frac{\tilde{x}'}{\tilde{w}'}, y' = \frac{\tilde{y}'}{\tilde{w}'}.$$

Thus:

$$x' = \frac{h_0 x + h_1 y + h_2}{h_6 x + h_7 y + h_8},$$

$$y' = \frac{h_3 x + h_4 y + h_5}{h_6 x + h_7 y + h_8}.$$

The homography matrix can be applied to a variety of image transformations, and a reasonable choice in this application would be rigid body (Euclidean) transformations. This would align the images of embryos in translation and in-plane rotation (along the camera axis). However, it is possible to generalize slightly and use an affine transformation, which allows for image skewing. This generalization may or may not be desirable depending on the signal trying to be measured. The motion equations thus become:

$$x' = h_0 x + h_1 y + h_2$$

$$y' = h_3 x + h_4 y + h_5.$$

The LM algorithm first calculates the partial derivatives of e with respect to the unknown motion parameters $h_k$ using the chain rule:

$$\frac{\delta e}{\delta h_k} = \frac{\delta I'}{\delta x'} \frac{\delta x'}{\delta h_k} + \frac{\delta I'}{\delta y'} \frac{\delta y'}{\delta h_k}.$$

For the affine motion parameters, these partial derivatives become:

$$\frac{\delta e}{\delta h_0} = x \frac{\delta I'}{\delta x'},$$

$$\frac{\delta e}{\delta h_1} = y \frac{\delta I'}{\delta x'},$$

$$\frac{\delta e}{\delta h_2} = \frac{\delta I'}{\delta x'},$$

$$\frac{\delta e}{\delta h_3} = x \frac{\delta I'}{\delta y'},$$

$$\frac{\delta e}{\delta h_4} = y \frac{\delta I'}{\delta y'},$$

$$\frac{\delta e}{\delta h_5} = \frac{\delta I'}{\delta y'}.$$

Next, using these partial derivatives, the LM algorithm computes the approximate Hessian matrix A (in the set of real numbers of size 6×6) and weighted gradient vector b (in the set of real numbers of size 6×1) by adding the contribution from each pixel:

$$a_{ki} = \sum_i \frac{\delta e_i}{\delta h_k} \frac{\delta e_i}{\delta h_i},$$

$$b_k = -\sum_i \frac{\delta e_i}{\delta h_k}.$$

Finally, the motion parameters can be updated by adding the incremental motion $$\Delta H = (A + \lambda I)^{-1} b,$$

where the constant λ regulates the step size of the motion update and I is the identity matrix.

At each iteration of the algorithm, the first image is warped according to the updated motion estimate and compared to the second image by computing the SSD of pixel intensities in areas of overlap. The present application assumes that the embryo motion between consecutive images is very small, and therefore only a small, fixed number of iterations are performed. FIG. 28B shows a plot of cell activity without (28A) and with (28B) image registrations performed for each pair of images. Since the error function of the Levenberg-Marquardt routine is the SSD, one simply plots the residual error for each registration. FIG. 29 compares plots of cell activity for normal and abnormal embryo development. At day 3, the point at which an embryologist would typically evaluate morphology, the embryos look similar and could potentially both be considered viable. However, their cell activity plots are drastically different, as one of the embryos undergoes a typical series of cell divisions while the other splits from a 1-cell embryo into multiple cells and fragments. As expected, the embryo that has a normal activity plot ultimately reaches blastocyst by day 5.5.

Other types of image registration may be used prior to calculating the SSD in pixel intensities. This includes, for example, cross correlation, normalized cross correlation, cross phase correlation, mutual information, feature detection and tracking, scale invariant feature transform (SIFT), optical flow, and gradient descent. Image pre-processing may or may not be desirable prior to registration, such as feature or contrast enhancement.

Model for Assessing Embryo Viability

FIG. 13 shows a model for human embryo development based on correlated imaging and molecular analysis. Shown is the timeline of development from zygote to blastocyst including critical brief times for prediction of successful development to blastocyst and a diagram of embryo development. Key molecular data, as diagrammed, indicates that human embryos begin life with a distinct set of oocyte RNAs that are inherited from the mother. This set of RNAs is maintained and packaged properly by specific RNA management programs in the egg. Following fertilization, degradation of a subset of maternal RNAs specific to the egg (ESSP1; Embryonic Stage Specific Pattern 1) must be degraded as the transition from oocyte to embryo begins. In parallel, other RNAs are ideally partitioned equally to each blastomere as development continues (ESSP4). The successful degradation and partitioning of RNAs culminates with embryonic genome activation (EGA) and transcription of the genes of ESSP2 in a cell autonomous manner. Notably, during the cleavage divisions, embryonic blastomeres may arrest or progress independently. The outcome of cell autonomous development in the embryo is that individual blastomeres may arrest or progress and as the 8-cell embryo progresses to morula stage and beyond, blastocyst quality will be impacted by the number of cells that arrested or progressed beyond 8 cells. Imaging data demonstrates that there are critical periods of development that predict success or failure: first cytokinesis, the second cleavage division and synchronicity of the second and third cleavage divisions. These parameters can be measured automatically using the cell tracking algorithms and software previously described. The systems and methods described can be used to diagnose embryo outcome with key imaging predictors and can allow for the transfer of fewer embryos earlier in development (prior to EGA). Comparison of automated vs. manual image analysis FIG. 34 shows a comparison of the automated image analysis to manual image analysis for a set of 14 embryos. Embryos 1 through 10 (as labeled on the plots) reached the blastocyst stage with varying morphology. Embryos 11 through 14 arrested and did not reach blastocyst. FIG. 34A shows the comparison for measuring the duration of first cytokinesis, and FIG. 34B shows the comparison for measuring the time between 1st and 2nd mitosis. As shown, the two methods show good agreement in general. The small amounts of discrepancy for the duration of first cytokinesis are expected, as they can be attributed to the fact that our automated analysis makes an approximation by measuring elongation, as previously discussed. In a few cases, there is a larger disagreement between the automated and manual analysis for both the duration of cytokinesis as well as the time between 1st and 2nd mitosis. This occurs for a few of the abnormal embryos, and is caused by unusual behavior that is both difficult to characterize manually as well as track automatically. For this group of embryos, and using just the first two criteria (duration of first cytokinesis and time between 1st and 2nd mitosis), the automated algorithm has zero false positives. This would be extremely important in an IVF procedure where false positives must be avoided. Manual image analysis had one false negative (embryo 9), while the automated algorithm had two false negatives (embryos 9 and 10). However, while both embryos 9 and 10 technically reached the blastocyst stage, they showed poor morphology compared to other blastocysts and would be less optimal candidates for transfer. For manual image analysis, embryo 14 would be a false positive based on these two criteria, and the third parameter of duration between 2nd and 3rd mitosis is needed to give a true negative. However, the automated algorithm makes the correct prediction using only the first two criteria. These results indicate that our automated algorithm can successfully predict blastocyst vs. non-blastocyst as well as differentiate between different qualities of blastocyst. Thus, for situations when multiple embryos are determined to have good developmental potential, it is possible to calculate a ranking of their relative qualities, in order to select the top 1 or 2 embryos for transfer during IVF procedures.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method for assessing the potential for developmental competence of a human embryo comprising
   1) measuring cellular parameters of human embryo in vitro, wherein said cellular parameters include:
   (a) the duration of the first cytokinesis;
   (b) the time interval between cytokinesis 1 and cytokinesis 2; or
   (c) the time interval between cytokinesis 2 and cytokinesis 3, and
   2) determining that the human embryo has greater potential for developmental competence when,
   (a') the duration of the first cytokinesis is about 0 to about 30 minutes;
   (b') the time interval between the resolution of cytokinesis 1 and the onset of cytokinesis 2 is about 8-15 hours; or
   (c') the time interval between the onset of cytokinesis 2 and the onset of cytokinesis 3 is about 0-5 hours.

2. The method of claim 1 wherein the cellular parameters include:
   (a) the duration of the first cytokinesis;
   (b) the time interval between cytokinesis 1 and cytokinesis 2; and
   (c) the time interval between cytokinesis 2 and cytokinesis 3.

3. The method of claim 1, wherein said cellular parameters are measured by time-lapse microscopy.

4. The method of claim 1, wherein said cellular parameters further comprise the duration of cell cycle 1.

5. The method of claim 4, wherein greater potential for developmental competence of said human embryo is indicated when the duration of cell cycle 1 is about 20 to about 27 hours.

6. The method of claim 1, wherein poor developmental potential of said human embryo is indicated by
   (a) a longer cytokinesis for said human embryo than for said reference human embryo;
   (b) a longer or shorter time interval between the resolution of cytokinesis 1 and the onset of cytokinesis 2 for said human embryo than for said reference human embryo; and/or
   (c) a longer time interval between the initiation of cytokinesis 2 and the onset of cytokinesis 3 for said human embryo than for said reference human embryo.

7. The method of claim 6, wherein said cellular parameters further comprise the duration of cell cycle 1.

8. The method of claim 7, wherein poor developmental competence of said human embryo is indicated when the duration of cell cycle 1 is longer than about 27 hours.

9. The method of claim 1, wherein said embryos are produced by fertilization of oocytes in vitro.

10. The method of claim 1, wherein said oocytes are matured in vitro.

11. The method of claim 10, wherein said oocytes matured in vitro are supplemented with growth factors.

12. The method of claim 1, wherein the embryos have not been frozen prior to measuring the parameters.

13. The method of claim 1, wherein the embryos have been frozen prior to measuring the parameters.

14. The method of claim 1 further comprising implanting the human embryo determined to have greater potential for developmental competence into a female human subject.

* * * * *